(12) United States Patent
Curiel et al.

(10) Patent No.: US 12,357,183 B2
(45) Date of Patent: Jul. 15, 2025

(54) SYSTEM AND APPARATUS FOR AUTOMATED TOTAL BODY IMAGING

(71) Applicant: DermSpectra LLC, Stafford, NH (US)

(72) Inventors: Clara Curiel, Tucson, AZ (US); Karleen Seybold, Tucson, AZ (US); Michael Bertino, San Luis Obispo, CA (US); Michael Patton, San Luis Obispo, CA (US)

(73) Assignee: Tochara LLC, York, ME (US)

( * ) Notice: Subject to any disclaimer, the term of this patent is extended or adjusted under 35 U.S.C. 154(b) by 1014 days.

(21) Appl. No.: 15/727,487

(22) Filed: Oct. 6, 2017

(65) Prior Publication Data

US 2018/0125370 A1 May 10, 2018

Related U.S. Application Data

(63) Continuation of application No. 13/778,942, filed on Feb. 27, 2013, now abandoned.
(Continued)

(51) Int. Cl.
*A61B 5/00* (2006.01)

(52) U.S. Cl.
CPC .......... *A61B 5/0077* (2013.01); *A61B 5/0046* (2013.01); *A61B 5/444* (2013.01);
(Continued)

(58) Field of Classification Search
CPC ..... A61B 5/0077; A61B 5/6888; A61B 5/702; A61B 5/706; A61B 5/7445; A61B 5/0046; A61B 5/444; A61B 5/7425; A61B 5/7405; A61B 5/741; A61B 5/0013; A61B 5/70; A61B 5/0033; A61B 5/74; A61B 5/742; A61B 5/745; A61B 5/445; A61B 5/441; A61B 5/1074; A61B 2562/0252; A61B 5/0064; A61B 5/277; A61B 5/302; A61B 2018/147; A61B 2562/0214; A61B 2562/021; A61B 3/0083; A61B 6/0492;
(Continued)

(56) References Cited

U.S. PATENT DOCUMENTS 4,406,544 A 9/1983 Takada et al.
4,492,236 A 1/1985 Pile
(Continued)

FOREIGN PATENT DOCUMENTS

EP 1433418 A1 6/2004
WO 2009/070313 A1 6/2009
WO 2012/008856 A1 1/2012

OTHER PUBLICATIONS

Sato, M. Poupyrev, I, and Harrison, C. 2012. Touche: Enhancing Touch Interaction on Humans, Screens, Liquids, and Everyday Objects. In Proceedings of the 30th Annual SIGCHI Conference on Human Factors in Computing Systems (Austin, Texas, May 5-10, 2012). CHI '12. ACM, New York, NY. 483-492. (Year: 2012).*

*Primary Examiner* — Jeffrey G Hoekstra
*Assistant Examiner* — Amy Shafqat
(74) *Attorney, Agent, or Firm* — Zeman-Mullen & Ford, LLP

(57) ABSTRACT

An imaging station/booth for automated total body imaging having a small footprint and capable of quickly, efficiently, effectively, and consistently capturing multiple body images of a user or patient over time with minimal assistance from medical staff.

19 Claims, 44 Drawing Sheets

Related U.S. Application Data

(60) Provisional application No. 61/643,638, filed on May 7, 2012.

(52) U.S. Cl.
CPC ............ A61B 5/6888 (2013.01); A61B 5/702 (2013.01); A61B 5/706 (2013.01); A61B 5/7405 (2013.01); A61B 5/7425 (2013.01); A61B 5/7445 (2013.01); A61B 5/0013 (2013.01); A61B 5/70 (2013.01); A61B 5/741 (2013.01)

(58) Field of Classification Search
CPC . H04N 5/23238; H04N 5/247; H04N 5/23293
See application file for complete search history.

(56) References Cited

U.S. PATENT DOCUMENTS

| | | | |
|---|---|---|---|
| 5,016,173 A | 5/1991 | Keret et al. | |
| 5,481,509 A | 1/1996 | Knowles | |
| 5,850,290 A | 12/1998 | Horiguchi et al. | |
| 6,002,743 A | 12/1999 | Telymonde | |
| 6,141,434 A | 10/2000 | Christian et al. | |
| 6,151,521 A | 11/2000 | Guo et al. | |
| 6,205,716 B1 | 3/2001 | Peltz | |
| 6,215,893 B1 | 4/2001 | Leshem et al. | |
| 6,993,167 B1 | 1/2006 | Skladnev et al. | |
| 7,162,063 B1 | 1/2007 | Craine et al. | |
| 7,415,143 B2 | 8/2008 | Grichnik | |
| 7,415,204 B1 | 8/2008 | Rosewarne et al. | |
| 7,457,659 B2 | 11/2008 | Maschke | |
| 7,657,101 B2 | 2/2010 | Christiansen, II et al. | |
| 7,689,016 B2 | 3/2010 | Stoecker et al. | |
| 7,894,651 B2 | 2/2011 | Gutkowicz-Krusin et al. | |
| 8,026,942 B2 | 9/2011 | Payonk et al. | |
| 8,030,582 B2 | 10/2011 | Tanida et al. | |
| 8,068,675 B2 | 11/2011 | Christiansen, II et al. | |
| 8,194,952 B2 | 6/2012 | Mertz et al. | |
| 8,351,770 B2 | 1/2013 | DePaula et al. | |
| 2002/0024517 A1 | 2/2002 | Yamaguchi et al. | |
| 2004/0057608 A1* | 3/2004 | Souluer | A61B 5/6843 382/128 |
| 2004/0085514 A1 | 5/2004 | Fransen | |
| 2005/0083333 A1 | 4/2005 | Gordon | |
| 2005/0119551 A1 | 6/2005 | Maschke | |
| 2005/0179778 A1* | 8/2005 | Nakanishi | G07F 17/26 348/207.2 |
| 2006/0291189 A1 | 12/2006 | Mahgerefteh | |
| 2007/0098368 A1 | 5/2007 | Carley et al. | |
| 2007/0299334 A1 | 12/2007 | Vilsmeier | |
| 2008/0049990 A1 | 2/2008 | Melchi et al. | |
| 2008/0114270 A1* | 5/2008 | DiSilvestro | A61B 5/4528 600/595 |
| 2008/0194968 A1 | 8/2008 | Drugge | |
| 2009/0060304 A1* | 3/2009 | Gulfo | A61B 5/7445 382/128 |
| 2009/0118600 A1 | 5/2009 | Ortiz | |
| 2009/0185727 A1 | 7/2009 | Beckmann et al. | |
| 2009/0196475 A1 | 8/2009 | Demirli et al. | |
| 2009/0304243 A1 | 12/2009 | Mertz et al. | |
| 2010/0111387 A1 | 5/2010 | Christiansen, II et al. | |
| 2010/0232773 A1 | 9/2010 | DePaula et al. | |
| 2010/0321946 A1 | 12/2010 | Dingman et al. | |
| 2011/0273535 A1 | 11/2011 | Mendelson | |
| 2011/0284632 A1 | 11/2011 | Mullen et al. | |
| 2015/0327765 A1 | 11/2015 | Crane | |

* cited by examiner

Patient Information Entry Form

Auto Fill Other
Info on Tab/Enter

- Patient ID
- Last Name
- Date of Birth
- Study ID
- Middle Initial
- Skin Type
- Study Date
- First Name
- Demo Button
- SUBMIT Button This button should stand out.
Launches Pose Selection - 2

Text Boxes — 700

Buttons — 702

FIG. 46

SYSTEM AND APPARATUS FOR AUTOMATED TOTAL BODY IMAGING

CROSS-REFERENCE TO RELATED APPLICATIONS

This application is a continuation of and claims benefit of priority to U.S. Nonprovisional patent application Ser. No. 13/778,942 filed Feb. 27, 2013, which claims priority to provisional patent application having Ser. No. 61/643,638, filed May 7, 2012, which applications are herein incorporated by reference in their entirety.

FIELD OF INVENTION

The present invention generally relates to a system and apparatus for automated total body imaging. More particularly, the present invention relates to a system and apparatus for automated total body imaging which includes a streamlined imaging station/booth having a small footprint for use in medical offices which is capable of quickly, efficiently, effectively and consistently capturing multiple body images of a user or patient with minimal assistance from medical staff.

BACKGROUND OF THE INVENTION

Skin related conditions and diseases, including skin cancer, must involve monitoring of the skin in order to diagnose and/or monitor the condition or disease as well as evaluate treatment for the condition or disease. In addition, skin must be monitored to identity skin related side effects and events related to evaluating experimental as well as well established treatments for various diseases.

Skin cancer is the most common form of cancer in the United States. Each year there are more new cases of skin cancer than the combined incidences of breast cancer, prostate cancer, lung cancer, and colon cancer and, over the past 31 years, more people have had skin cancer than all other cancers combined. Each year, more than 3.5 million cases of skin cancer are diagnosed in the U.S.

There are three main types of skin cancer—basal cell carcinoma, squamous cell carcinoma, and melanoma. Basal cell carcinoma is the most common form of skin cancer and an estimated 2.8 million people are diagnosed annually with it in the U.S. Basal cell carcinomas are rarely fatal but can be highly disfiguring if allowed to grow. Squamous cell carcinoma is the second most common form of skin cancer. An estimated 700,000 cases are diagnosed each year in the U.S. and result in approximately 2,500 deaths.

Melanoma is a third form of skin cancer and is the most common form of cancer for young adults ages 25 to 29 and the second most common form of cancer for young people aged 15 to 29. Melanoma is the fifth most common cancer for males and the sixth most common cancer for females. The incidence of melanoma continues to rise and one in 55 people will be diagnosed with melanoma in their lifetime. The survival rate for people whose melanoma is detected early, before the tumor has penetrated the skin, is about 99 percent. However, the survival rate falls to 15 percent for those with advanced disease.

The total direct cost associated with the treatment for nonmelanoma skin cancer in 2004 was 1.5 billion dollars. The number of nonmelanoma skin cancers in the Medicare population went up an average of 4.2 percent every year between 1992 and 2006. Melanoma treatment costs total about 249 million dollars annually for adults 65 and older. Although they only account for three percent of melanomas, about 40 percent of the annual cost for melanoma treatment sees to treating stage IV cancers.

Although skin cancer cases are on the rise, early detection of skin cancer can play a significant role in its treatment and the costs associated with treatment. Self-exams coupled with yearly skin exams by physicians are the best way to achieve early detection. Accordingly, there is a need for quick, efficient, effective and consistent body-imaging of individuals/patients so that a physician can easily examine the body images of the individual/patient for skin neoplasms and/or skin variations that require further examination. In addition, there is a need for an automated body imaging system to document and monitor the skin for a number of reasons in addition to skin cancer surveillance. These reasons include, but are not limited to, identification of skin related side effects/events in clinical trials, evaluation of clinical response to a variety of experimental and well established treatments for the management of psoriasis, cutaneous lymphoma, hypersensitivity reactions, etc., cosmetic procedures, and any other application where skin imaging may be useful.

SUMMARY OF THE INVENTION

The present invention is directed toward an automated system and apparatus for total body imaging which includes an imaging station/booth for automatically capturing body images of a user when the user is positioned in predetermined poses. The predetermined poses enable thorough and accurate viewing for detecting skin abnormalities on the user and the user is given an audio and/or visual step by step guide through the poses. The system determines if the user is correctly positioned for a predetermined pose and communicates successful positioning to the user before automatically capturing the body image of the user with one or more cameras.

Key features of the imaging station/booth of the present invention include, but are not limited to, a compact and small footprint for the station/booth itself, patient privacy during imaging, display screens in the station/booth which guide users through the poses for total body imaging, and sensors in communication with positioning indicia and/or positioning members (such as handles, footprints, and/or handprints) to determine correct positioning for a pose and communicating successful positioning to the user. Key features of the automated system for full body imaging of the present invention include, but are not limited to, rapid/quick collection of precise total body imaging, automated imaging acquisition by guiding users through positions and determining and communicating correct positioning via sensors, patient privacy during imaging, and wireless access to images so that medical professionals can determine skin abnormalities and/or make diagnoses without the need to be present during imaging or at the site of imaging. Another key feature of the automated total body imaging system of the present invention is its ability to interface with electronic medical records (EMRs). An electronic medical record (EMR) is a computerized medical record created in an organization that delivers care such as a hospital or physician's office.

In one exemplary embodiment, the system for total body imaging of the present invention includes i) an imaging station/booth having one or more body positioning indicia or body positioning members (such as a handle, footprint, and/or handprint), a sensor in communication with the body positioning indicia and/or body positioning members, one or more cameras, one of more lighting elements, and one or more display screens, ii) a program application in communication with the imaging station/booth for guiding a user through one or more predetermined poses via the display screen in the imaging station/booth, capturing the user's images in each predetermined pose via the one or more cameras, and documenting notes relating to the images, and iii) a computing device in communication with the program application for storing the images, accessing and viewing the images, and inputting information relating to the images. The computing device may be connected (i.e. wired) to another computing device to enable a medical professional/medical provider to access user images and data. In addition, the computing device may be connected (e.g. wired) to a visual display and/or computing device that enables a technician/medical assistant to control capture of the user images by use of a graphic user interface specifically designed for the technician/medical assistant. The system may also include a server in communication with a network so that user images can be wirelessly accessed by medical professionals through the wireless network and the medical professional can document notes and/or comments relating to the images. In addition, the server may access external databases to aid the medical professional in analyzing the user images. In particular, the system for total body imaging of the parent invention may interface with electronic medical records (EMRs). The total body imaging system of the present invention may deliver imaging results in the form of EMRs to a physician, medical professional, and/or medical facility such as a hospital or clinic and or the total body imaging system of the present invention may interface with existing EMR databases from other medical providers and/or facilities for individuals/patients that undergo the total body imaging of the present invention so that the total body imaging of the present invention can also be compared to the EMRs in those other databases.

One exemplary embodiment of the imaging station/booth of the present invention includes one or more body positioning indicia or body positioning members (such as a handle, footprint, and/or handprint), a sensor in communication with each of the body positioning indicia and/or body positioning members, one or more cameras, one or more lighting elements, and one or more display screens. The imaging station/booth may also include a privacy screen that is formed by opening a portion of the housing which comprises the perimeter of the imaging station/booth. The imaging station/booth may also include a movable/retractable step for assisting in body positioning of the user where the movable/retractable step can be recessed into the floor of the imaging station/booth.

A second exemplary embodiment of the imaging station/booth of the present invention includes an enclosed interior area, a door enabling a user to enter the enclosed interior area, and a plurality of cameras which together provide overlapping images of the user wherein the plurality of cameras exist in stationary positions and are not capable of repositioning. The total body imaging station/booth may also include one or more body positioning members located within the enclosed interior area which assist a user in accurately positioning his/her body for a series of one or more predetermined poses, at least one image display device located within the enclosed interior area that is viewable by a user, at least one light panel positioned near the cameras, at least one speaker component for enabling a user to hear voice instructions within the enclosed interior area, and a computer processing unit in communication with one or more program applications related to the use of she total body imaging station/booth. The one or more body positioning members may each include a light emitting component having capacitive touch sensors to enable the body positioning members to light up when properly engaged by a user during a series of predetermined poses.

The enclosed inner area of the second exemplary embodiment may be defined by a front panel, two opposing side panels, a rear panel, and a top cover member. One or both of the opposing side panels may function as a door or a door may be located within one or both of the opposing side panels. Further, the front panel may be positioned in front of the plurality of cameras and include a plurality of openings so that a lens of each of the cameras can be seen through each of the openings, respectively. In addition, the front panel may also include at least two vertically oriented rectangular openings that are positioned such that at least two light panels cars be inserted into each of the vertically oriented rectangular openings, respectively.

The one or more program applications in communication with the computer processing unit may include a program application for taking, capturing, and storing the overlapping images obtained from the plurality of cameras. The program application(s) can also include an automatic focusing algorithm to automate the focusing of the plurality of cameras by determining an area of interest for each camera in each of the predetermined body poses that are undertaken by a user. The program application(s) may also include a program application that enables a medical professional and/or medical facility (such as hospitals, medical clinics, etc.) to obtain wireless access to the overlapping images in order to view the overlapping images, compare a plurality of the overlapping images of a same user taken at different times, document notes relating to the overlapping images, create electronic medical records that include the overlapping images, and/or send the overlapping images and related notes to another medical professional and/or medical facility.

Still a third exemplary embodiment of the total body imaging station/booth of the present invention includes an enclosed interior area, a door enabling a user to enter the enclosed interior area, one or more body positioning members located within the enclosed interior area for assisting a user in accurately positioning his/her body in a series of one or more predetermined body poses, a plurality of cameras which together provide overlapping images of the user in the predetermined body pose(s) where the overlapping images have up to 15% overlap and cover an area up to at least 6 feet 5 inches in height and the cameras exist in a stationary position and are not capable of repositioning, at least one panel positioned near the cameras, and at least one image display device located within the enclosed interior area that is viewable by the user. The total body imaging station/booth may also include at least one speaker component to enable a user to hear voice instructions within the enclosed interior area.

The one or more body positioning members may include one or more handles for the user's hands and a footplate for the user's foot or feet and the handles and/or foot plate may each include a light emitting component with capacitive touch sensor to enable the handles and/or footplate to light up when properly engaged by the user when performing the predetermined body pose(s). In addition, the footplate may be vertically moveable and retractable within the floor of the total body imaging station/booth. As seen in one exemplary embodiment, the plurality of cameras may include nine separate cameras that are each secured to a frame so that the cameras create an array of three horizontal rows of cameras with three cameras secured to each horizontal row.

The third exemplary embodiment of the total body imaging station/booth may also include a panel positioned in front of the cameras having a plurality of circular openings so that a lens from each of the cameras can be seen through each of the circular openings, respectively. Further, the light panel in the total body imaging station/booth may include two light panels positioned on opposite sides of the cameras and the panel positioned in front of the cameras may also include at least two vertically oriented openings so that a front of each of the light panels can be inserted into each of the two vertically oriented openings, respectively.

The total body imaging station/booth may also include a computer processing unit in communication with one or more program applications related to the use of the total body imaging station/booth. The program application(s) may include a program application for guiding a user through a series of one or more predetermined body poses by utilizing the imaging display device and/or the speaker component(s). The program application(s) may also include a program application for taking, capturing, and storing the overlapping images obtained from the plurality of cameras. The program application(s) can also include an automatic focusing algorithm to automate the focusing of the plurality of cameras by determining an area of interest for each camera in each of the predetermined body poses that are undertaken by a user. The program application(s) may also include a program application that enables a medical professional and/or medical facility (such as hospitals, medical clinics, etc.) to obtain wireless access to the overlapping images in order to view the overlapping images, compare a plurality of the overlapping images of a same user taken at different times, document notes relating to the overlapping images, create electronic medical records that include the overlapping images, and/or send the overlapping images and related notes to another medical professional and/or medical facility. Further, the program application(s) can include a program application that enables a medical professional and/or medical facility having access to the overlapping images of a user to interface with other existing electronic medical record databases from other medical professionals and/or medical facilities utilized by the user so that the overlapping images of the use can be compared to other existing electronic record databases. The total body imaging station/booth may also include a technician computer device located outside the enclosed interior area that enables a technician to control one or more of the program applications.

BRIEF DESCRIPTION OF THE DRAWINGS

The figures illustrate various embodiments of the present invention by way of example, and not by way of limitation. Embodiments of the present invention may include part or all of the features shown in one of these figures, or may include features from two or more figures. Embodiments of the present invention may also include features described in the specification, or elements of features described in the specification. Furthermore, embodiments of the present invention may include features that would be familiar to a person of ordinary skill in the art having studied this document. Thus, a more complete understanding of the present invention may be derived by referring to the detailed description and claims when considered in connection with the drawing figures where like reference numbers refer to similar elements throughout the figures.

FIGS. 46 through 53 show exemplary frames/screen shots of the graphic user interface for technicians or medical assistants used with the imaging station/booth shown in FIGS. 25 and 26 to ensure that the automated imaging is correctly carried out and completed wherein each frame/screen shot corresponds to main windows and subsequent pop up windows in the graphical user interface.

DETAILED DESCRIPTION OF EXEMPLARY EMBODIMENTS

The present invention is directed to a system and apparatus for total body imaging where the system includes an imaging station/booth, a program application in communication with the imaging station/booth, and a computing device in communication with the program application. The total body imaging system and apparatus of the present invention may fee used for a large number of applications including, but not limited to, skin cancer surveillance, identification of skin related side effects/events in clinical trials, evaluation of clinical response to a variety of experimental and well established treatments for the management of psoriasis, cutaneous lymphoma, hypersensitivity reactions, etc., cosmetic procedures, and any other application where skin imaging may be useful.

Figure 1:
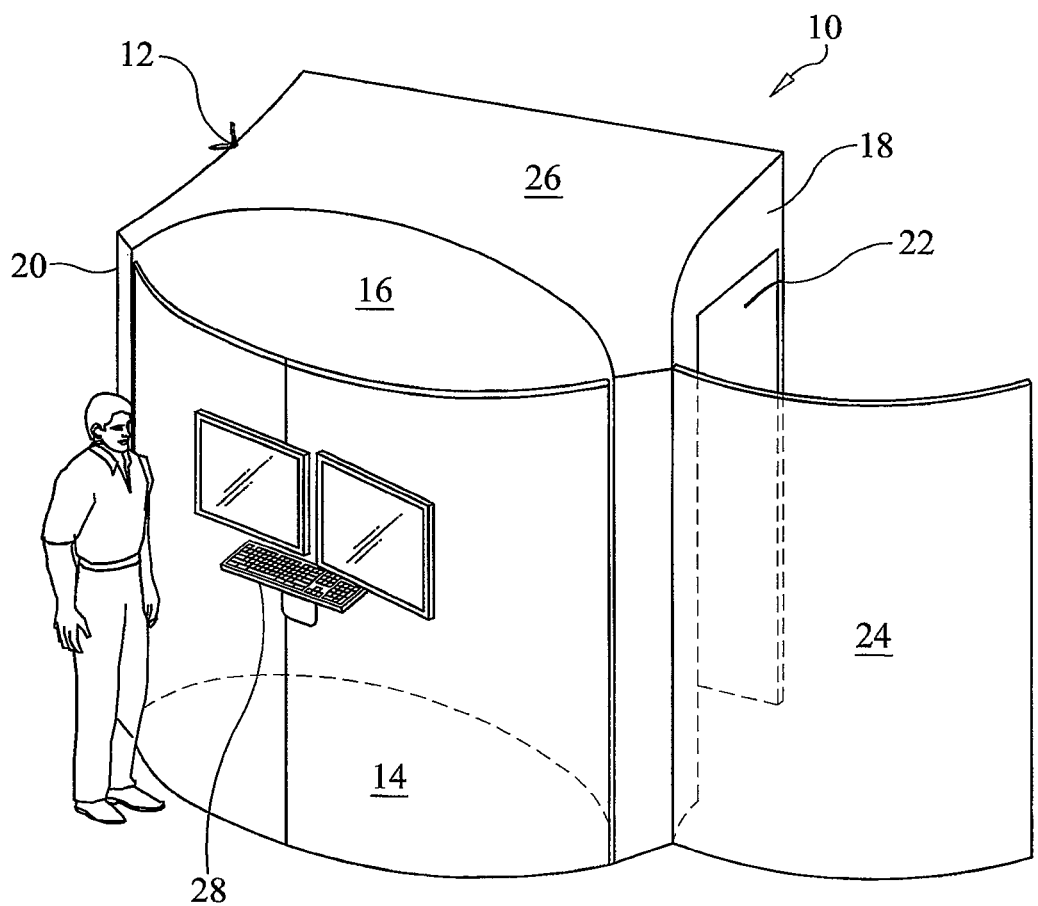
FIG. 1 is an outer perspective view of one exemplary embodiment of the imaging station/booth in accordance with the present invention.

An outer perspective view of one exemplary embodiment of the imaging station/booth 10 in accordance with the present invention is shown in FIG. 1. Imaging station/booth 10 includes a housing 12 having two front walls 14, 16, a first side wall 18 having an opening therein for user entry into the imaging station/booth 10, a second side wall 20, a back wall 22, a door 24 which covers the opening in side wall 18, and a top member 26. Door 24 may act as a privacy screen when opened for accessing the interior of the imaging station/booth 10. Top member 26 may be sloped and front walls 14, 16 may be semi-oval in shape so that they form an oval shaped interior space when their open ends are joined together. In one another exemplary embodiment, the top member 26 and the front walls 14, 16 may be comprised of a frosted polypropylene that is approximately 3/16 of an inch to 1/4 of an inch thick. The high chemical resistance of the frosted polypropylene makes it ideal for wiping it down. A computer 28 for use by a technician or medical assistant may be positioned on the exterior surface of front wall 14 so that the technician can input information into the program application and make selections in accordance with the program application.

Figure 2:
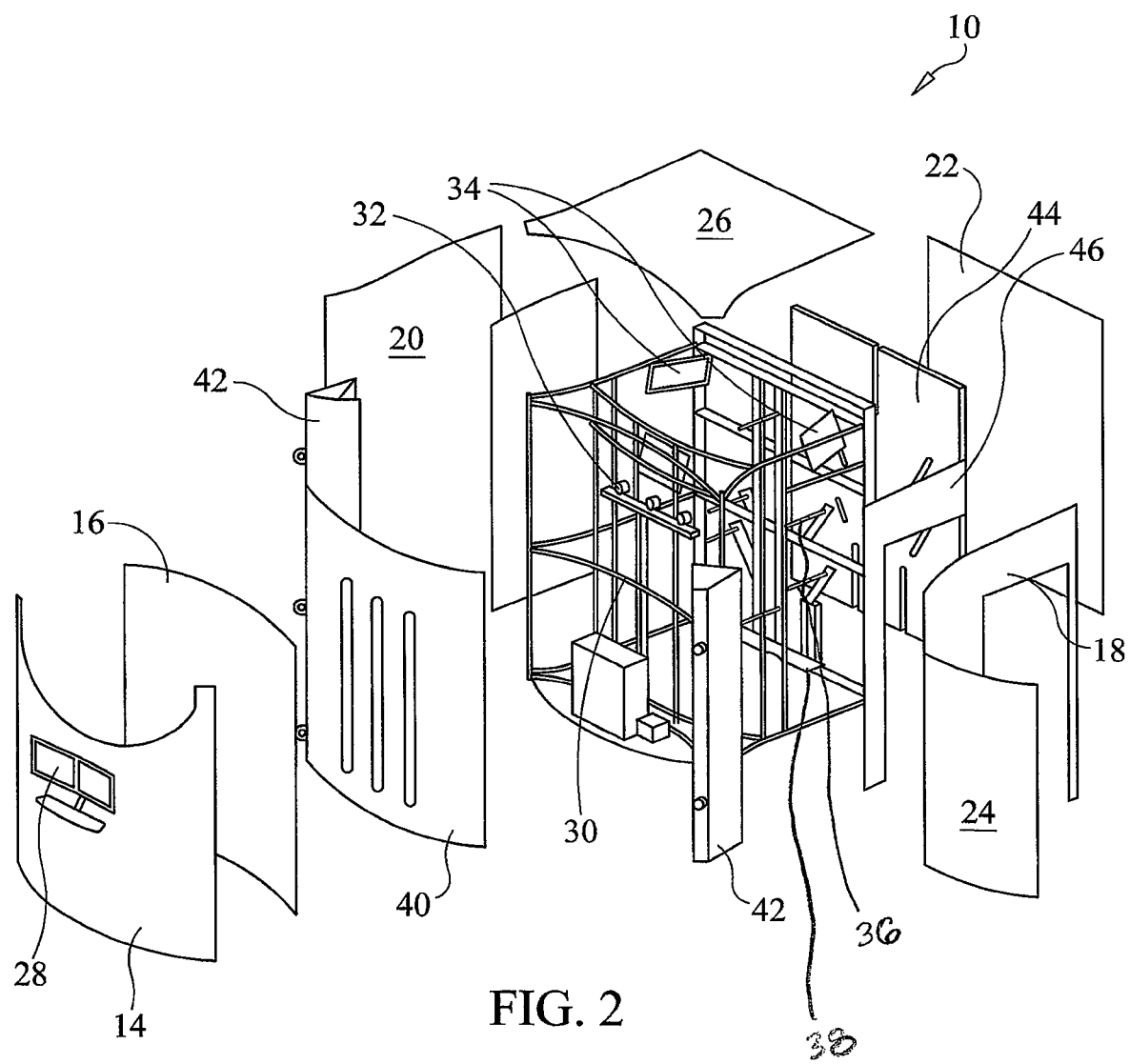
FIG. 2 is an exploded view of the exemplary embodiment of the imaging station/booth of the present invention shown in FIG. 1.

FIG. 2 is an exploded view of the exemplary embodiment of the imaging station/booth 10 of the present invention shown in FIG. 1. Imaging station/booth 10 includes housing having two front walls 14, 16, a first side wall 18 having an opening therein for user entry into the imaging station/booth 10, a second side wall 20, a back wall 22, a door 24 which covers the opening in side wall 18, and a top member 26. In addition, a frame 30 is located within the housing for mounting cameras 32, video displays 34, handle members 36, and a movable step 38. The housing may further include additional panel members such as front panel 40, corner panels 42 for enclosing light boxes, back panel 44, and side panel 46—all of which also function to add additional durability, strength, and support to the imaging station/booth 10. In one exemplary embodiment, the frame 30 may be aluminum and the walls and panels of the housing may be comprised of a plastic.

Figure 3:
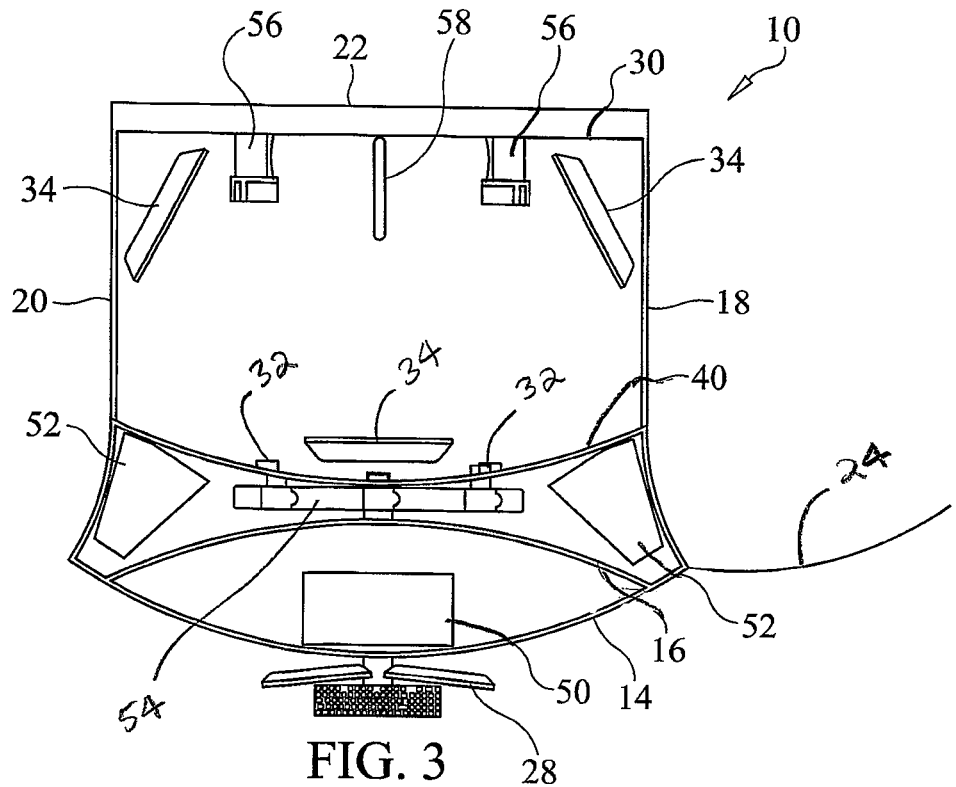
FIG. 3 is a top plan view showing the interior of the exemplary embodiment of the imaging station/booth of the present invention shown in FIG. 2.

FIG. 3 is a top plan view showing the interior of the exemplary embodiment of the imaging station/booth 10 of the present invention shown in FIG. 2. Computer hardware and software 50 are contained between front walls 14, 16 and technician computer 28 is mounted on front wall 14. Light boxes 52 containing strobes are positioned between front wall 16 and front panel 40 and cameras 32 mounted on an actuator member 54 are also positioned between front wall 16 and front panel 40 such that cameras 32 can extend through front panel 40 and into the inferior of imaging station/booth 10. Door 24 of side panel 18 functions as a privacy screen for patient disrobing before imaging. Video displays 34, lateral and anterior/posterior handles 56, and upper handle 58 are mounted to frame 30.

Figure 4:
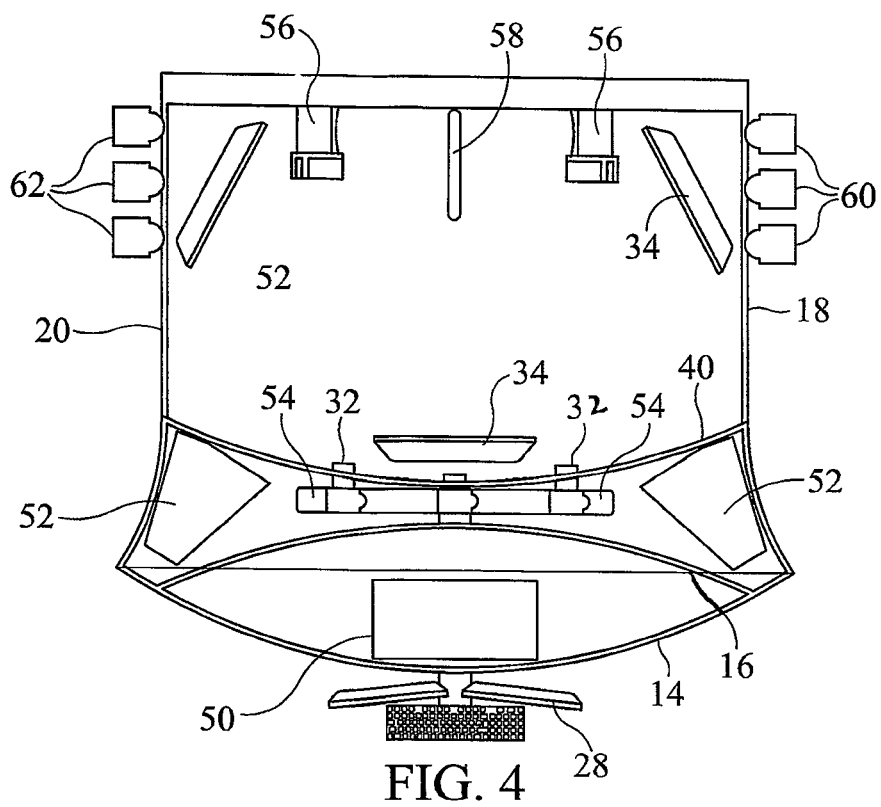
FIG. 4 is a top plan view showing the interior of another exemplary embodiment of the imaging station/booth in accordance with the present invention.

A top plan view showing the interior of another exemplary embodiment of the imaging station/booth 10 in accordance with the present invention is shown in FIG. 4. The exemplary embodiment shown in FIG. 4 is the same as the exemplary embodiment shown in FIG. 3 with the exception of additional cameras. A first set of additional cameras 60 may be mounted to the frame such that they extend through first side wall 18 and/or side panel 46 and a second set of additional cameras 62 may be mounted to the frame such that they extend through second side wall 20. Further, additional cameras may be added to, and vertically mounted on, the actuator member 54 of the original cameras 32 which extend through front panel 40. The more cameras that are used, the shorter the acquisition time for total body imaging. In still another exemplary embodiment the number of cameras positioned within the imaging station/booth may be in the range of 3 to 12 cameras to further reduce the acquisition time for total body imaging. Moreover, it should be noted that any of the cameras may be moved vertically up and down and that additional actuators may also be included as part of the camera assembly later described with reference to FIG. 6 to enable any of the cameras to also move horizontally back and forth.

Figure 5:
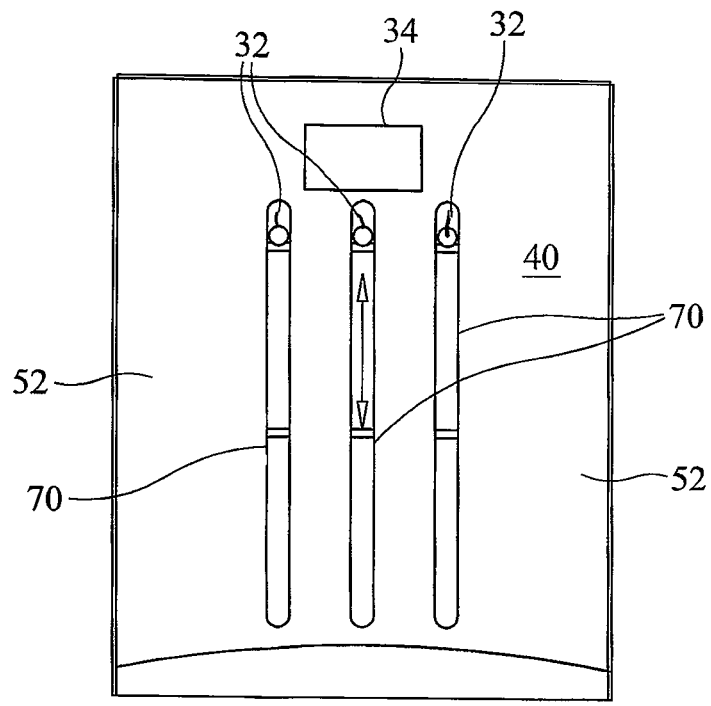
FIG. 5 is a front plan view of the interior front wall of the imaging station/booth of the present invention shown in FIG. 3.
Figure 6:
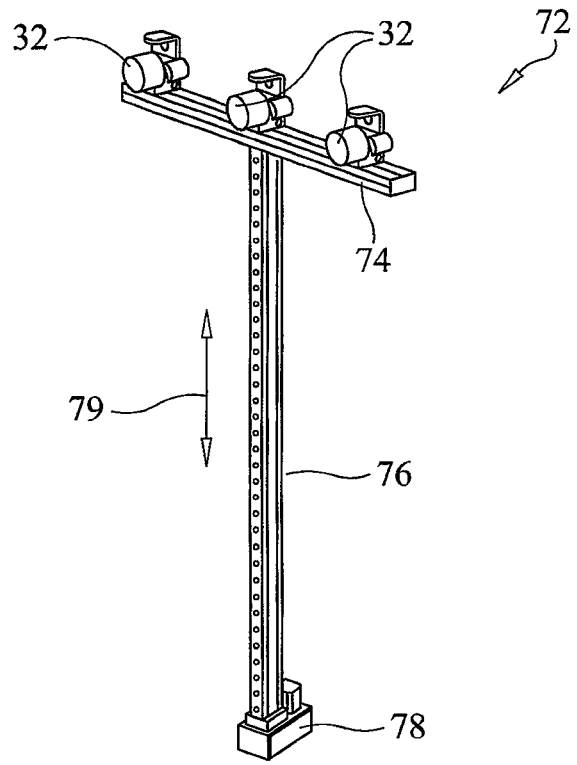
FIG. 6 is a perspective view of an exemplary embodiment of the camera assembly contained within the imaging station/booth of the present invention shown in FIG. 3.

FIG. 5 is a front plan view of the interior front wall of the imaging station/booth 10 of the present invention shown in FIG. 3. Interior front wall or front panel 40 includes a plurality of vertical oblong openings 70 through which cameras 32 mounted on the actuator member extend. The cameras 32 can move up and down through the vertical oblong openings 70 when they are moved by the actuator member. Video display 34 is mounted such that it is located outside of the front panel 40 and within the interior of the imaging station/booth 10 so that a patient within the imaging station/booth 10 can easily view the video display 34. In addition, hidden light boxes 52 (see FIG. 3) containing strobes are located behind the front panel 40. FIG. 6 is a perspective view of an exemplary embodiment of the camera assembly 72 contained within the imaging station booth 10 of the present invention shown in FIG. 3. Camera assembly 72 includes one or more cameras 32 mounted on a horizontal support member 74 which is in turn mounted on a vertical support member 76 that includes an activator 78 such that the horizontal support member 74 can move up and down (arrow 79) relative to the vertical support member 76. The cameras utilized in the automated total body imaging system of the present invention may function to produce two dimensional (2D) imaging and/or three dimensional (3D) imaging. It will be understood by those skilled in the art that numerous variations of the openings in the front panel 40, for both the cameras and the lighting elements/boxes, as well as the camera assembly (including number of cameras, support for the cameras and multi-directional movement of the cameras) can be made to the imaging station/booth 10 for other exemplary embodiments of the invention.

Figure 7:
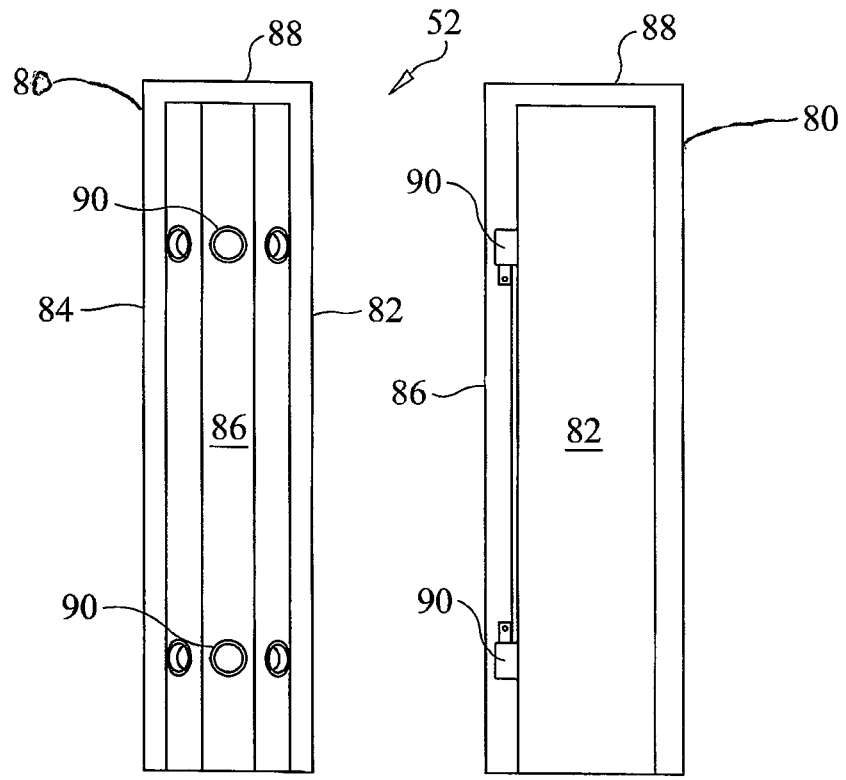
FIG. 7 is a front plan view and a side plan view of an exemplary embodiment of the light boxes contained within the imaging station/booth of the present invention shown in FIG. 3.
Figure 8:
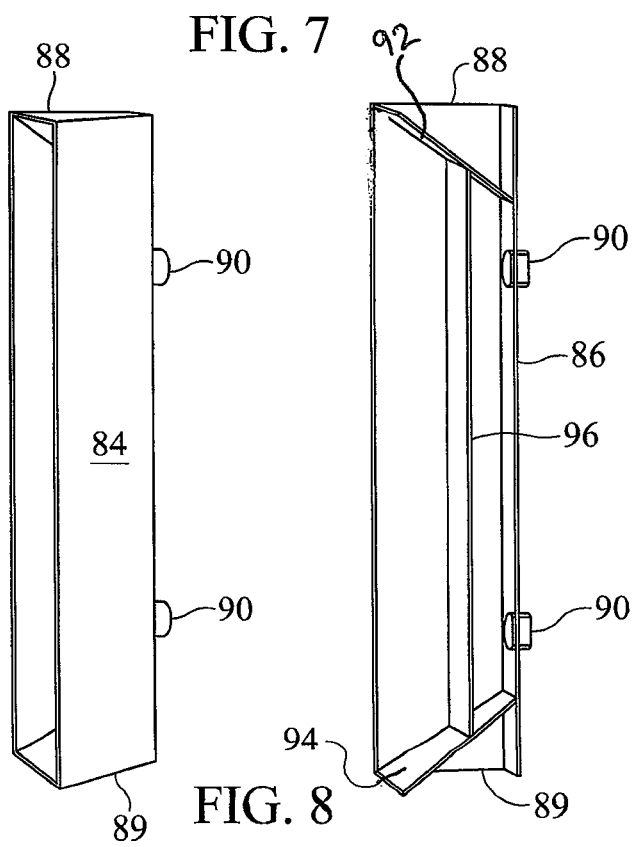
FIG. 8 is a perspective view and a cross-sectional view of the exemplary embodiment of the light boxes shown in FIG. 7.

FIG. 7 is a front plan view and a side plan view of an exemplary embodiment of the light boxes 52 contained within the imaging station/booth of the present invention shown in FIG. 3. Light boxes 52 each include a light box housing 80 which has two opposing sides 82, 84 with a back side 86 located between the two opposing sides 82, 84. Light box housing 80 also includes a top member 88 and a bottom member (89 in FIG. 8) that are each connected to the two opposing sides 82, 84 and the back side 86 to form a housing having an open front side. One or more strobe lights 90 are mounted within the back side 86 such they can extend through the back side 86 and into the light box housing 80. In other exemplary embodiments, the strobe lights may be positioned anywhere within the light box housing 80 and/or within the side, top, bottom, and back panels that make up the light box housing 80. FIG. 8 is a perspective view and a cross-sectional view of the exemplary embodiment of the light boxes 52 shown in FIG. 7. As shown in FIG. 8, each light box housing 80 may further include a top light focusing and/or filtering panel 92, a bottom light focusing and/or filtering panel 94, and a back light focusing and/or filtering panel 96. In one exemplary embodiment, there are two light boxes 52 that are the full height of the imaging station/booth 10 and each light box 52 holds two strobe lights 90. The top light focusing and/or filtering panel 92, the bottom light focusing and/or filtering panel 94, and the back light focusing and/or filtering panel 96 may help further spread the light. The configuration of the two opposing side panels, back panel, top and bottom panels, and the overall curved configuration of the interior of the light boxes 52 further act as diffusing surfaces. The panels which make up the light box housing 80 may be made of polypropylene with reflective lined interiors.

Figure 9:
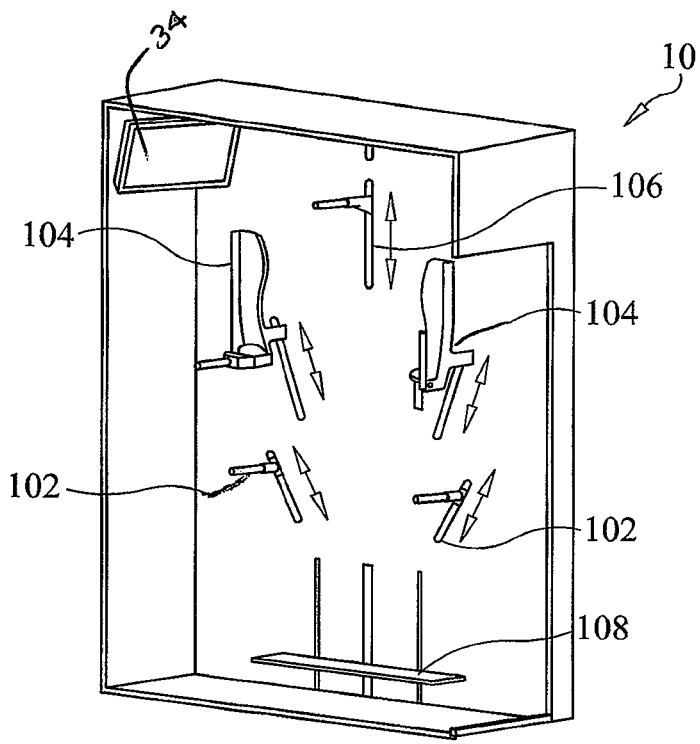
FIG. 9 is a perspective view of the interior rear half and back wall of the imaging station/booth of the present invention shown in FIG. 3.

FIG. 9 is a perspective view of the interior rear half and back wall of the imaging station/booth 10 of the present invention shown in FIG. 3. The interior back wall of the imaging station/booth 10 has several functional components mounted thereon which assist in correctly positioning a patient in order to complete full body imaging of the patient. These include, but are not limited to, two opposing anterior/posterior hands down handles 102, two opposing lateral and anterior/posterior hands up handles 104, an upper handle 106, and a movable and retractable step 108 that can retract into the floor or bottom of the imaging station/booth 10. One or more of the handles or each of the handles may be movable is order to correctly position them to assist the size of a patient. Video displays 34 are also mounted within the imaging station/booth 10.

Figure 10:
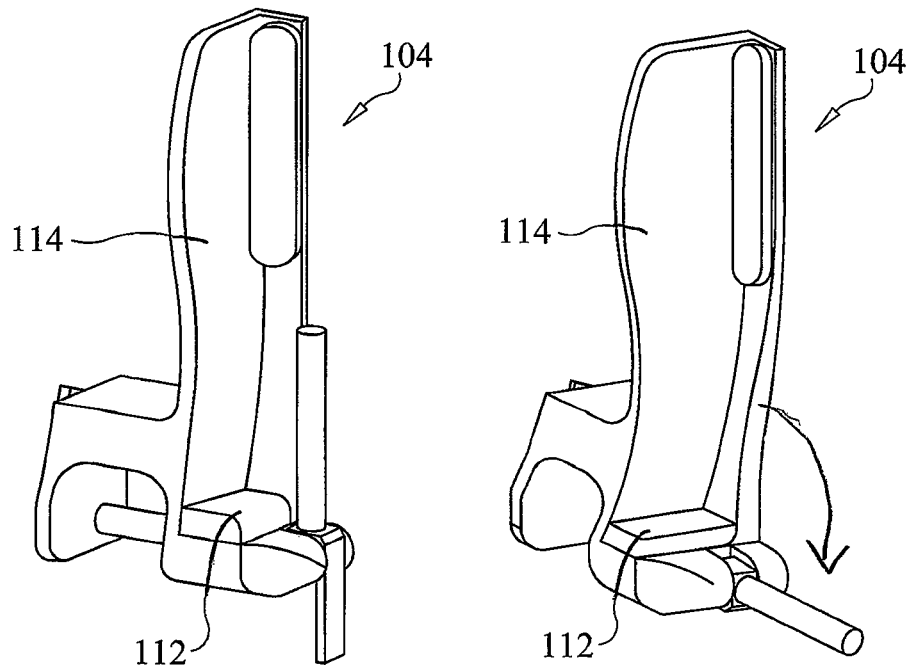
FIG. 10 is a perspective view of an interior handle (and its direction of movement) secured to the back wall of the imaging station/booth of the present invention shown in FIG. 9.

FIG. 10 is a perspective view of an interior handle 104 (and its direction of movement) secured to the back wall of the imaging station/booth of the present invention shown in FIG. 9. As shown in FIG. 10, each of the handles 104 can assist in taking anterior and posterior imaging of a patient's hands and arms by placing the patient's elbows and wrists against the elbow rests 112 and wrist rests 114 of the handles 104. Handles 104 can then assist in taking lateral images of the patient's arms by folding the handles 104 down to create grips for the patient's hands.

Figure 11:
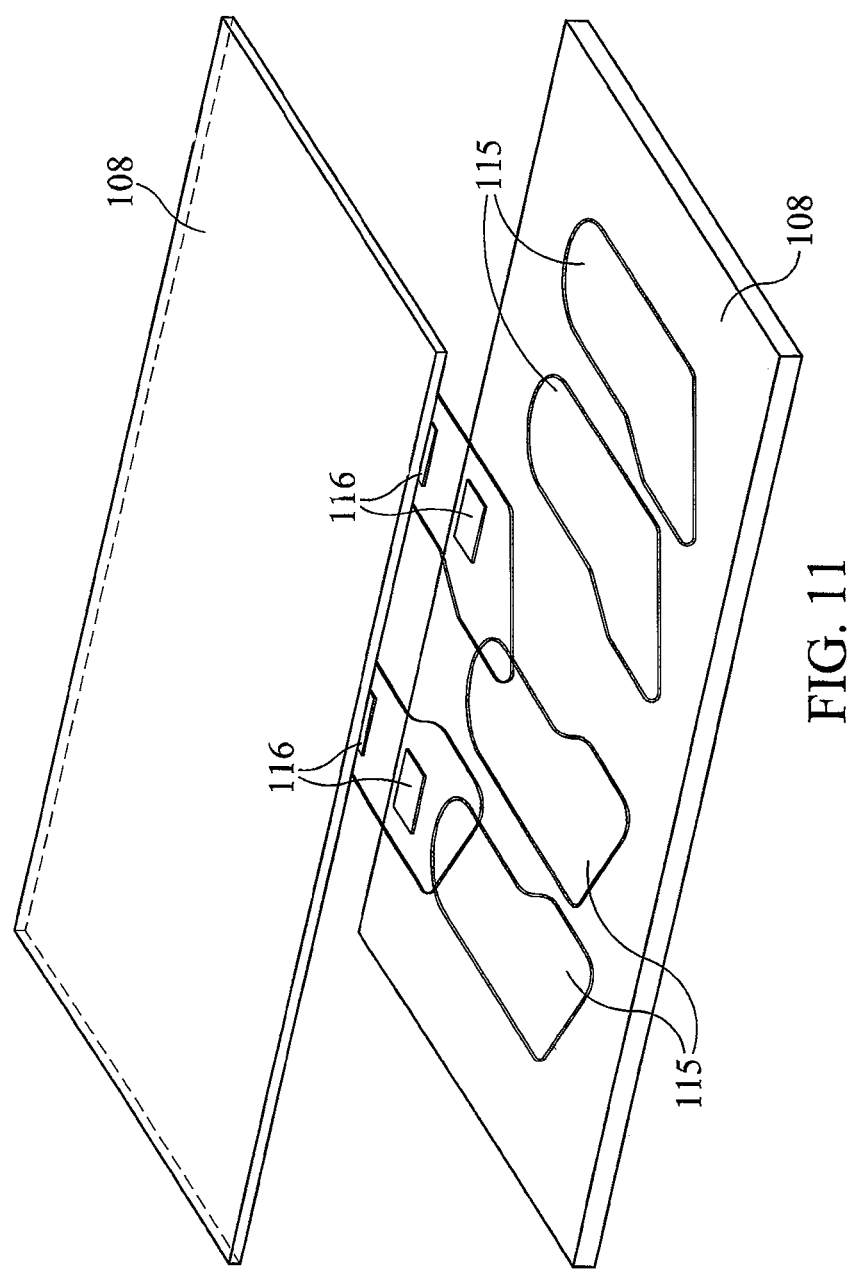
FIG. 11 is an exploded view of an exemplary embodiment of a moveable/retractable step contained within the imaging station/booth of the present invention shown in FIG. 9.
Figure 12:
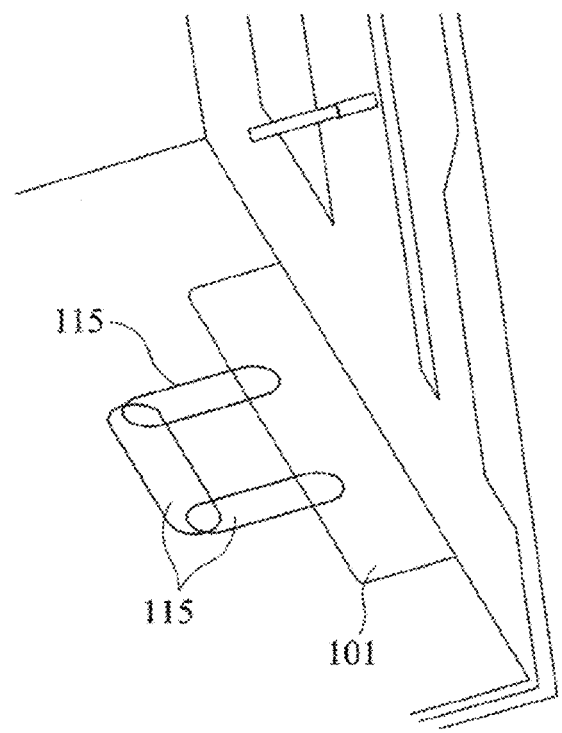
FIG. 12 is a perspective view of a partial rear interior of the imaging station/booth of the present invention shown in FIG. 9 showing the movable/retractable step that is recessed into the floor of the imaging station/booth and an outline for exemplary placement of a user's feet.
Figure 13:
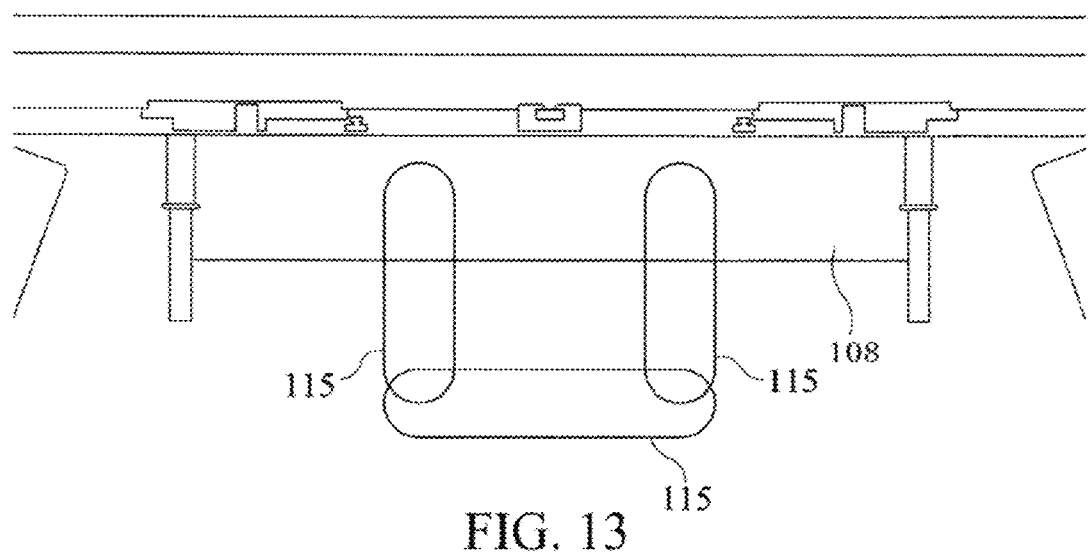
FIG. 13 is a top plan view of the partial rear interior of the imaging station/booth shown in FIG. 12.

FIGS. 11-13 are directed to the movable and retractable step (38, 108) shown in FIGS. 2 and 9. FIG. 11 is an exploded view of an exemplary embodiment of a moveable/retractable step 38, 108 contained within the imaging station/booth 10 of the present invention shown in FIG. 9. FIG. 12 is a perspective view of a partial rear interior of the imaging station/booth 10 of the present invention shown in FIG. 9 showing the movable/retractable step 38, 108 that is recessed into the floor of the imaging station/booth 10 and an outline 115 for exemplary placement of a user's or patient's feet. FIG. 13 is a top plan view of the partial rear interior of the imaging station/booth shown in FIG. 12. The outlined areas 115 for placing a patient's feet have one or more sensors 116 (see FIG. 11) for informing a user or patient that they have correctly or incorrectly positioned their feet.

Figure 14:
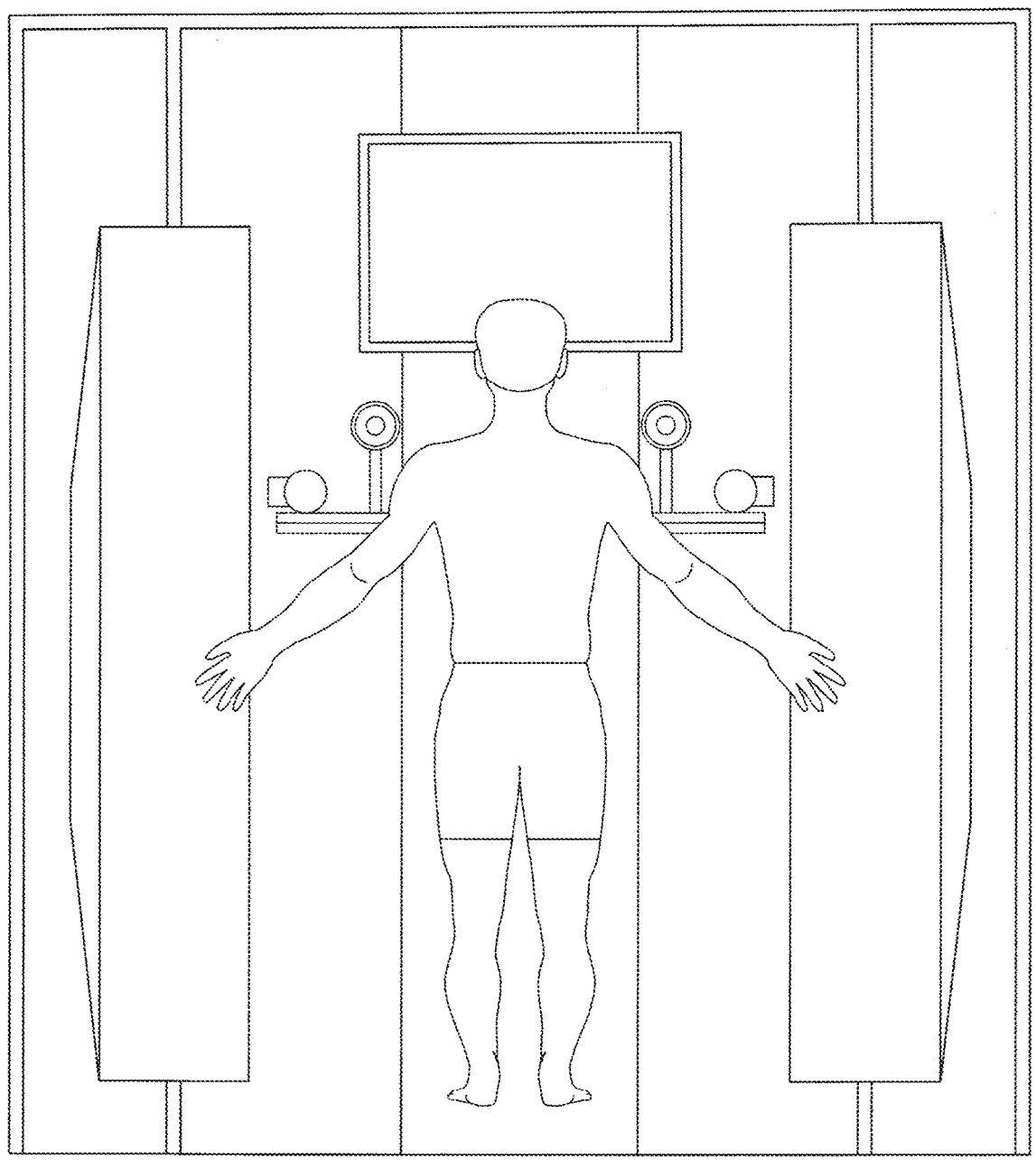
FIG. 14 is a rear plan view (with the back wall removed) showing the interior of the imaging station/booth of the present invention shown in FIG. 9 with a user exhibiting a predetermined pose in front of the cameras contained within the imaging station/booth.
Figure 15:
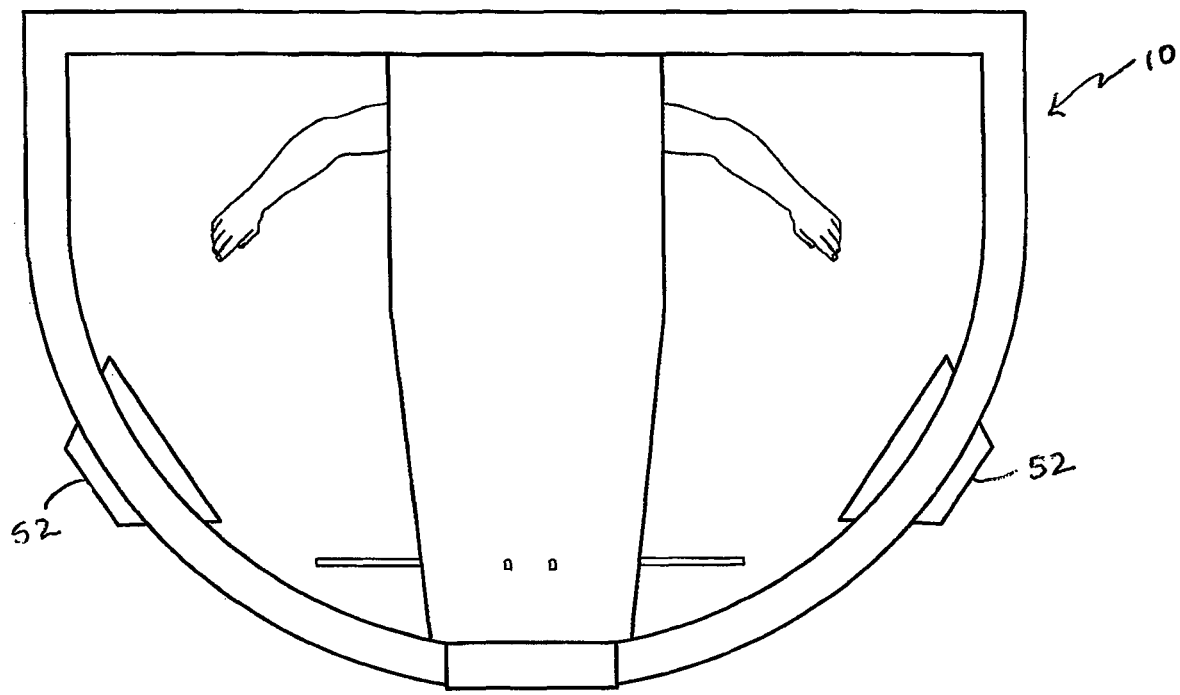
FIG. 15 is a top plan view of the imaging station/booth and the user shown in FIG. 14.
Figure 16:
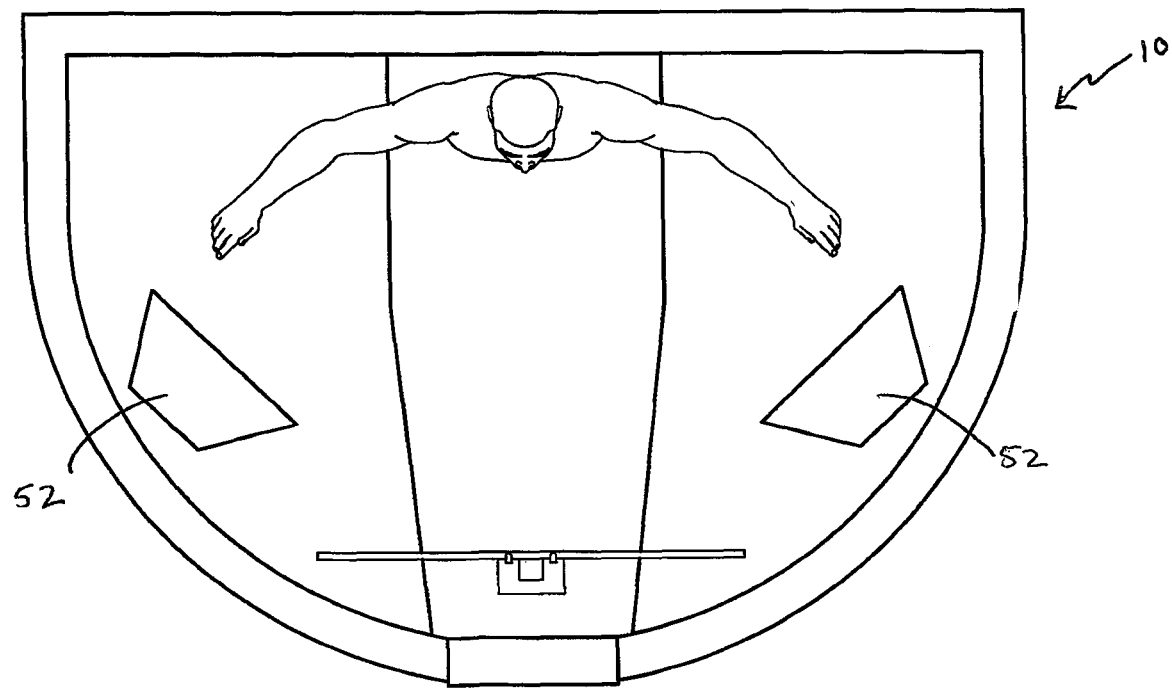
FIG. 16 is a top plan view of another exemplary embodiment of the imaging station/booth and user depicted in FIG. 15.

A rear plan view (with the back wall removed) showing the interior of the imaging station/booth of the present invention shown in FIG. 9 with a user exhibiting a predetermined pose in front of the cameras contained within the imaging station/booth is shown in FIG. 14. FIG. 15 is a top plan view of the imaging station booth and the user shown in FIG. 14. FIG. 16 is a top plan view of another exemplary embodiment of the imaging station/booth and user depicted in FIG. 15. It can be seen that light boxes 52 are inserted through an outer wall of the imaging station/booth 10 in FIG. 15 and that the light boxes 52 are contained within the imaging station/booth 10 in FIG. 16.

Figure 17:
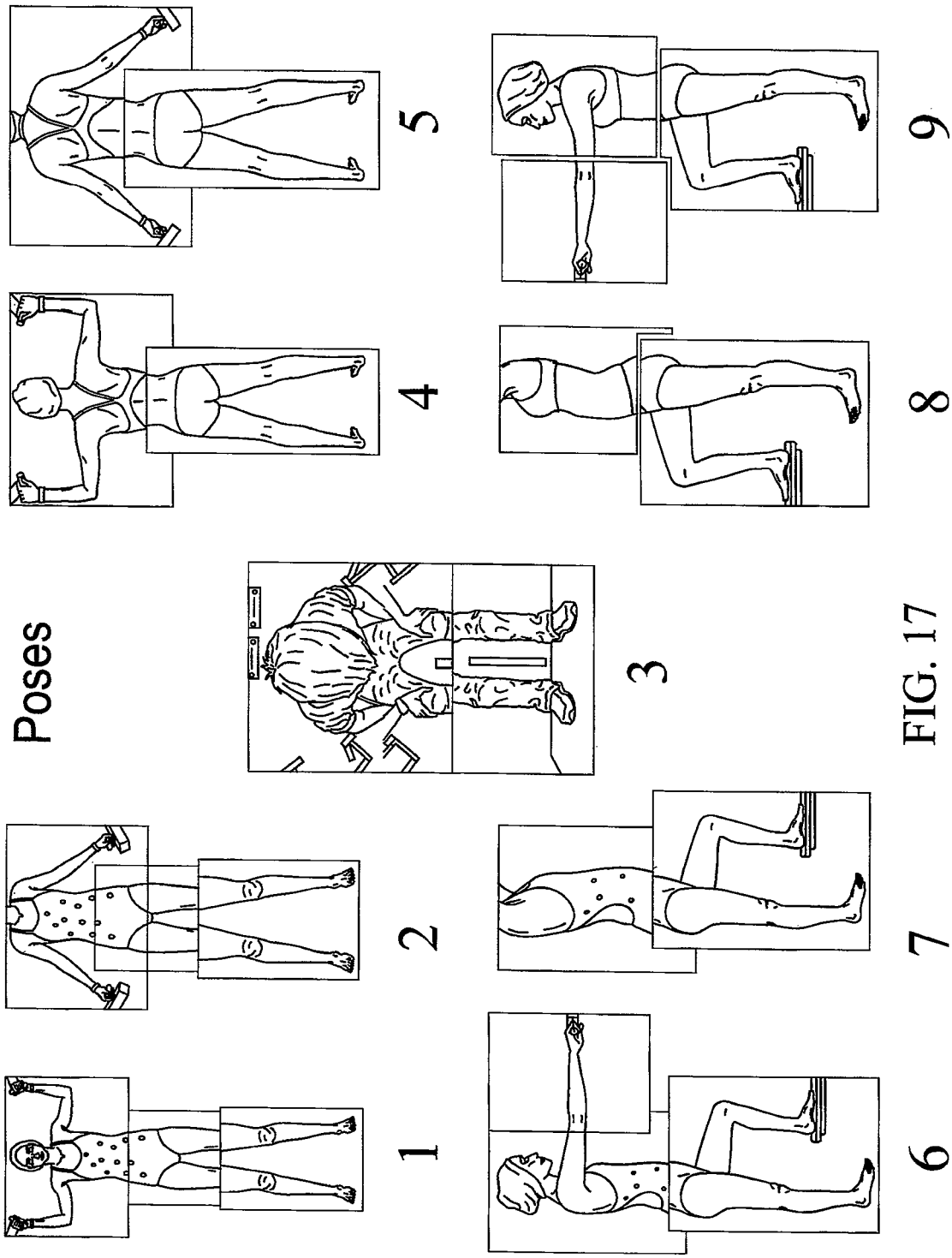
FIG. 17 shows an exemplary predetermined set of body poses for complete body imaging in accordance with the system and apparatus for full body imaging of the present invention.

FIG. 17 shows an exemplary predetermined set of body poses for complete body imaging in accordance with the system and apparatus for full body imaging of the present invention. One exemplary procedure for conducting the total body imaging process using the system and apparatus for automated total body imaging of the present invention may encompass the following exemplary protocol.

The patient is asked to fill out a form before any examination takes place. A consent form explains the procedure and will include the option of leaving clothing on for privacy reasons if the patient so chooses as long as they are aware that documentation of the covered area will not occur. Also on the form, will be the option for either a regional or total body imaging procedure. At this point in time, the patient can be asked to pay up front and out of pocket. The Medical assistant (MA) will call the patient after they are checked in to start the procedure. The MA will get the vitals, body weight, and height. The patient will be given a chart of all the standard poses. While the patient is reviewing the poses, the MA will enter the station/booth and adjust the five handles to the correct positions based on the patient's weight and height, turn on the ambient lights, and start the program. The MA will leave and instruct the patient to undress and hang their clothes on the back of the privacy wall/door. Before entering the imaging station/booth the patient needs to remove all clothing, all jewelry and hair needs to be up and off the face and neck. Once ready, the MA will return, show the patient into the station/booth and start the procedure.

Entering the imaging station/booth.

All the equipment will be on (computer, programs, actuators, cameras, strobes, ambient light, pressure sensors, etc.).

The handles will be in the correct positions and the cameras will be at the top of the actuator waiting for user input.

Welcome to the imaging station/booth (screen talking to the patient). This screen will demonstrate what pose you will need to assume and it will talk you through the positioning required for the poses.

Proper anterior footprints will light up red to highlight the correct position.

Please assume Pose 1 by facing toward the cameras with your feet on the lighted footprints. Toes are pointed straight out front and heel against the back of the footprint.

Once the feet are in the correct position, the lights will turn green via the pressure sensors.

First we will photograph the front of your body. Please raise your hands up so that your elbows form 90-degree angles and the back of your hand is pressed against the pad. Keep your hands open with your palms facing the cameras. The first pose is like a stick up pose. Please stand up straight, remain still and keep your head straight and looking forward at the target. When the cameras take a picture, there will be a big flash. Please close your eyes when the time conies. The cameras will take pictures in 3, 2, 1. Please continue to stand still. The cameras will take pictures in 3, 2, 1 (This will be repeated for 4 more times).

Once the patient is in the correct position, the sensors will relay information to the Medical Assistant and they will commence the sequence. The cameras will take pictures of the body moving from top to bottom. They will take pictures at 6 different vertical positions.

Assume Pose 2. You will have to drop your arms and grab a hold of the lighted band bars near your hips with both hands. Please stand up straight, remain still and keep your head straight looking forward. When the cameras take a picture, there will be a big flash. Please close your eyes when the time comes. The cameras will take pictures in 3, 2, 1. Please continue to stand still. The cameras will take pictures in 3, 2, 1 (This will be repeated for 4 more times). The handles will be illuminated red and then turn green when in the correct position. Once the patient is in the correct position, the sensors will relay information to the Medical Assistant and they will commence the sequence. The cameras will take pictures of the body moving from bottom to top. They will take pictures at 6 different vertical positions.

Assume Pose 3. Continue to stand toward the camera with your feet in the illuminated positions. Please lean over and place your hands on your legs just above your knee. Stare at the ground. Once the patient is in the correct position, the sensors will relay information to the Medical Assistant and they will commence the sequence. The cameras will take pictures of the body moving from top to bottom. They will take pictures at 6 different vertical positions.

Assume Pose 4. Turn around and face the back wall of the imaging station. Place your feet to the lighted footprints on the floor. Toes are pointed straight out front and heel against the back of the footprint. Please raise your hands up so that your elbows form 90-degree angles and the palm of your hand is pressed against the pad. Keep your hands open with the back of your hand facing the cameras. Stand up straight, remain still and keep your head straight looking forward. When the cameras take a picture, there will be a big flash. Please close your eyes when the time comes. The cameras will take pictures in 3, 2, 1. Please continue to stand still. The cameras will take pictures in 3, 2, 1 (This will be repeated for 4 more times). Once the patient is in the correct position, the sensors will relay information to the Medical Assistant and they will commence the sequence. The cameras will take pictures of the body moving from bottom to top. They will take pictures at 6 different vertical positions.

Assume Pose 5. Lower your hands and grab the lower lighted hand bars near your hips. Please stand up straight, remain still and keep your head straight looking forward. The handles will be illuminated red and then turn green when in the correct position. Once the patient is in the correct position, the sensors will relay information to the Medical Assistant and they will commence the sequence. The cameras will take pictures of the body moving from top to bottom. They will take pictures at 6 different vertical positions.

Please step away from the back wall and wait to be prompted. A step will be raised to aid you in the next pose. Once the patient is away from the step, the MA will hit a button to move the step to the correct position. Assume Pose 6. The next pose you will turn so that your right side feces the cameras. Grab the lighted hand bar in front of you with your right hand. This set of pictures will capture the right side. Please keep your right arm out straight to the bar, lock your elbow while holding on to the bar. Align your left arm along the left side of your body to hide it from the cameras. Next raise your left leg onto the platform so the camera can take pictures of your left inner leg. Keep the right leg in the designated footprint on the floor. The left knee needs to be at a 90-degree angle or like an L shape. Please stand up straight, remain still and keep your head straight looking forward and keep your shoulders straight. The handles and footprint will be illuminated red and then turn green when in the correct position. Once the patient is in the correct position, the sensors will relay information to the Medical Assistant and they will commence the sequence. The cameras will take pictures of the body moving from bottom to top. They will take pictures at 6 different vertical positions.

Assume Pose 7. The only part that changes from the previous pose is the location for your right arm. Raise your right hand to hold onto the bar above your head. This picture will take photos of your right armpit and right side and neck. Please stand up straight, remain still and keep your bead straight looking forward. The handles and footprint will be illuminated red and then turn green when in the correct position. Once the patient is in the correct position, the sensors will relay information to the Medical Assistant and they will commence the sequence. The cameras will take pictures of the body moving from top to bottom. They will take pictures at 6 different vertical positions.

You may drop your arm and relax.

The next pose will be Pose 8.

Please assume Pose 8. Turn to your body so that the left side is lacing the cameras. Grab the lighted hand bar in front of you with your left-hand. This set of pictures will capture your left side. Please keep your left arm out straight to the bar, lock your elbow while holding on to the bar. Align your right arm along the right side of your body to hide it from the cameras. Next raise your right leg onto the platform so the camera can take pictures of your right inner leg. Keep the left leg in the designated footprint on the floor. The right knee needs to be at a 90-degree angle or like an L shape. Please stand up straight, remain still and keep your head straight looking forward and keep your shoulders straight. The handles and footprint will be illuminated red and then turn green when in the correct position. Once the patient is in the correct position, the sensors will relay information to the Medical Assistant and they will commence the sequence. The cameras will take pictures of the body moving from bottom to top. They will take pictures at 6 different vertical positions.

Assume Pose 9. The only part that changes from the previous pose is the location for your left arm. Raise your left hand to hold onto the bar above your head. This picture will take photos of your left armpit and left side and neck. Please stand up straight, remain still and keep your head straight looking forward. The handles and footprint will be illuminated red and then turn green when in the correct position. Once the patient is in the correct position, the sensors will relay information to the Medical Assistant and they will commence the sequence. The cameras will take pictures of the body moving iron top to bottom. They will lake pictures at 6 different vertical positions.

Please step away from the back wall. The step will move back into the floor. The step is commanded to recess back into the floor.

This completes your total body imaging session. Please watch for protruding handles and bars as you exit. You may change into your clothes and wait for the doctor. Thank you.

The Medical assistant will wait for the patient to dress. Then they will wipe down the inside of the station/booth and ready for the next patient.

Figure 18:
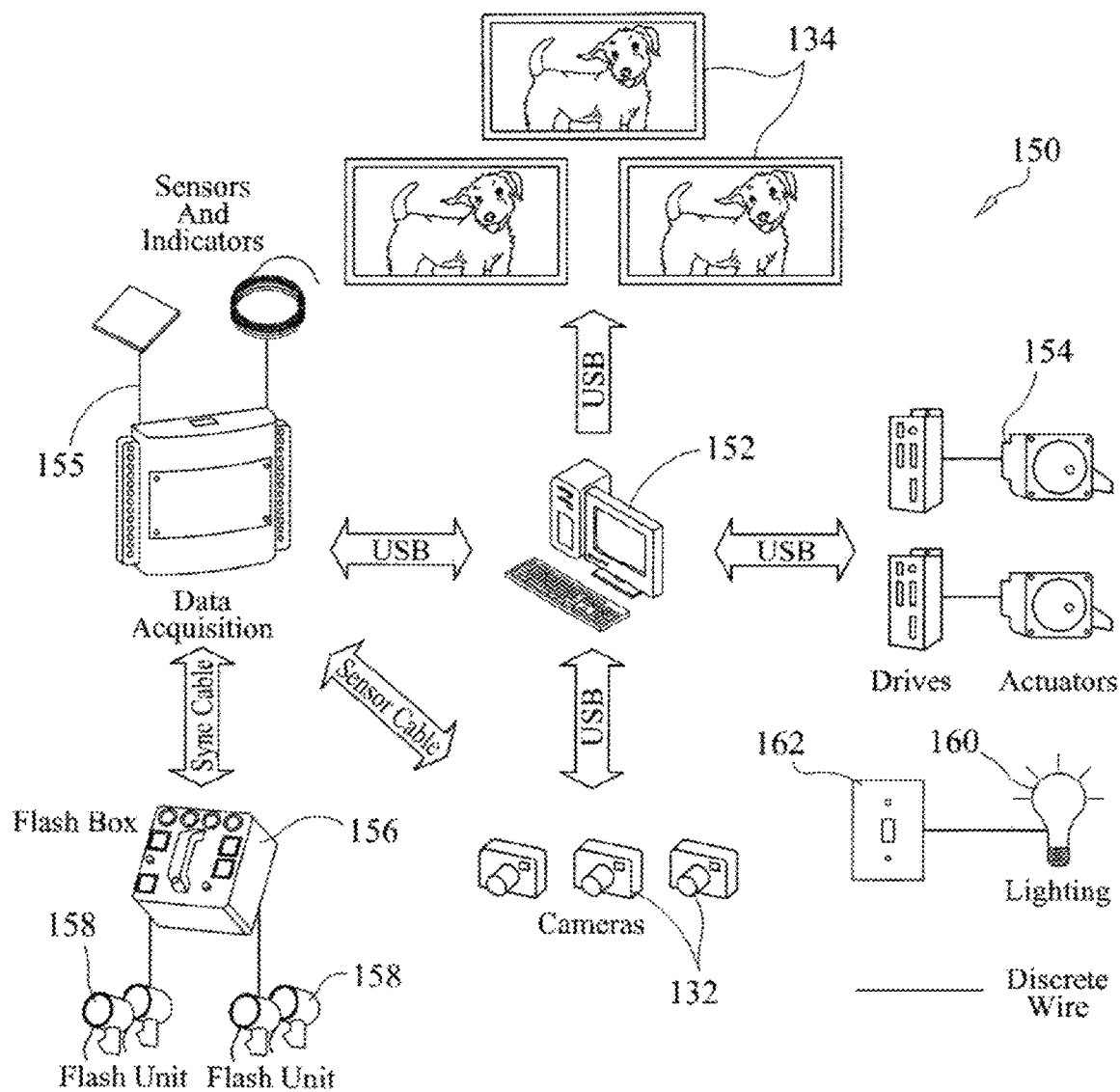
FIG. 18 shows a schematic of an exemplary imaging station/booth architecture in accordance with the present invention.
Figure 19:
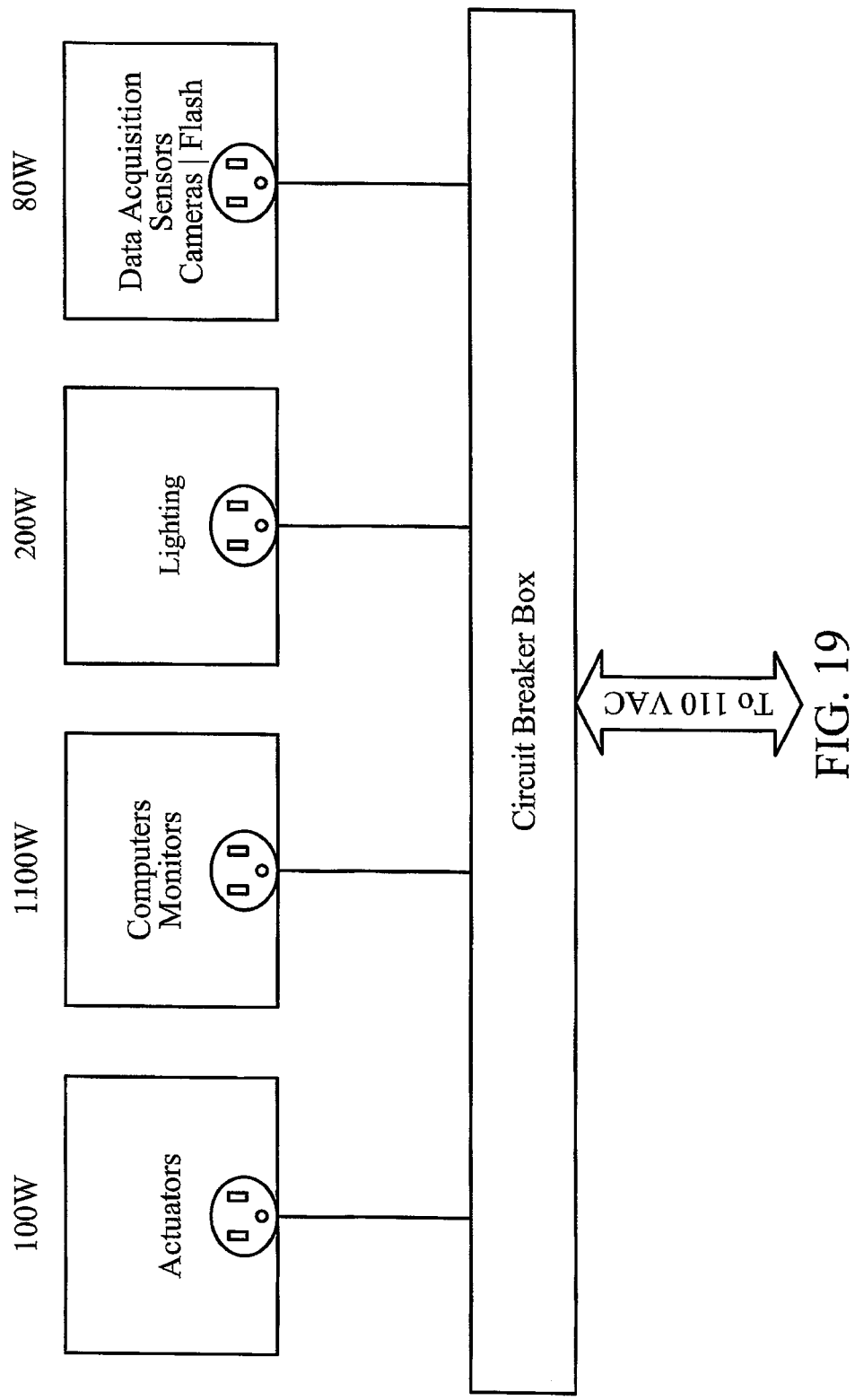
FIG. 19 shows a schematic of an exemplary electrical power architecture for the electrical components of the imaging station/booth in accordance with the present invention.

FIG. 18 shows a schematic of an exemplary imaging station/booth architecture 150 in accordance with the present invention. Imaging station/booth architecture 150 shows the various exemplary connections between a computing device 152 and/or user interface for a technician or medical assistant and video displays 134 viewed by a user/patient, the cameras 132, the actuators and drives 154 that move the cameras 132, the sensors and indicators 155 that may be connected to the handle members and movable step which can in turn be connected to a flash box 156 that controls flash units 158 within the light boxes. Main lighting 160 (other than the lighting associated with the lighting boxes and/or lighting for cameras) within the station/booth may be connected to a switch 162. FIG. 19 shows a schematic of an exemplary electrical power architecture for the electrical components of the imaging station/booth in accordance with the present in invention.

Figure 20:
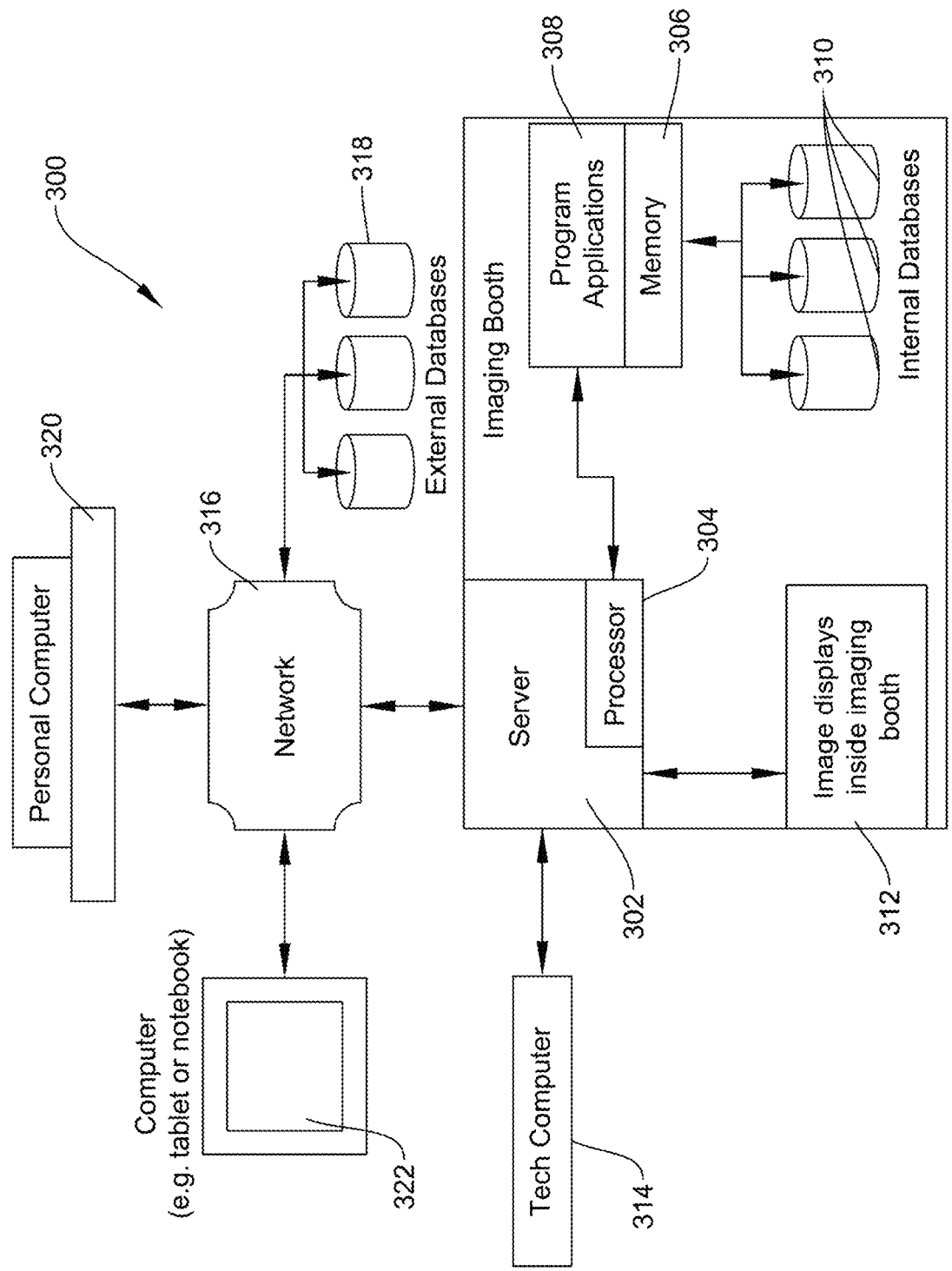
FIG. 20 is a block diagram showing an exemplary embodiment of the system for full body imaging of the present invention.

FIG. 20 is a block diagram showing an exemplary embodiment of the system 300 for full body imaging of the present invention. System 300 may include a server 302 having a processor 304 which is in communication with a memory 306 having one or more program applications 308 stored therein such as, for example, a Body Imaging Program which controls the movement and function of the cameras in the imaging station/booth and the instructions to the user or patient and an Audio and Visual Program that provides verbal and video instructions and posing guides to the patient in order to demonstrate the correct poses to the patient. Memory 306 may also be in communication with internal databases 310 that can include, but are not limited to, parameters and standards for assessing skin neoplasms and/or skin variations and/or previous images taken of the patient for comparison to current images. The server 302 may also be in communication with the image/video displays 312 that are positioned and mounted within the interior of the imaging station/booth. Server 302 may also be in communication with a computer 314 that is for the technician or medical assistant so that the technician or medical assistant can intervene if necessary to control certain portions of the program applications or to make necessary selections required by the program applications. The server 302, processor 304, memory 306, program applications 308, internal databases 310, and image/video displays or monitors 312 may all constitute hardware and/or software that is located within a portion of the imaging station/booth. The server 302 may further be in communication with a network 316 that can access external databases 318 which may also include, but are not limited to, parameters and standards for assessing skin neoplasms and/or skin variations and/or previous images taken of the patient for comparison to current images for any number of the previous described applications for the automated total body imaging system of the present invention. In addition, it should be understood that the total body imaging system of the present invention can easily interface with any type of electronic medical record (EMR) systems. Server 302 can also provide access to the program applications as well as information and data produced from the program applications to personal computers 320 and personal notebooks and/or tablets 322 of physicians or medical providers via network 316 so that physicians and/or medical providers who are responsible for viewing and assessing the total body images do not have to be present at the imaging station or imaging station/booth while imaging is taking place.

Figure 21:
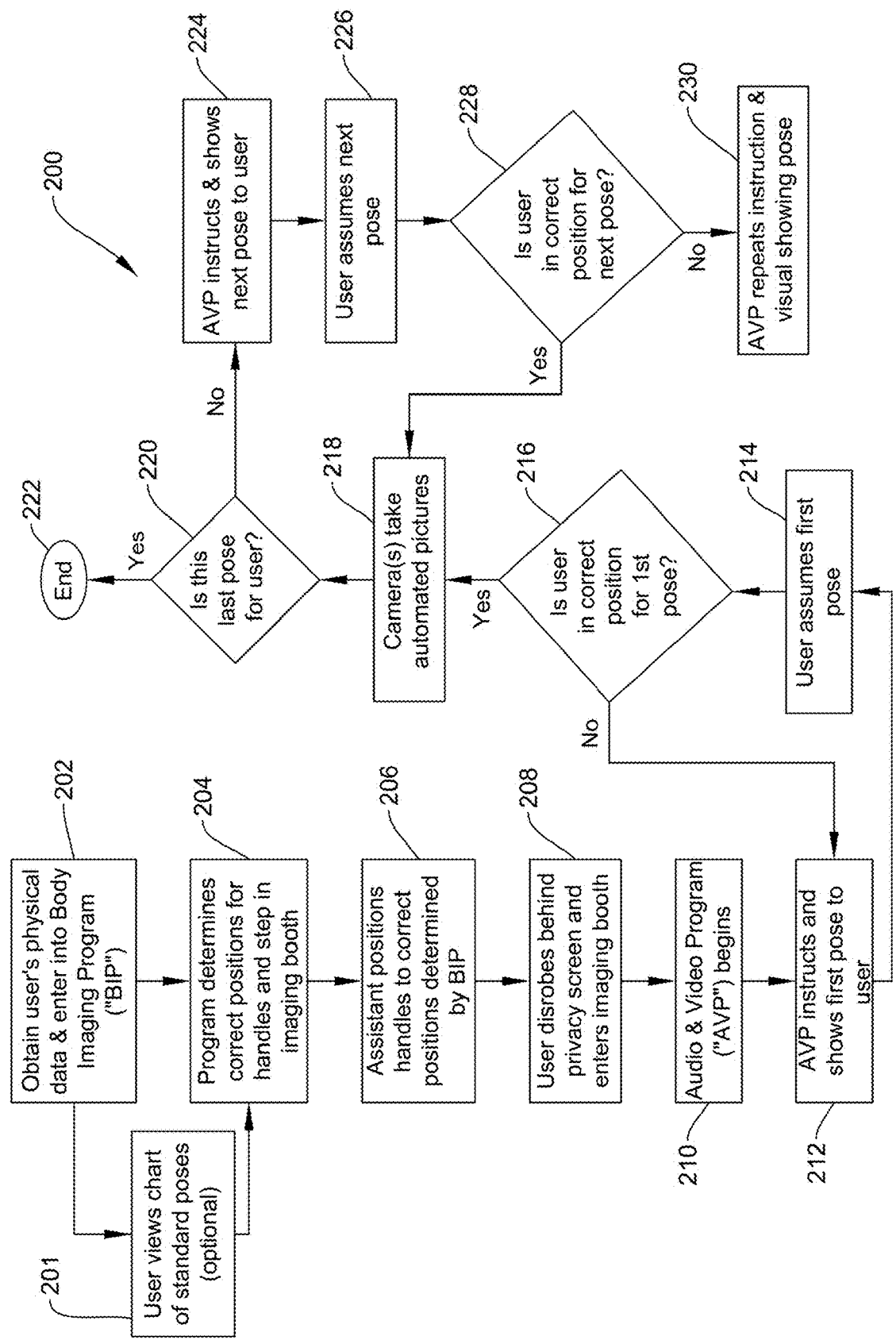
FIG. 21 is a flowchart showing an exemplary embodiment of a method for automated total body imaging in accordance with the present invention.

FIG. 21 is a flowchart showing an exemplary embodiment of a method for automated total body imaging 200 in accordance with the present invention. The automated total body imaging system of the present invention may include two dimensional (2D) imaging and/or three dimensional (3D) imaging. In the exemplary method for total body imaging 200, a user/patient's physical data is obtained and entered into a body imaging program (BIP) associated with the system 300 by a technician/medical assistant in step 202 and the BIP determines the correct positions for the handles and step contained within the imaging station/booth in step 204. In optional step 201, a user/patient may view a chart of standard poses that they will undertake in the imaging station/booth. In step 206, the technician/medical assistant positions the handles in the imaging station/booth to the correct positions determined by the BIP. The user/patient then disrobes behind a privacy screen or door of the imaging station/booth and enters the imaging station/booth in step 208. The audio and video program (AVP) shown and heard within the imaging station/booth then begins in step 210 and the AVP instructs and shows the first pose to the user/patient in step 212. The user/patient then assumes the first pose in step 214 and the total body imaging system determines if the user/patient is in the correct position for the first pose in step 216. If the user/patient has posed correctly, the cameras within the imaging station/booth take automated pictures of the user/patient in that position in step 218. If the user/patient has not posed correctly, the AVP instructs and shows the user/patient the first pose again as in step 212. Once the cameras take automated pictures in step 218, the system queries whether this is the last pose for the user in step 220. A technician/medical assistant may preprogram and/or pre select a program option wherein the user/patient is instructed to undertake all or some of the poses shown in FIG. 17. If this is the last pose for the user/patient, the AVP ends in step 222 and the user/patient is instructed that the session is over and that they can exit the station/booth and dress. If this is not the last pose for the user/patient, the AVP instructs and shows the next pose to the user/patient in step 224 and the user/patient assumes the next pose in step 226. The total body imaging system then determines if the user/patient is in the correct position for the nest pose in step 228. If the user/patient has posed correctly, the cameras within the imaging station/booth take automated pictures of the user/patient in that position in step 218. If the user/patient has not posed correctly, the AVP instructs and shows the user/patient the same pose again in step 230. Once the cameras take the automated pictures in step 218, the system queries whether this is the last pose for the user in step 220. If this is the last pose for the user/patient, the AVP ends in step 222 and the user/patient is instructed that the session is over and that they can exit the station/booth and dress. If this is not the last pose for the user/patient, the AVP instructs and shows the next pose to the user/patient in step 224 and the user/patient assumes the next nose in step 226. This process then repeats itself until all of the poses are correctly performed by the user/patient and pictures of all of those poses are obtained.

Figure 22:
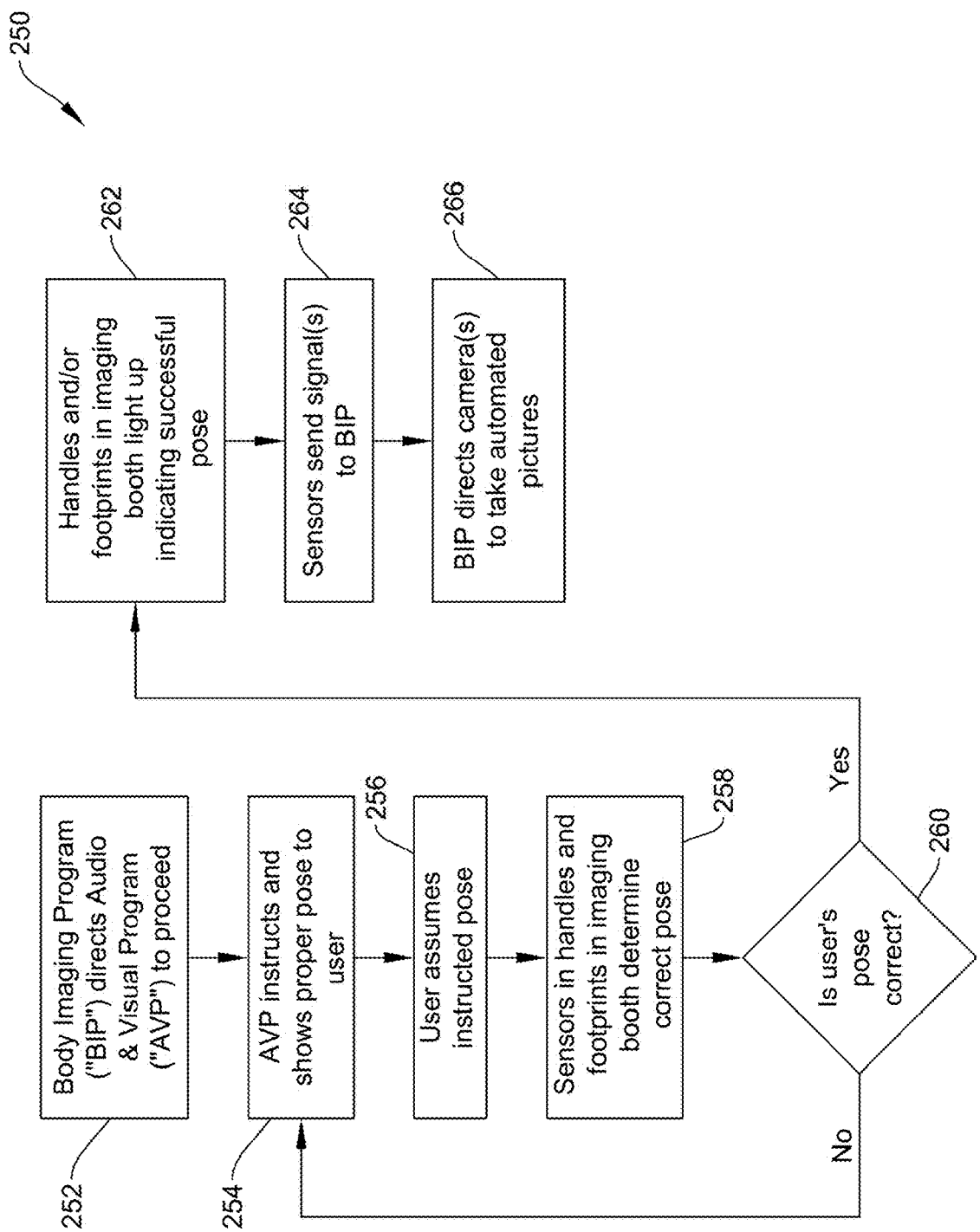
FIG. 22 is a flowchart showing an exemplary method for determining a user's correct position for predetermined poses in accordance with the method shown in FIG. 21.

FIG. 22 is a flowchart showing an exemplary method for determining a user's correct position for predetermined poses 250 in accordance with the method shown in FIG. 21. As previously explained with reference to FIG. 21, the BIP directs the AVP to proceed in step 252. The AVP instructs and shows the proper pose to the user/patient in step 254 and the user/patient assumes the instructed pose in step 256. Sensors, such as touch sensors, in handles and footprints and/or the footplate contained within the imaging station/booth determine when the correct pose is assumed in step 258. The system then queries whether the user/patient's pose is correct in step 260 and if the pose is correct, the handles and/or footprints and/or footplate within the imaging station/booth light up indicating a successful pose in step 262. If the pose is not correct, it goes back to step 254 and the AVP instructs and shows the proper pose to the user/patient again. When the pose is correct and the handles and/or footprints and/or foot plate light up in the imaging station/booth in step 262, the sensors send a signal to the BIP in step 264 and the BIP directs the cameras to takes automated pictures in step 266. It should be noted that a user/patient's correct position may also be determined by the technician/medical assistant viewing the user/patient's nose on an image display device located outside the imaging station/booth and the technician/medical assistant may indicate the correct pose by touching a button on the imaging display device which may also be a touch screen.

Figure 23:
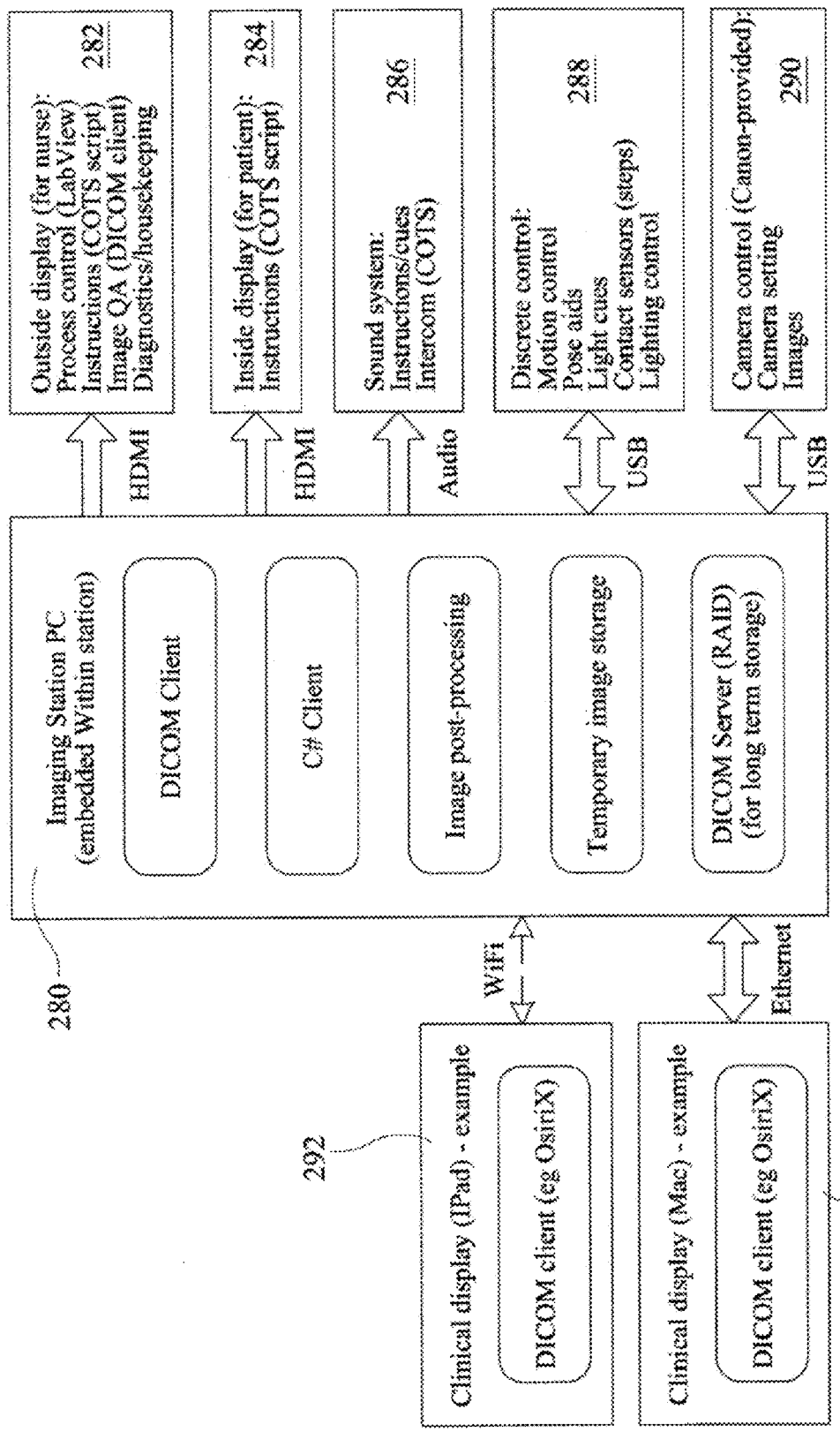
FIG. 23 is an exemplary software block diagram showing connections with the imaging station/booth computer in accordance with the present invention.
Figure 24:
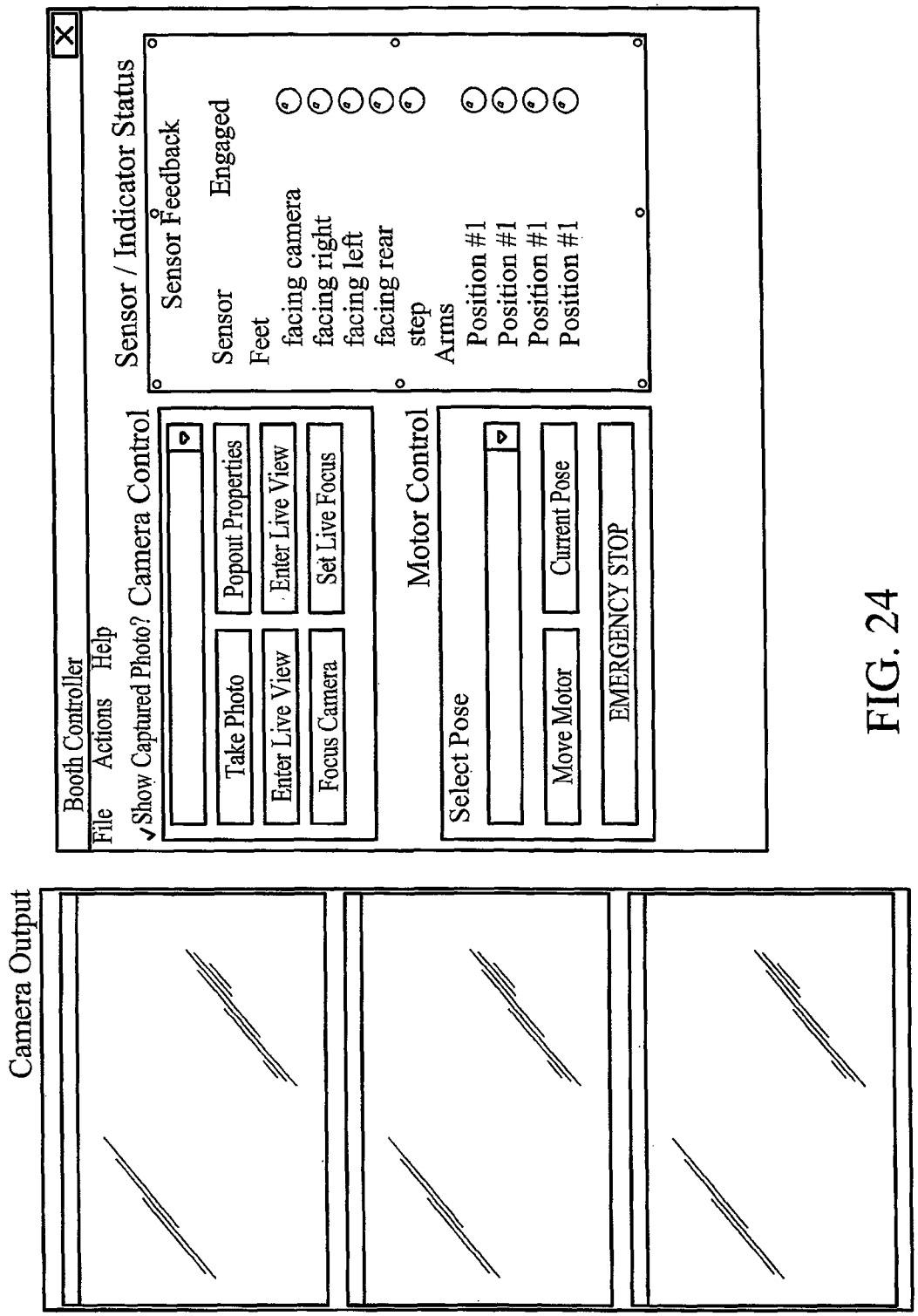
FIG. 24 is an exemplary screen shot of the graphical user interface that can be seen by a technician when the technician is assisting in the automated full body imaging system and apparatus of the present invention.

FIG. 23 is an exemplary software block diagram showing connections between the computer processing unit for the imaging station/station/booth (or imaging station personal computer embedded within the imaging station/station/booth) 280 and the outside display/interface or technician/medical provider screen/computer 282, the inside video screens/displays 284, the sound system/audio/speaker components 286, the controls 288 for motion, posing aids, light cues, contact sensors and lighting control, and the cameras 290 including cameras settings and images. The computer processing unit 280 for the imaging station/booth may also be connected to a notebook or tablet 292 of a medical provider or medical facility, such as an IPad for example, via a WiFi connection and/or a wired connection to show user/patient images and data obtained with the imaging station/booth. In addition, the computer processing unit 280 for the imaging station/booth may also be connected to a personal computer 294 of a medical provider or medical facility, such as a Mac for example, via an Ethernet connection to show user/patient images and data obtained with the imaging station/booth. FIG. 24 is an exemplary screen shot of the graphical user interlace that can be seen by a technician/medical assistant when the technician/medical assistant is assisting in the automated full body imaging system and apparatus of the present invention.

Figure 25:
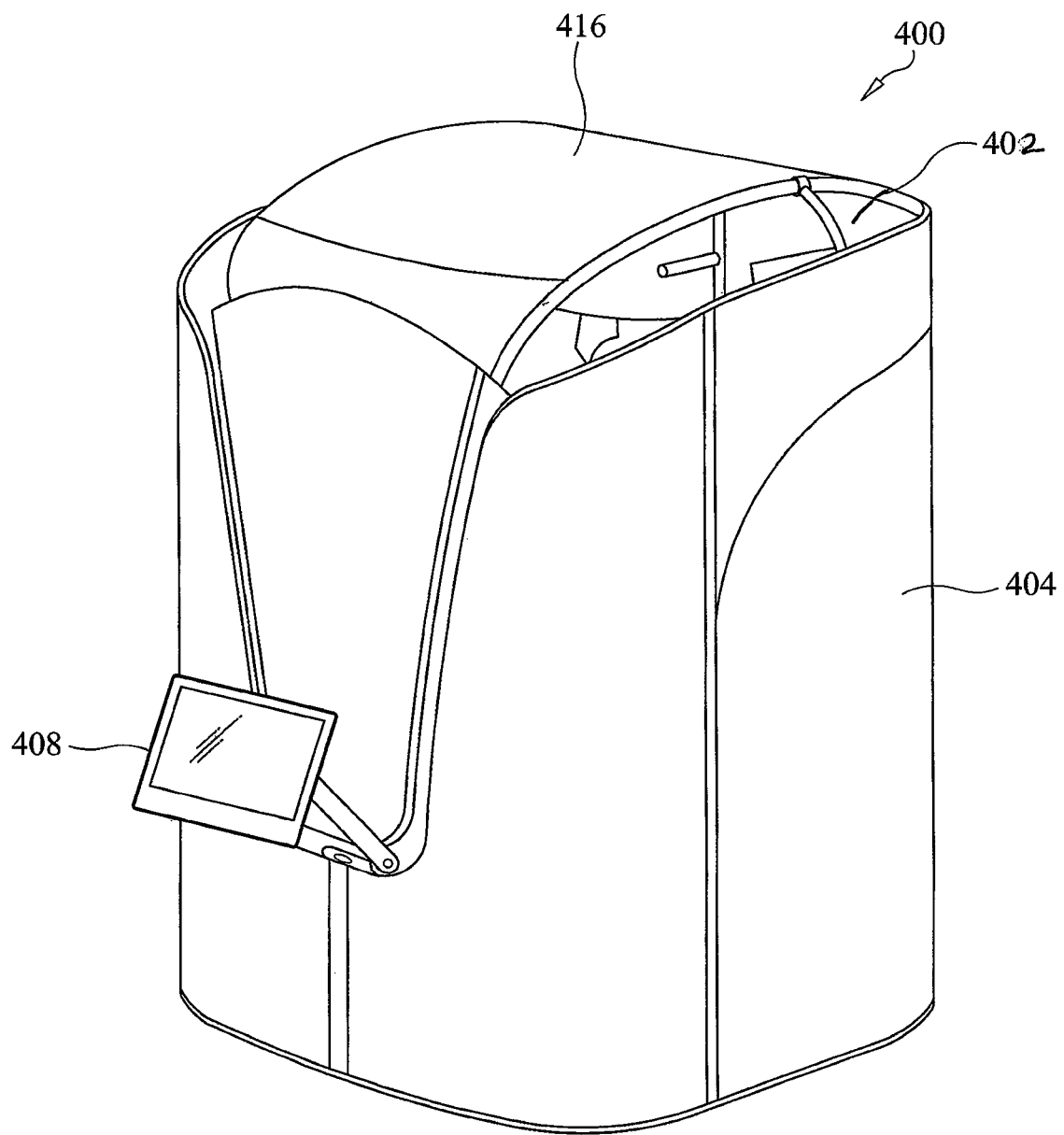
FIG. 25 is an outer perspective view of another exemplary embodiment of the imaging station/booth in accordance with the present invention.

FIG. 25 shows an outer perspective view of another exemplary embodiment of the imaging station/booth 400 in accordance with the present invention. Imaging station/booth 400 includes an enclosed interior area 402, a door 404 enabling a user of the imaging station/booth to enter the enclosed interior area, and a plurality of cameras (see FIG. 26) which together provide overlapping images of the user in one or more predetermined poses where the plurality of cameras exist in stationary positions and are not capable of repositioning. The imaging station/booth 400 also includes a technician computer device 408 that may be adjustably connected to an outer surface of the imaging station/booth 400 to enable a technician to control the program applications associated with the use of the imaging station/booth 400. The imaging station/booth 400 has a curved roof to create an open feeling for those users having their images taken within the enclosed interior area 402. It should be noted that the enclosed interior area 402 may be an area that is fully enclosed or an area that is mostly fully enclosed as exhibited in the imaging station/booth 400 shown in FIG. 25.

Figure 26:
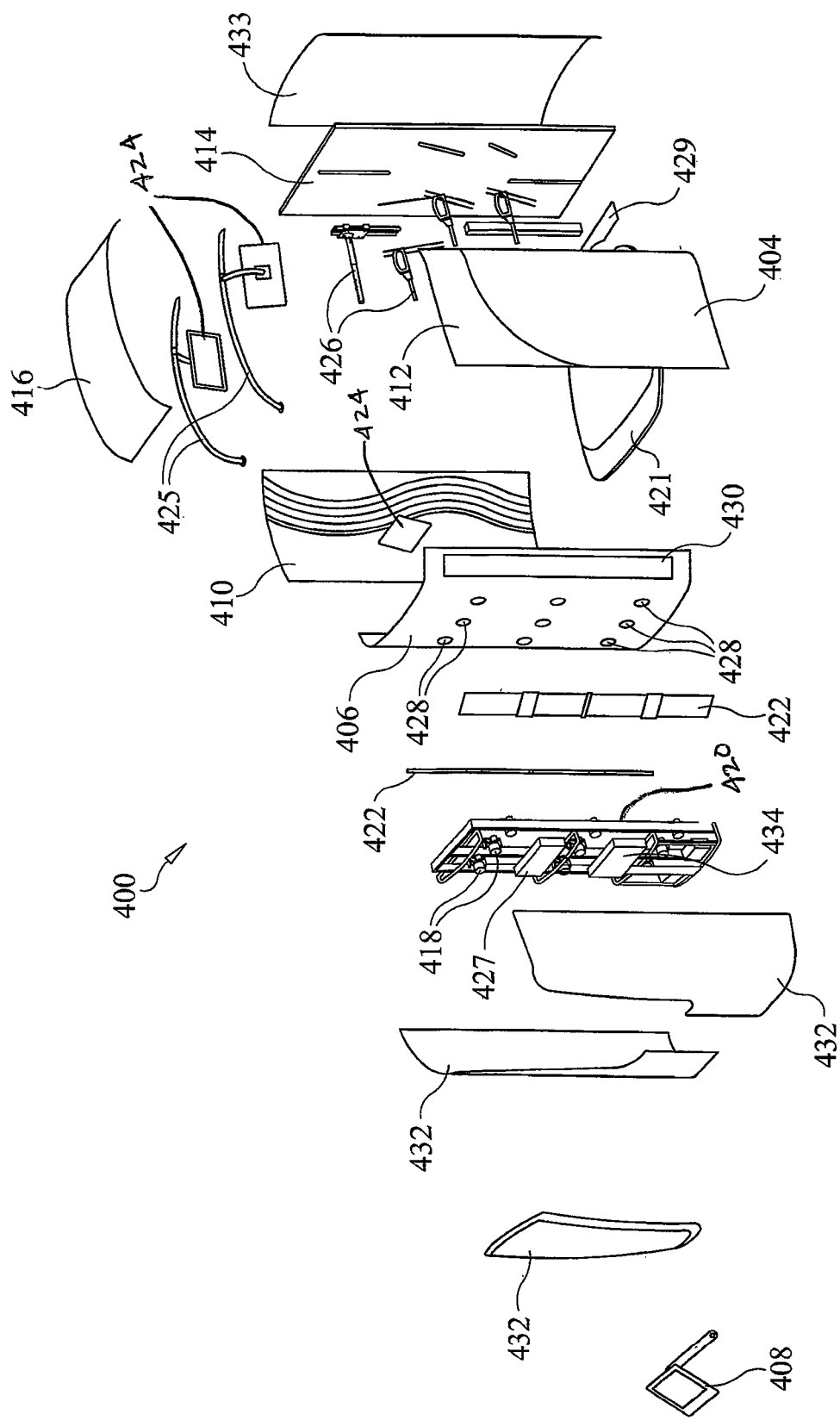
FIG. 26 is an exploded view of the exemplary embodiment of the imaging station/booth of the present invention shown in FIG. 25.

FIG. 26 is an exploded view of the exemplary embodiment of the imaging station/booth 400 of the present invention shown in FIG. 25. As shown in FIG. 25, imaging station/booth 400 includes a front panel 406, two opposing side panels 410, 412 a rear panel 414, and a top cover member 416. The door 404 may be located within side panel 412 or entire side panel 412 may function as door 404.

Furthermore, although not shown, both side panels 410, 412 may function as doors or include doors. Imaging station/booth 400 also includes a plurality of cameras 418 that are secured to a frame 420, a floor member 421, one or more light panels 422, one or more visual display devices 424, one or more body positioning members 426,429, and at least one speaker component 427. The speaker component 427 enables a user to hear voice instructions within the enclosed interior area 402 and the visual display device(s) 424 are located within the enclosed interior area 402 such that they are viewable by a user. This enables a user to receive audio and visual instructions for undertaking a series of one or more predetermined body poses so that the cameras 418 can capture overlapping images of the user in the various body poses.

Front panel 406 includes a plurality of circular openings 428 for the lenses of the cameras 418 to be positioned within, or seen therethrough, in order to provide camera access to the enclosed interior area 402 of the imaging station/booth 400, and at least two vertically oriented rectangular openings 430 that enable each of the light panels 422 to be inserted therethrough so that light is provided to the enclosed interior area 402 of the imaging station/booth 400 so that cameras 418 can capture readable images of users in one or more series of predetermined poses. The light panels 422 are positioned on opposing sides of the cameras 418 so that the enclosed interior area 402 will be properly lit for taking images of users.

The body positioning members 426,429 located within the enclosed interior area 402 enable a user to accurately position his/her body in a series of one or more predetermined body poses. The body positioning members 426,429 include one or more handles 426 for a user's hands and a footplate 429 for the user's foot or feet. One or more outlined areas for placement of the user's feet may also be included on the floor member 421 and/or footplate 429 of the imaging station/booth 400. The handles 426 and/or footplate 429 may further include a light emitting component with capacitive touch sensors (see FIGS. 39-40) which enable the handles 426 and/or footplate 429 to light op when properly engaged by a user in order to accurately pose in a series of one or more predetermined body poses. The handles 426 may be secured to the rear panel 414 of the imaging station/booth 400 and the footplate 429 may be movable and retractable within floor member 421 of the imaging station/booth 400. Visual display device(s) 424 may be attached to and supported by bar members 425 which are connected to the imaging station/booth 400. Imaging station/booth 400 may also include one or more moveable or removable outer front panels 432 which can be moved to access the cameras 418, an outer rear panel 433, a frame 420, one or more sneaker component(s) 427 and other components such as a computer processing unit 434 that is in communication with one or more program application(s) related to the use of the imaging station/booth 400.

Program application(s) may include one or more of: i) a program application for taking, capturing, and storing the overlapping images produced by cameras 418, ii) an automatic focusing algorithm to automate focusing of cameras 418 by determining an area of interest for each camera 418 in each of the one or more predetermined poses undertaken by a user, iii) a program application that enables a medical professional and/or medical facility (such as hospitals, medical clinics, etc.) to obtain wireless access to the overlapping images in order to view the overlapping images, compare a plurality of the overlapping images of a same user taken at different times, document notes relating to the overlapping images, create electronic medical records that include the overlapping images, and/or send the overlapping images and related notes to another medical professional and/or medical facility, and iv) a program application that enables a medical professional and/or medical facility having access to the overlapping images of a user to interface with other existing electronic medical record databases front other medical professionals and/or medical facilities utilized by the user so that the overlapping images of the user can be compared to other existing electronic record databases.

Figure 27:
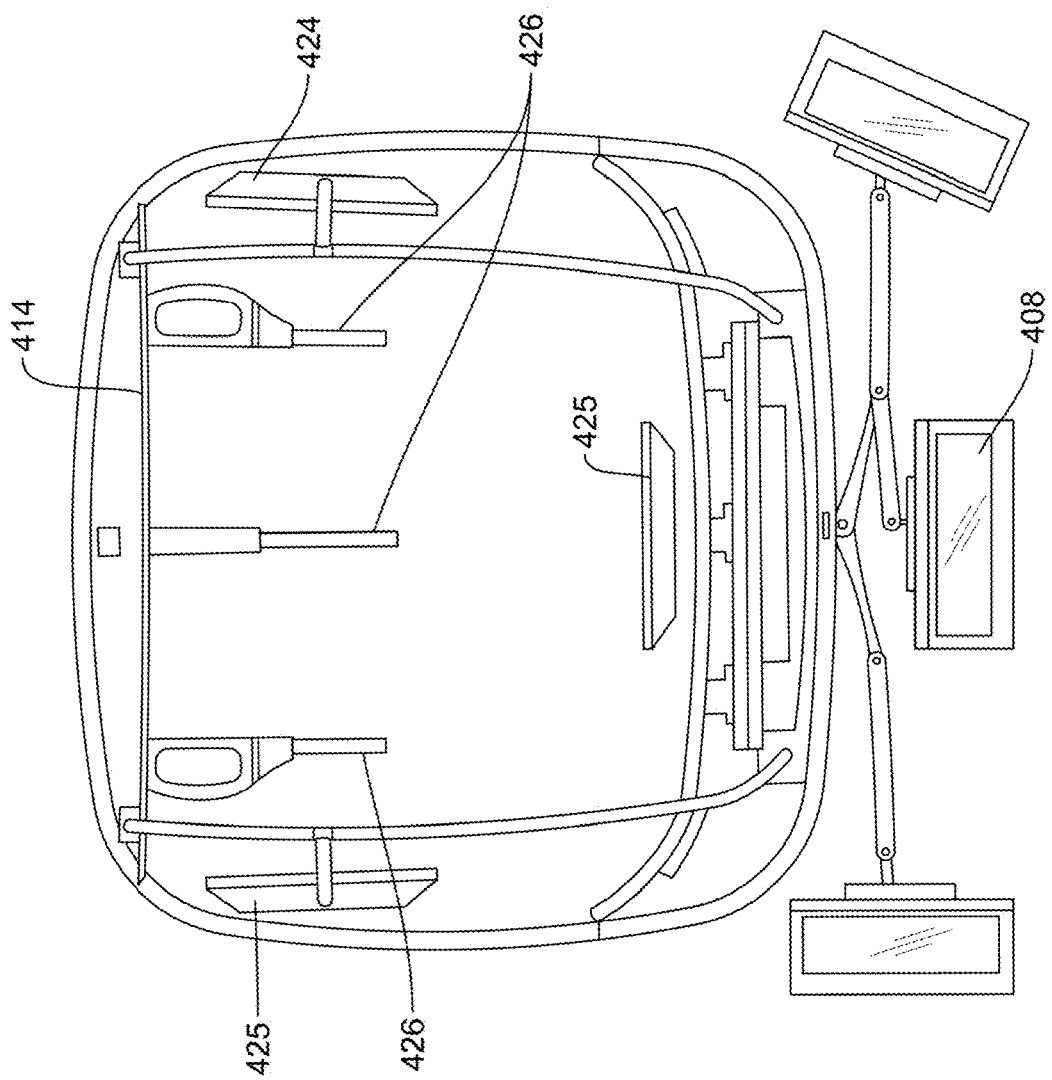
FIG. 27 is a fop plan view showing the interior of the exemplary embodiment of the imaging station/booth of the present invention shown in FIGS. 25 and 26.
Figure 28:
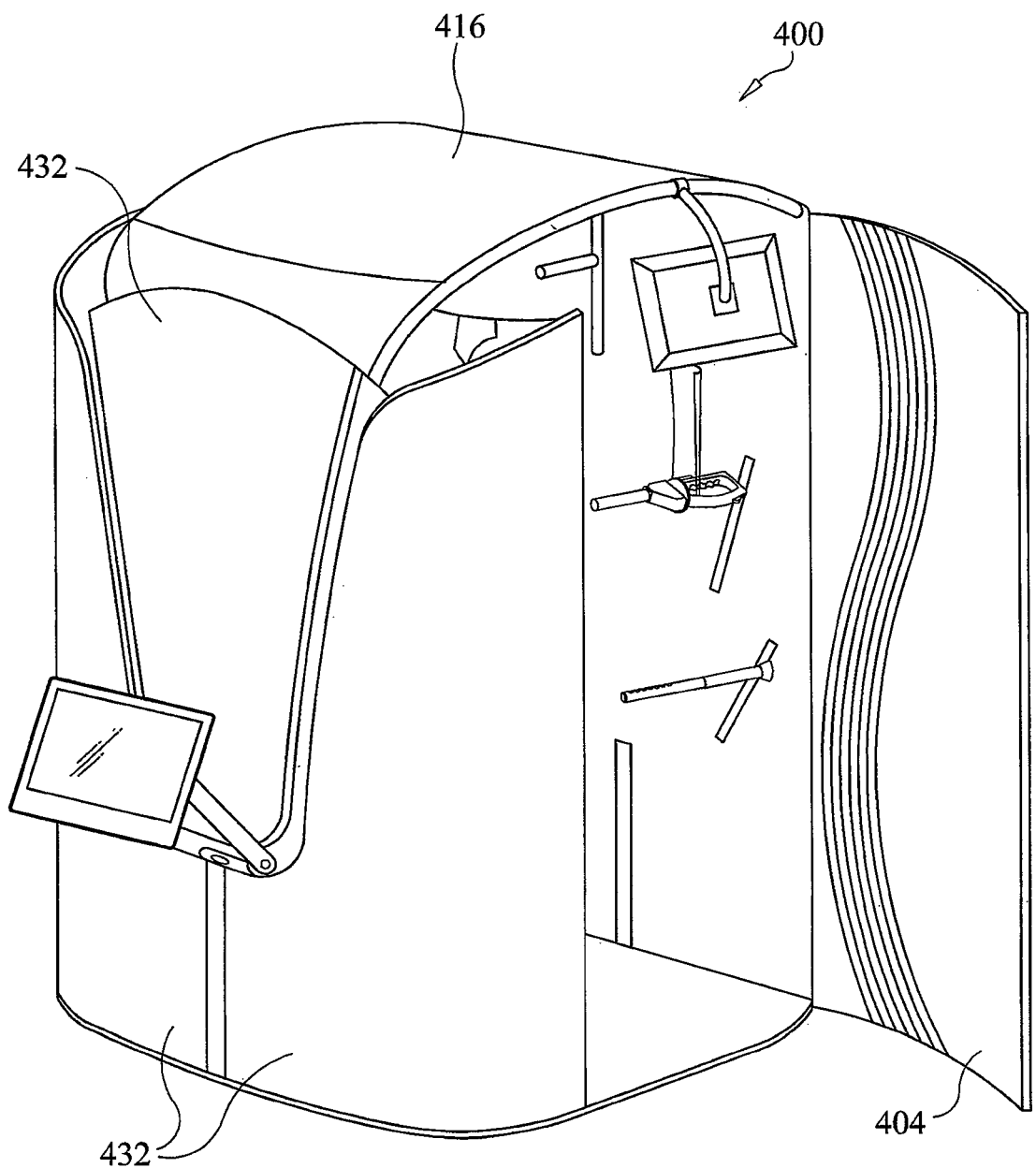
FIG. 28 is an outer perspective view of the exemplary embodiment of the imaging station/booth of the present invention depicted in FIG. 25 with a door of the imaging station/booth shown open.

FIG. 27 is a top plan view showing the interior of the exemplary embodiment of the imaging station/booth 400 of the present invention shown in FIGS. 25 and 26. FIG. 27 shows handles 426 secured to rear panel 414 of the imaging station/booth 400, three visual display devices 424 contained within the enclosed interior area 402 of the imaging station/booth 400, and one technician computer device 408 which can be moved, tilted, and rotated in a variety of directions as shown in phantom. FIG. 28 is an outer perspective view of the exemplary embodiment of the imaging station/booth 400 of the present invention depicted in FIG. 25 with the door 404 of the imaging station/booth 400 shown open.

Figure 29:
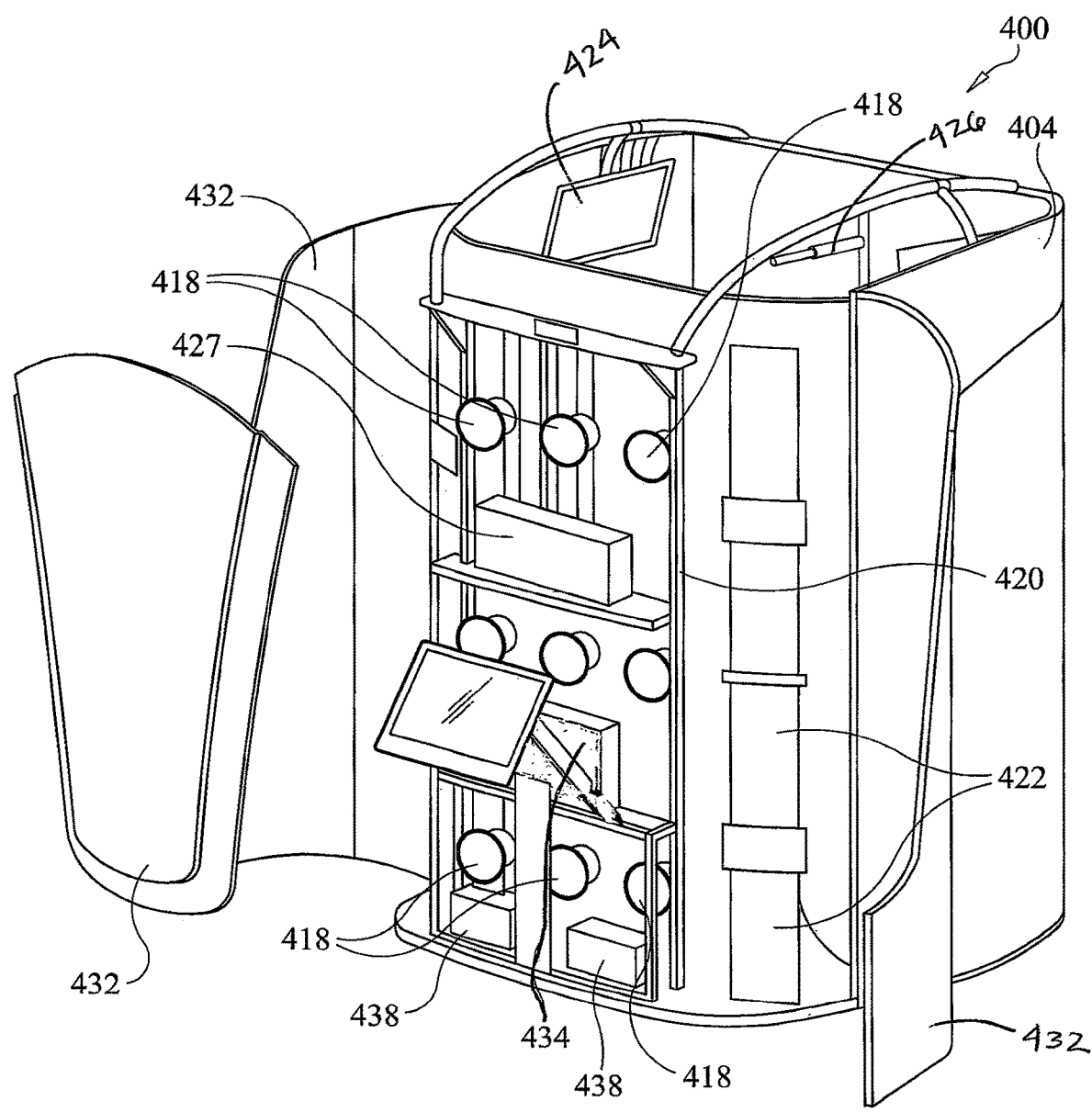
FIG. 29 is an outer perspective view of the exemplary embodiment of the imaging station/booth of the present invention depicted in FIG. 25 with outer front panels shown in an open position.

FIG. 29 is an outer perspective view of the exemplary embodiment of the imaging station/booth 400 of the present invention depicted in FIG. 25 with outer front panels 432 shown in an open position. As shown, the outer front panels 432 can be moved and/or removed to provide access to the plurality of cameras 418 secured to the frame 420, one or more speaker components 427, light panels 422, a computer processing unit 434 in communication with one or more program applications relating to the use of the imaging station/booth 400, and other electronic components 438 and connections relating to the operation of the imaging station/booth 400.

Figure 30:
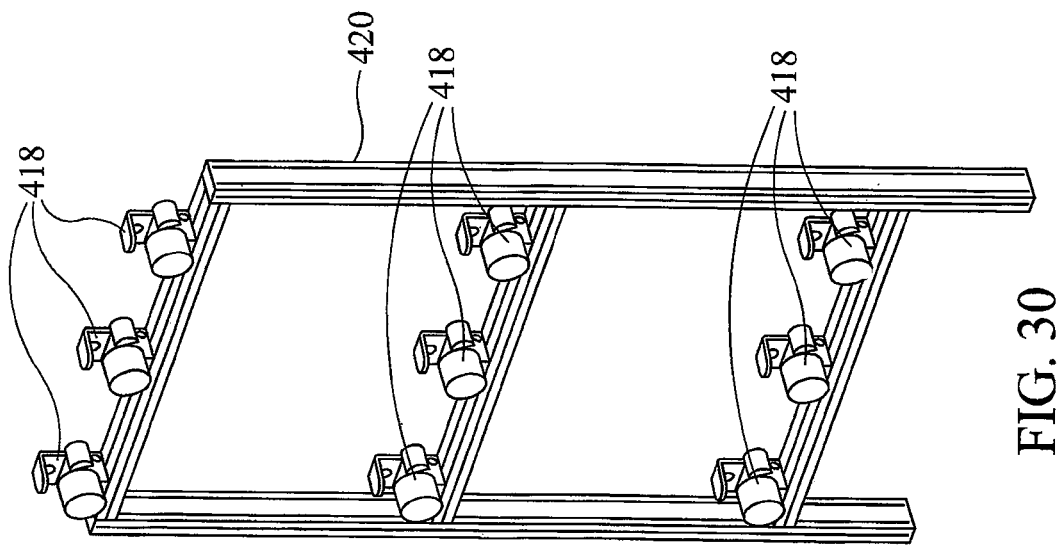
FIG. 30 is a perspective view of the plurality of cameras and the frame which supports the plurality of cameras contained in the imaging station/booth shown in FIGS. 25 and 26.

A perspective view of an exemplary embodiment of the plurality of cameras 418 and the frame 420 which supports the plurality of cameras 418 contained in the imaging station/booth 400 is shown in FIG. 30. In this exemplary embodiment, there are nine cameras 418 each secured to frame 420 such that the cameras 418 create an array of three horizontal rows of cameras 418 with three cameras 418 secured to each horizontal row. In one exemplary embodiment utilizing this array of cameras, the cameras may be horizontally spaced along each horizontal row such that they are approximately 14 inches apart from one another and vertically spaced such that the first row of three cameras is approximately 12 inches from the bottom of the imaging station/booth 400, the second row of three cameras is approximately 26.5 inches from the first row of cameras and the third row of three cameras is approximately 26.5 inches form the second row of cameras. The frame may also be positioned such that each of the cameras are at a distance of approximately 0.73 meters to the user of the imaging station/booth 400. Each of the cameras 418 may be secured to the frame 420 by way of quick release level mounts.

Figure 31:
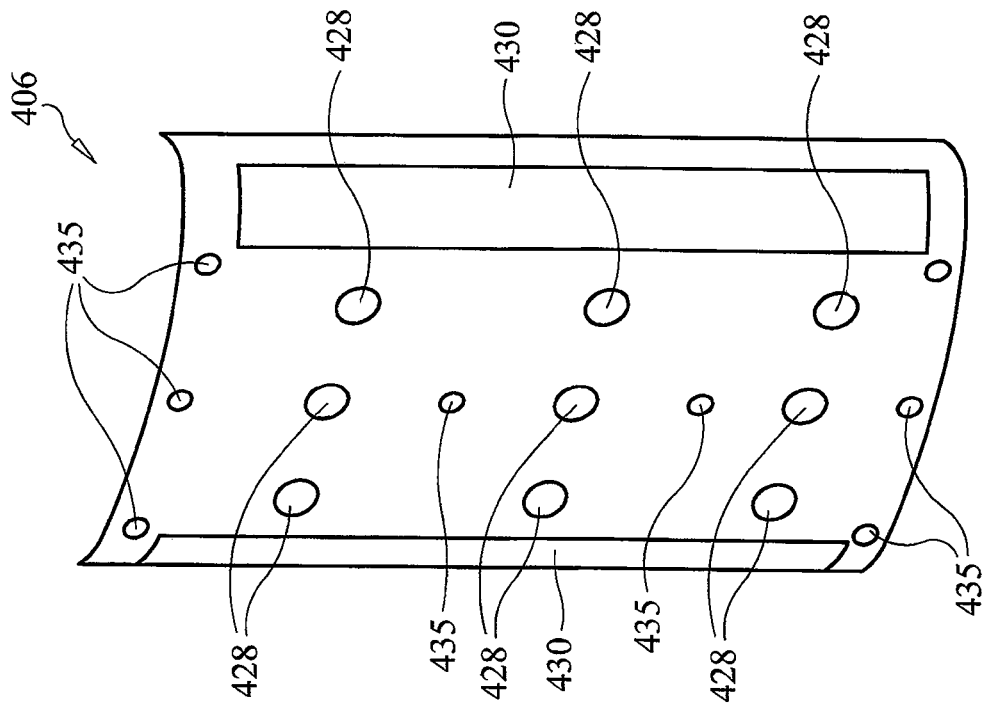
FIG. 31 is a front perspective view of the front panel of the imaging station/booth shown in FIGS. 25 and 26 having openings contained therein for the camera lenses and the light panels.
Figure 32:
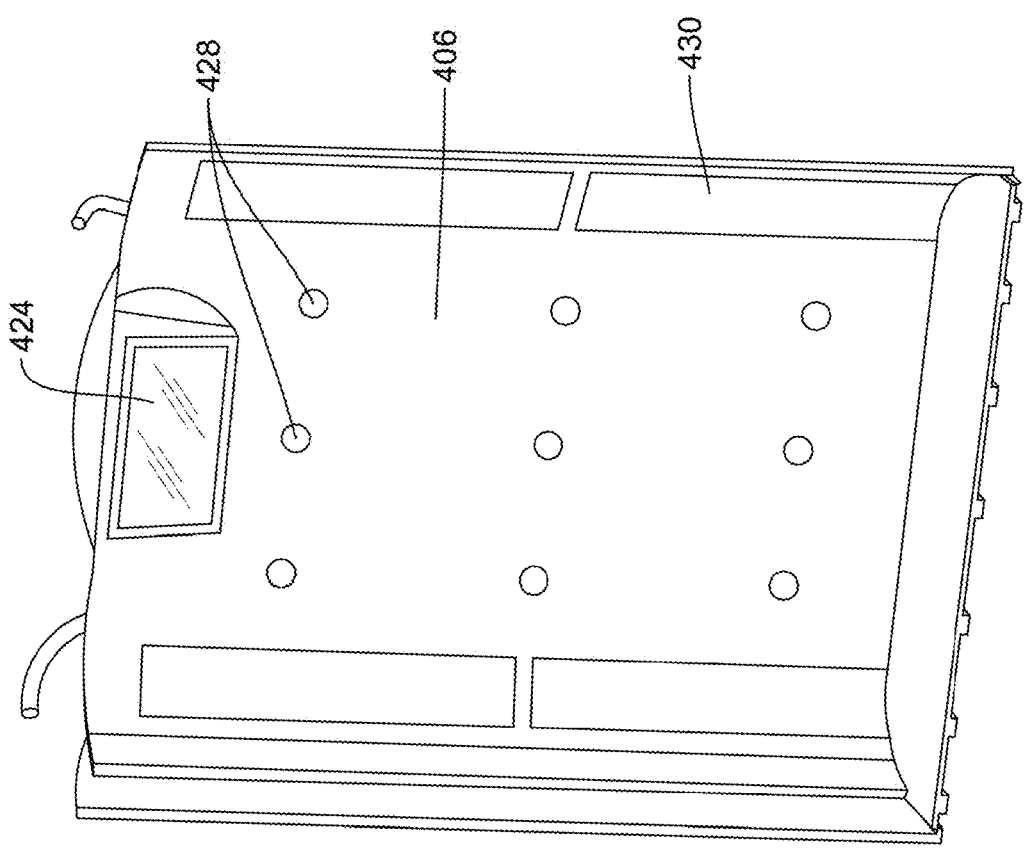
FIG. 32 is a partial interior view of the imaging station/booth shown in FIGS. 25 and 26 showing a rear perspective view of the front panel of the imaging station/booth having openings contained therein for the camera lenses and the light panels, the light panels contained within the imaging station/booth, and an image display device contained within the imaging station/booth interior.
Figure 33:
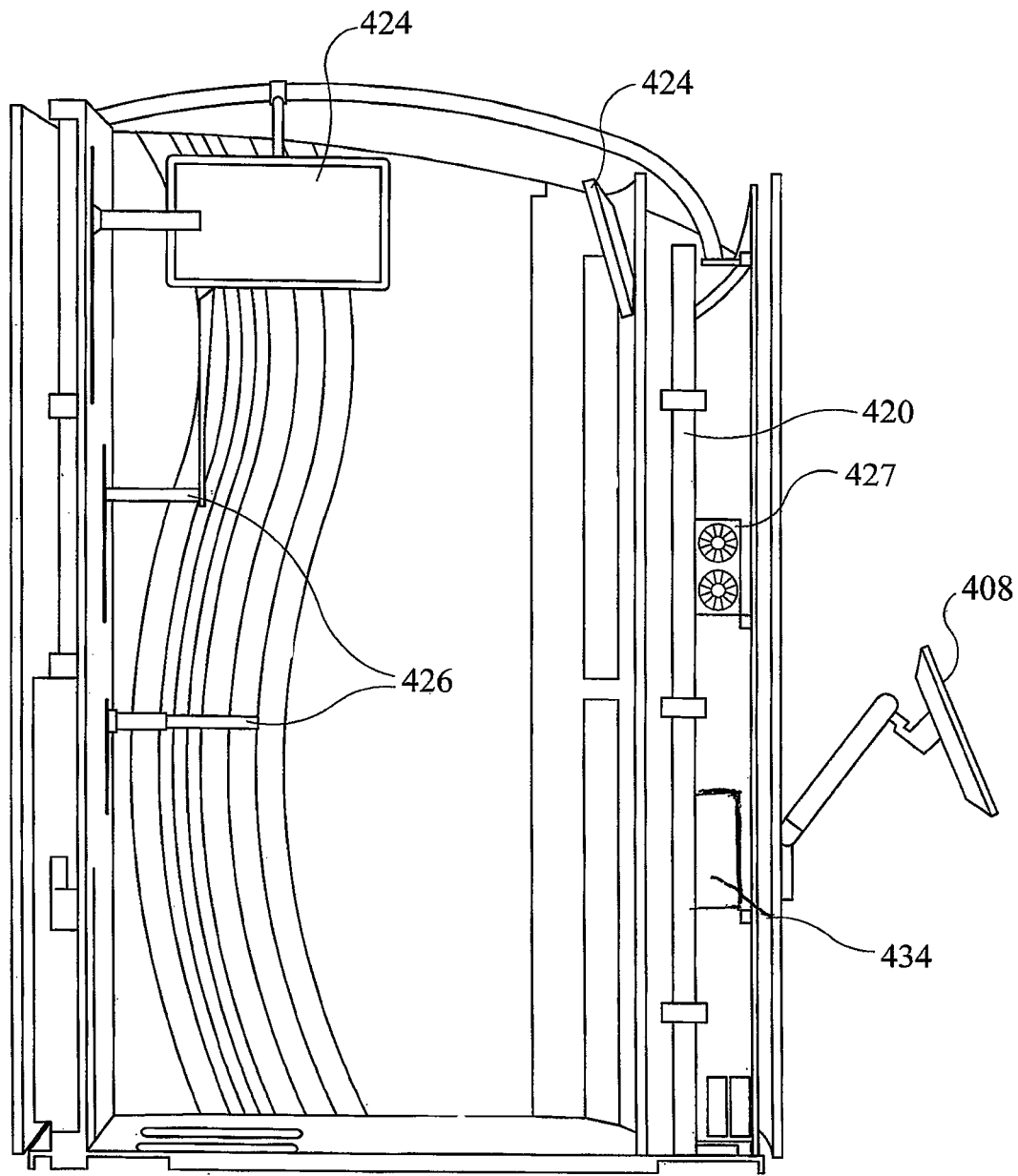
FIG. 33 is a partial interior view of the imaging station/booth shown in FIGS. 25 and 26 showing the inferior of the imaging station/booth with the side panel of the station/booth opposite the door removed.
Figure 34:
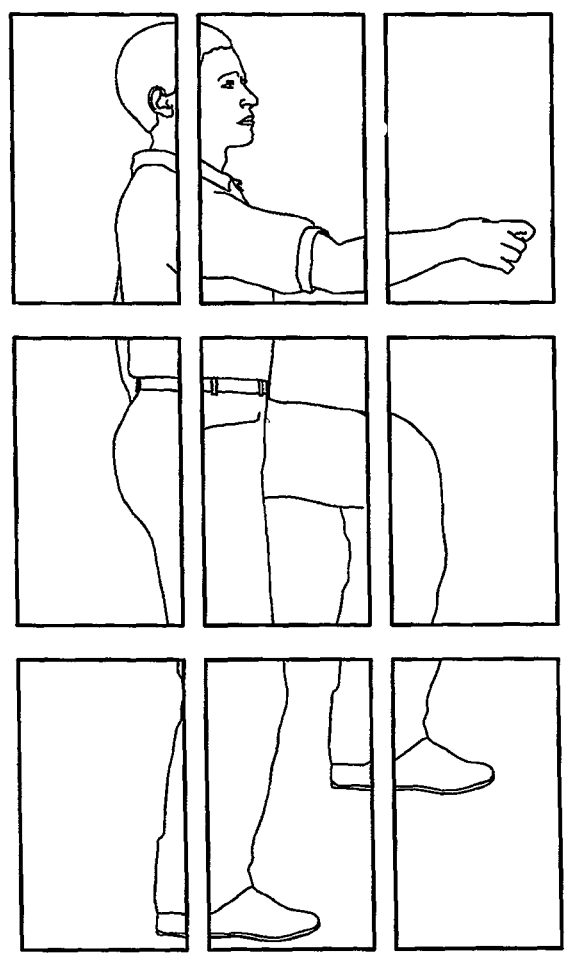
FIG. 34 is an example of the overlapping images of a user that are created with the plurality of cameras contained within the imaging station/booth shown in FIGS. 25 and 26.

FIG. 31 is a front perspective view of the front panel 406 of the imaging station/booth 400 having openings contained therein for the camera lenses and the light panels. A plurality of circular openings 428 are positioned within and through the front panel 406 such that they coincide directly with each of the plurality of cameras 418, respectively, that are secured to the frame 420 so that the lenses of the cameras 418 can be seen from the enclosed interior area 402 of the imaging station/booth. At least two vertically oriented rectangular openings 430 are positioned on opposing sides of the cameras 418 so that a light panel 422 can be inserted into each vertically oriented rectangular opening 430. The light panels 422 can be seen from the enclosed interior area 402 of the imaging station/booth 400 and function to provide adequate lighting for the cameras 418 in order for the cameras 418 to produce readable images. The readable images produced from the cameras are overlapping images of the user who is posing in a series of one or more predetermined body poses. An example of such overlapping images of the user produced by the cameras 418 is shown in FIG. 34. Front panel 406, as well as opposing side panels 410,412, rear panel 414, top cover member 416, and any other panels such as outer from panels 432 and outer rear panel 433, may, in one exemplary embodiment, comprise a sandwich fiberglass structure with embedded inserts 435 in the fiberglass that function as connection points to hold the panel structures together. FIG. 32 shows an interior view of the front panel 406 and other interior station/booth components as seen from the enclosed interior area 402 of the imaging station/booth 400 and FIG. 33 is a partial interior view of the imaging station/booth 400 showing the interior of the imaging station/booth 400 with the side panel 410 of the imaging station/booth opposite the door 404 removed.

Figure 35:
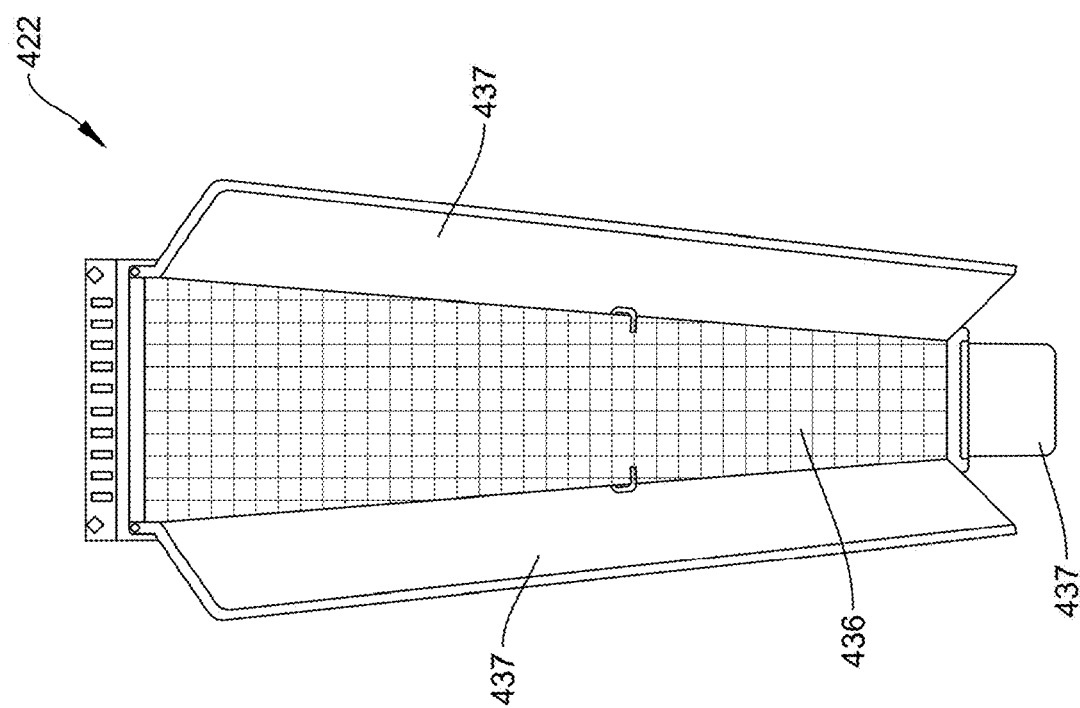
FIG. 35 is front perspective view of an exemplary embodiment of the light panels contained within the imaging station/booth shown in FIGS. 25 and 26.

A front perspective view of an exemplary embodiment of the light panels 422 contained within the imaging station/booth 400 shown in FIGS. 25 and 26 is depicted in FIG. 35. Light panels 422 each include one or more lighting components 436 and one or more filtering/reflecting panels 437. The one or more lighting components may comprise light emitting diode(s) (LEDs) or LED panel(s) that provide a constant light source thereby providing a minimal sync with the shutters of the cameras 418. The brightness of the light panels 422 may be controlled through a computer program application run by the computer processing unit 434 and the light panels 422 can also serve to provide ambient lighting within the enclosed interior area 402 of the imaging station/booth 400.

Figure 36:
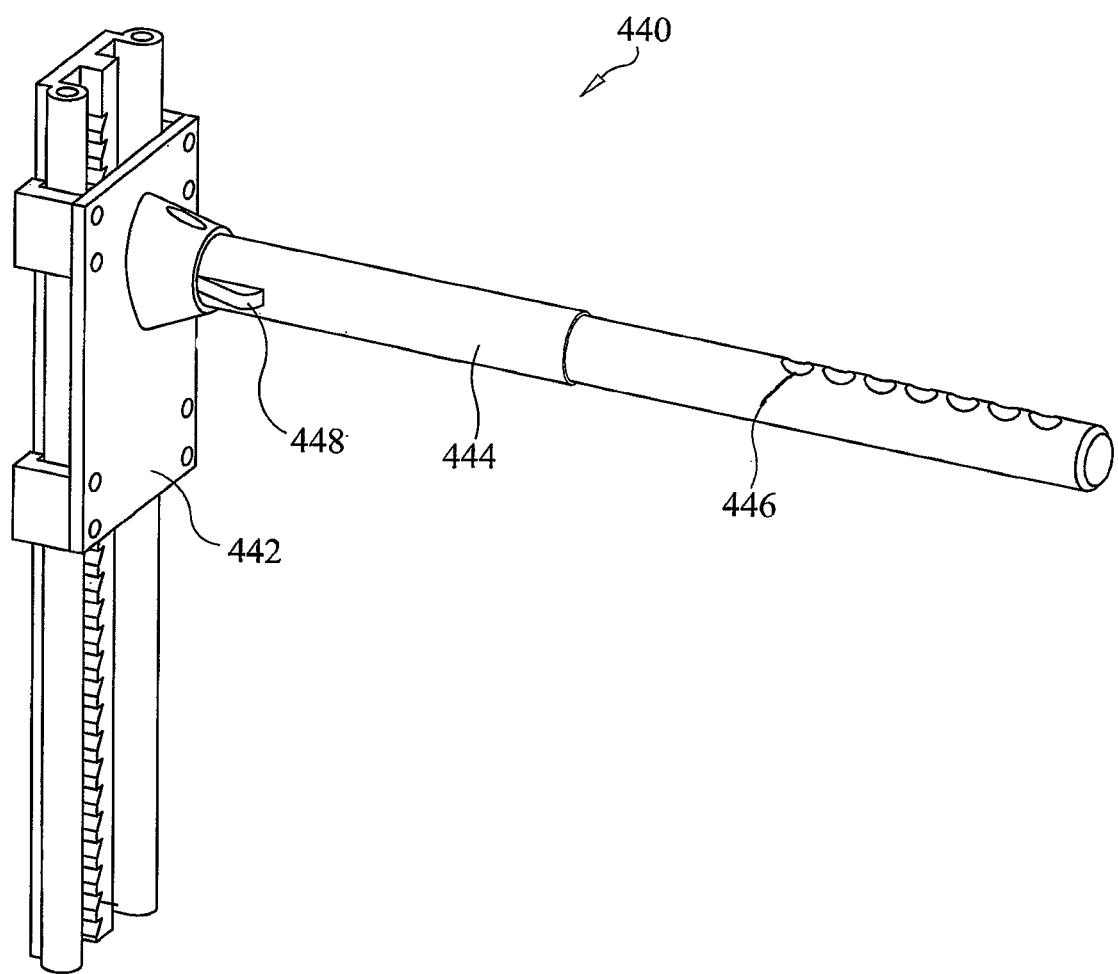
FIG. 36 is a perspective view of an exemplary embodiment of an interior upper handle that is secured to a rear of the imaging station/booth shown in FIGS. 25 and 26.

FIG. 36 is a perspective view of an exemplary embodiment of an interior upper handle 440 (see FIG. 9 for placement/position of this handle on rear panel 414) that is secured to a rear of the imaging station/booth shown in FIGS. 25 and 26. Interior upper handle 440 includes a slide and lock mechanism 442 and a handle bar 444 connected to the slide and lock mechanism 442. A portion of handle bar 444 includes high power LED capacitive touch sensors 446 which are capable of lighting up when a user properly engages inferior upper handle 440 with the user's hand and/or fingers for certain predetermined poses. The slide and lock mechanism 442 contains discreet locking positions in which the position of handle bar 444 can be easily moved and locked with the movement of one hand by pressing lever/button 448 and then sliding the handle bar 444 up or down. In addition, handle bar 444 may be extended up to approximately twenty two inches for broad shouldered users. Interior upper handle 440 is used for pose numbers 7 and 8 shown in FIG. 17 which depicts an exemplary predetermined set of body poses for complete body imaging in accordance with the system and apparatus for full body imaging of the present invention.

Figure 37:
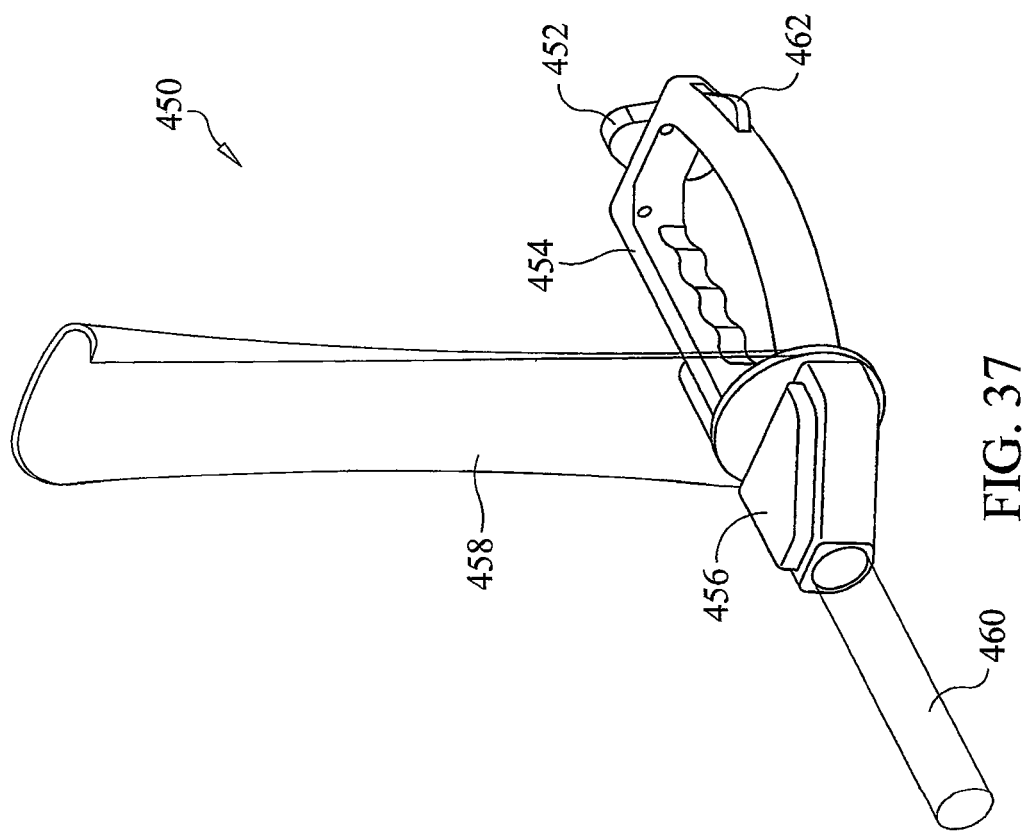
FIG. 37 is a perspective view of an exemplary embodiment of an interior middle handle that is secured to a rear of the imaging station/booth shown in FIGS. 25 and 26.

A perspective view of an exemplary embodiment of an interior middle handle 450 (see FIG. 9 for placement/position of this handle on rear panel 414) that is secured to a rear of the imaging station/booth 400 shown in FIGS. 25 and 26 is depicted in FIG. 37. Interior middle handle 450 includes a slide and lock mechanism 452, a handle bar 454 connected to the slide and lock mechanism 452, and an elbow support 456 and a wrist support 458 each connected to the handle bar 454. The wrist support 458 can be folded down against the elbow support 456 to improve accessibility. In addition, a portion of handle bar 454 includes high power LED capacitive touch sensors 460 which are capable of lighting up when a user properly engages interior middle handle 450, elbow support 456, and/or wrist support 458 with the user's hand, elbow, wrist, and/or fingers for certain predetermined poses. The slide and lock mechanism 452 contains discreet locking positions in which the position of handlebar 454 can be easily moved and locked with the movement of one hand by pressing lever/button 462 and then sliding the handle bar 454. In addition, handle bar 454 may be extended up to approximately twenty inches for broad shouldered users. Interior middle handle 450 is used for pose numbers 1, 4, 6 and 9 shown in FIG. 17 which depicts an exemplary predetermined set of body poses for complete body imaging in accordance with the system and apparatus for full body imaging of the present invention.

Figure 38:
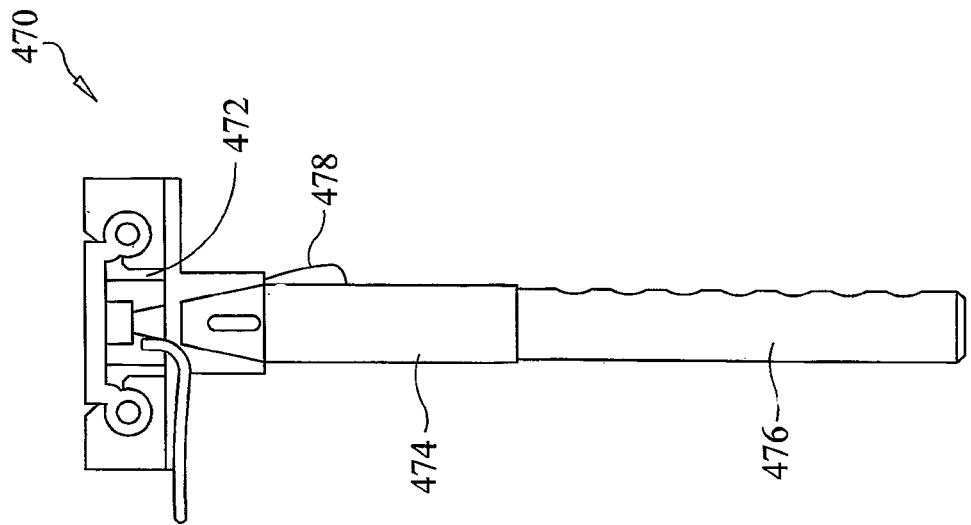
FIG. 38 is a perspective view of an exemplary embodiment of an interior lower handle that is secured to a rear of the imaging station/booth shown in FIGS. 25 and 26.

FIG. 38 is a perspective view of an exemplary embodiment of an interior lower handle 470 (see FIG. 9 for placement/position of this handle on rear panel 414) that is secured to a rear of the imaging station/booth 400 shown in FIGS. 25 and 26. Interior lower handle 470 is very similar to interior upper handle 440. Interior lower handle 470 includes a slide and lock mechanism 472 and a handle bar 474 connected to the slide and lock mechanism 472. A portion of handle bar 474 includes high power LED capacitive touch sensors 476 which are capable of lighting up when a user properly engages interior lower handle 470 with the user's hand and/or lingers for certain predetermined poses. The slide and lock mechanism 472 contains discreet locking positions in which the position of handle bar 474 can be easily moved and locked with the movement of one hand by pressing lever/button 478 and then sliding the handle bar 474 up or down. Interior lower handle 470 is used for pose numbers 2 and 5 shown in FIG. 17 which depicts an exemplary predetermined set of body poses for complete body imaging in accordance with the system and apparatus for full body imaging of the present invention.

Figure 39:
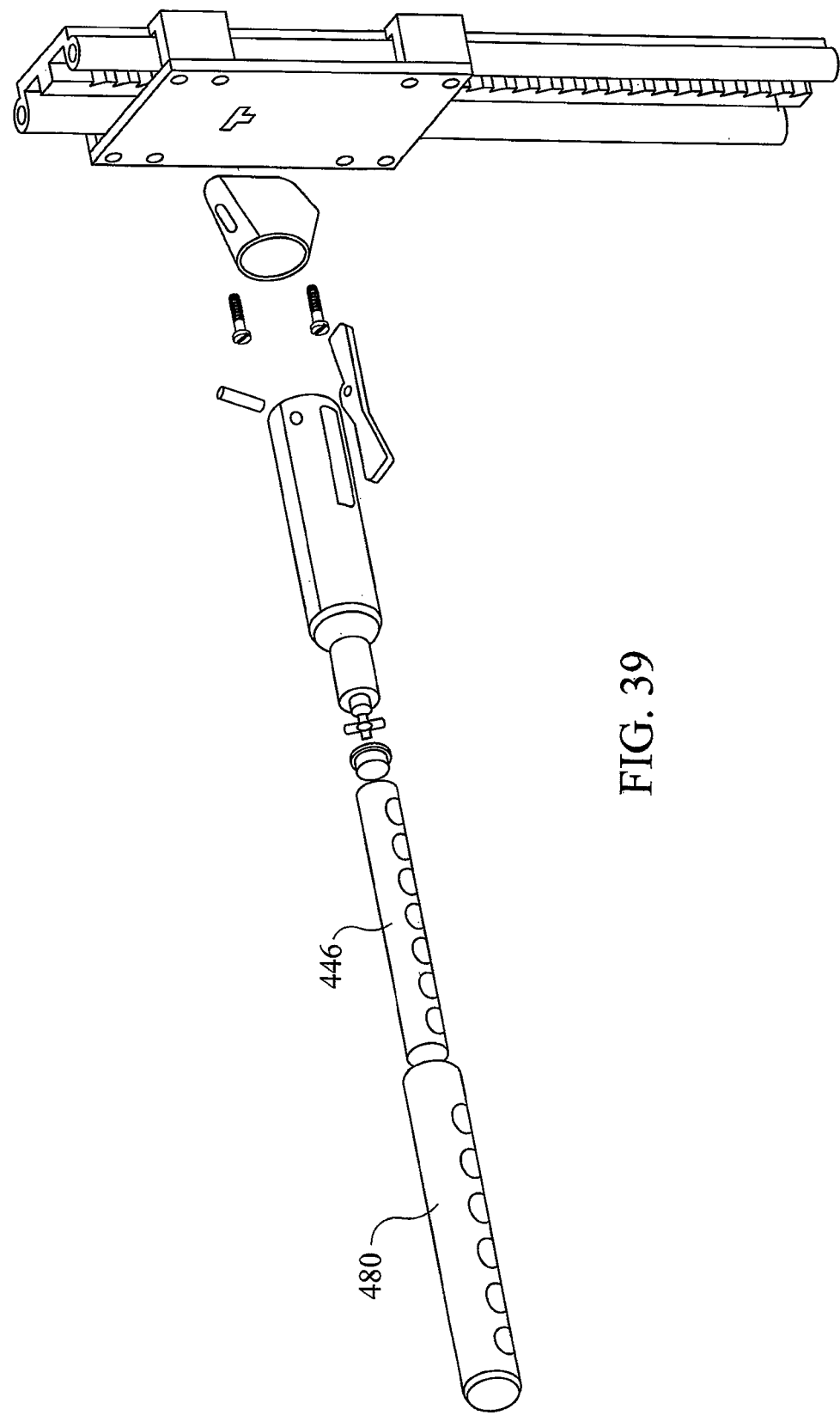
FIG. 39 is an exploded view of the interior upper handle shown in FIG. 36.
Figure 40:
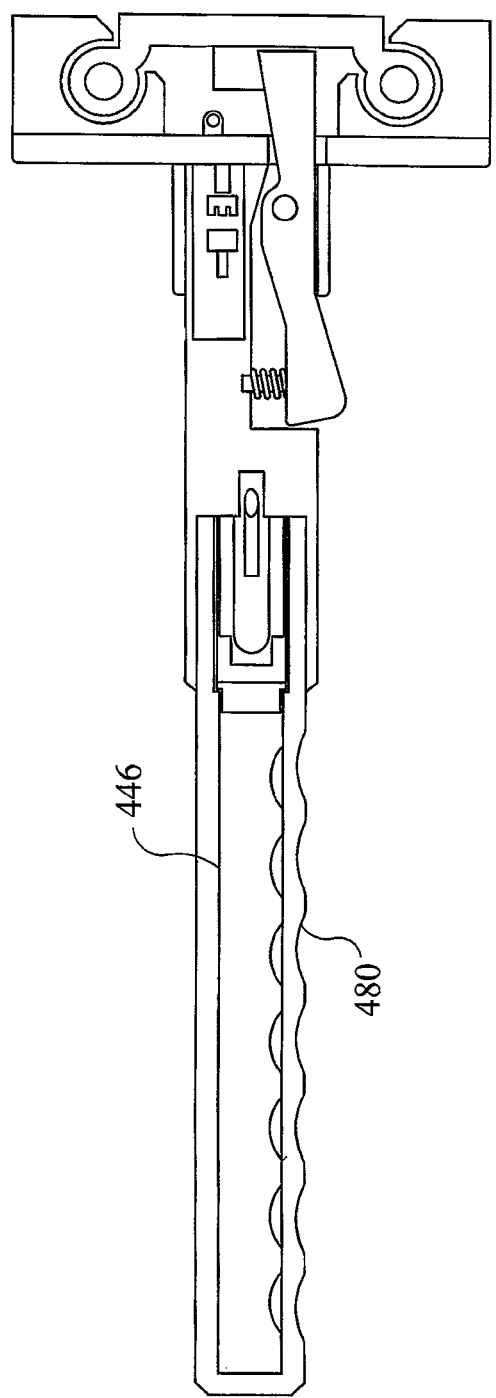
FIG. 40 is a horizontal cross-sectional view of the interior upper handle shown in FIG. 36.

FIG. 39 is an exploded view of the interior upper handle 440 shown in FIG. 36 and FIG. 40 is a horizontal cross-ssectional view of the interior upper handle 440 shown in FIG. 36. FIGS. 39 and 40 clearly show the electronics integration of the capacitive touch sensors 446 into the handle design, the connector for simple disassembly, and the removable plastic grip 480.

Figure 41:
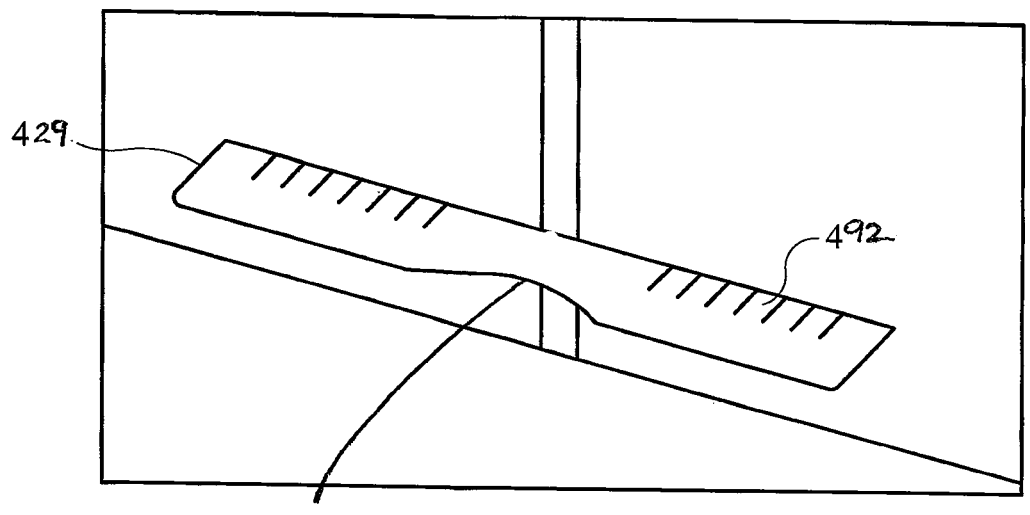
FIG. 41 is a perspective view of an exemplary embodiment of the movable foot plate contained within the imaging station/booth shown in FIGS. 25 and 26.
Figure 42:
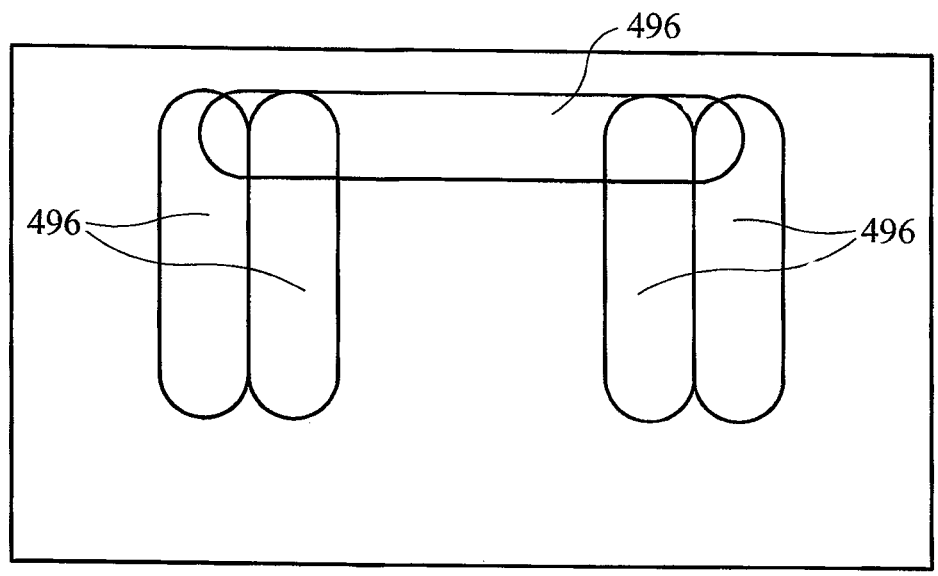
FIG. 42 is a top plan view showing an outline for exemplary placement of a user's feet on a floor within the imaging station/booth shown in FIGS. 25 and 26.

A perspective view of an exemplary embodiment of the movable foot plate 429 contained within the imaging station/booth 400 shown in FIGS. 25 and 26 is depicted in FIG. 41 in an elevated position. The movable foot plate 429 may be attached to a rod-less linear actuator in order to elevate the step upward and then retract it into the floor member 421. In addition, there may be a slight cut out area 490 in the moveable foot plate 429 to help signify a user's foot placement on the foot plate 429. A scale 492 may also be included as part of the foot plate 429 for repeatability between users. FIG. 42 is a top plan view showing outlined areas 496 for exemplary placement of a user's feet on floor member 421 within the imaging station/booth 400 shown in FIGS. 25 and 26. There are two sets of anterior/posterior foot placement areas. The outlined areas 496 may include one or more sensors for informing a user that they have correctly or incorrectly positioned their feet for the predetermined pose(s).

Figure 43:
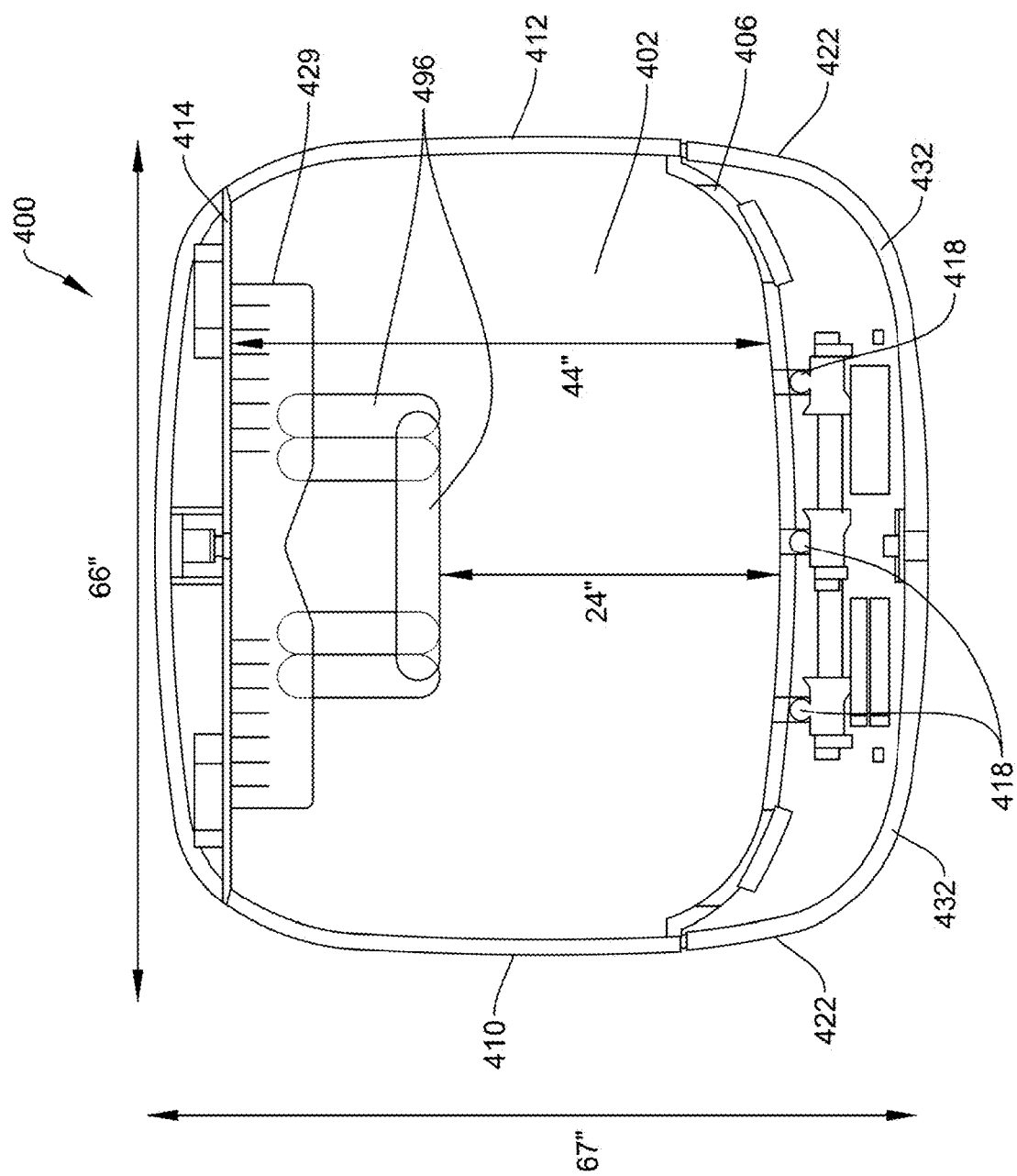
FIG. 43 is a top plan view of the interior of the imaging station/booth depicted in FIGS. 25 and 26 showing the placement and position of the foot plate and foot outlines shown in FIGS. 41 and 42, respectively.

FIG. 43 is a top plan view of the interior of the imaging station/booth 400 depicted in FIGS. 25 and 26 showing the placement and position of the loot plate 424 and outlined areas 496 shown in FIGS. 41 and 42, respectively, as well as a set of exemplary measurements for one exemplary embodiment of the imaging station/booth 400 of the present invention. As shown in FIG. 43, in one exemplary embodiment, the width of the imaging station/booth 400 at its widest point may be 66 inches and the depth of the imaging station/booth 400 at its longest point may be 67 inches thereby resulting in a generally square shaped enclosed interior area 402 having somewhat rounded edges. The distance between the front panel 406 and a user positioned within the enclosed interior area 402 is approximately 24 inches wherein the distance between the front panel 406 and the rear panel 414 is approximately 44 inches.

Figure 44:
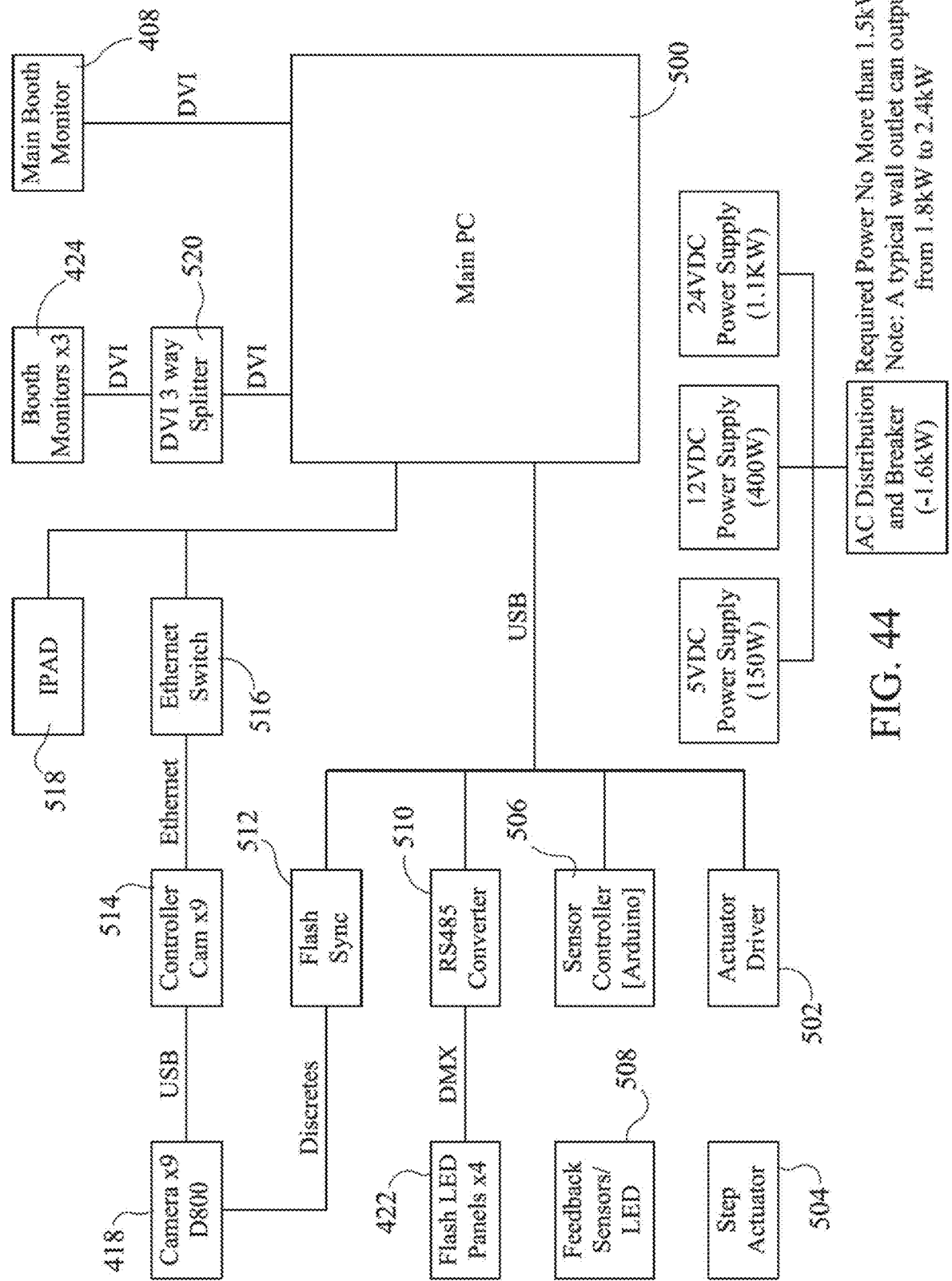
FIG. 44 shows a schematic of an exemplary electrical layout for the electrical components of the imaging station/booth shown in FIGS. 25 and 26.

A schematic of an exemplary electrical layout for the electrical components of the imaging station/booth 400 shown in FIGS. 25 and 26 is depicted in FIG. 44. The electrical layout includes a Main PC 500 which is in turn connected to i) an actuator driver 502 that is in turn connected to a step actuator 504 for the moveable step/foot plate 429, ii) a sensor controller 506 that is in turn connected to feedback sensor 508 for the LEDs contained within the body positioning members 426,429, iii) a converter 510 which is in turn connected to the light panels 422, and iv) a flash sync 512 that is in turn connected to cameras 418 which are in turn each connected to a controller 514 which are all in turn connected to an Ethernet switch 516 which itself enables connectivity to the Main PC 500 and tablet devices such as an IPAD 518. The Main PC 500 is also connected to the main station/booth monitor (or tech computer and monitor 408) as well as a 3 way splitter 520 which is in turn connected to each of the visual display devices 424.

Figure 45:
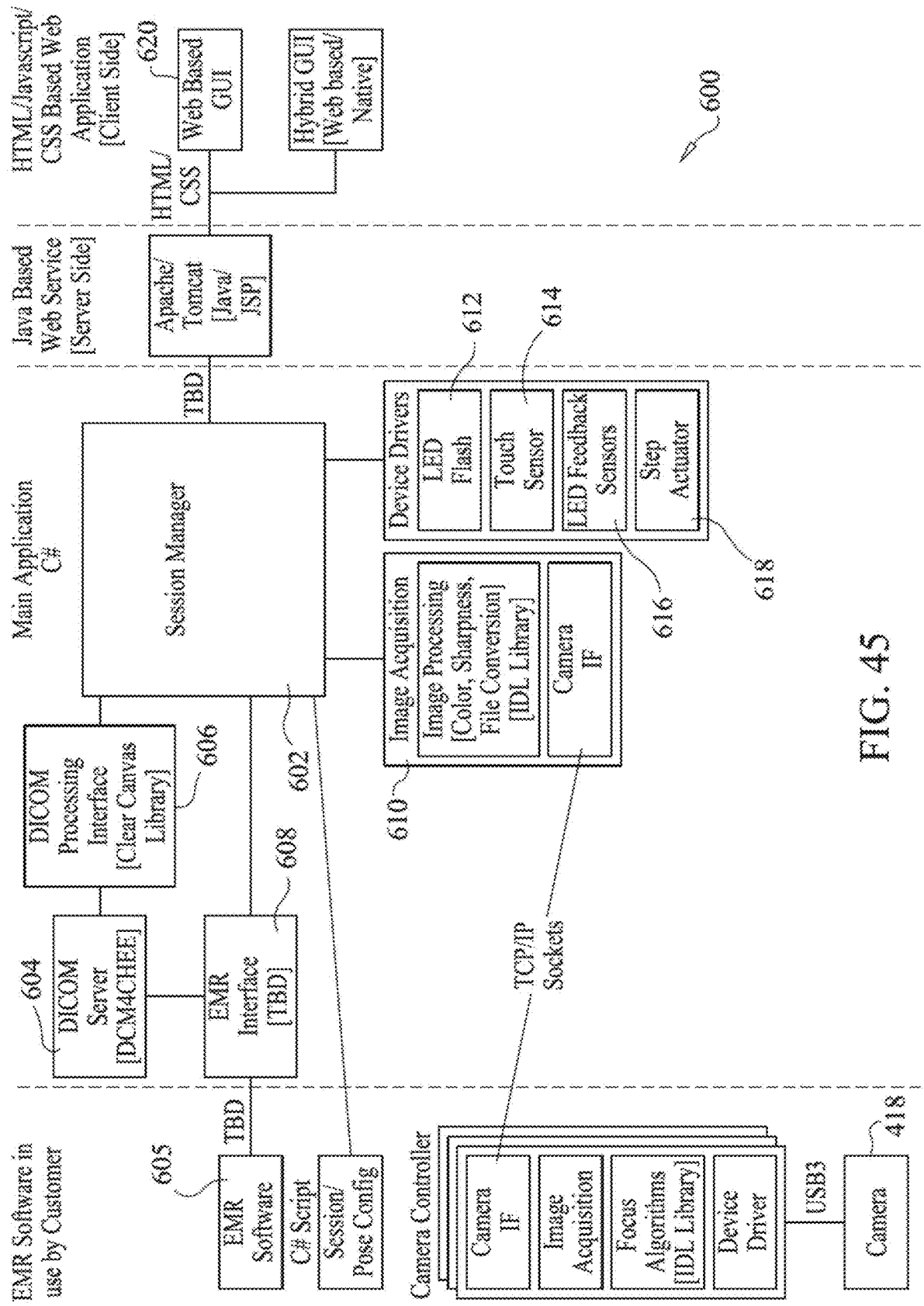
FIG. 45 is an exemplary software block diagram showing connections with the imaging station/booth shown in FIGS. 25 and 26.

FIG. 45 is an exemplary software block diagram showing connections with the imaging station/booth 400 shown in FIGS. 25 and 26. Software block diagram 600 includes a main application having a session manager 602 in communication with DICOM server 604 through a DICOM processing interlace 606. The session manager 602 and DICOMserver 604 are also in communication with an Electronic Medical Records (EMR) interface 608 that is in turn in communication with EMR software 605 being used by medical practitioners and/or medical facilities. Session manager 602 is also in communication with image acquisition program 610 which includes a camera interface to cameras 418 and image processing abilities, Session manager 602 is also in communication with a device driver 612 for the light panels 422, a device driver 614 for the touch sensors on the body positioning members 426,429, a device driver 616 for the LED feedback sensors associated with the body positioning members 426,429, and a device driver 618 for the step actuator associated with the moveable foot plate 429. The session manager 602 is also in communication with a web based service that presents a web based graphical user interface (GUI) 620 to a user.

Figure 47:
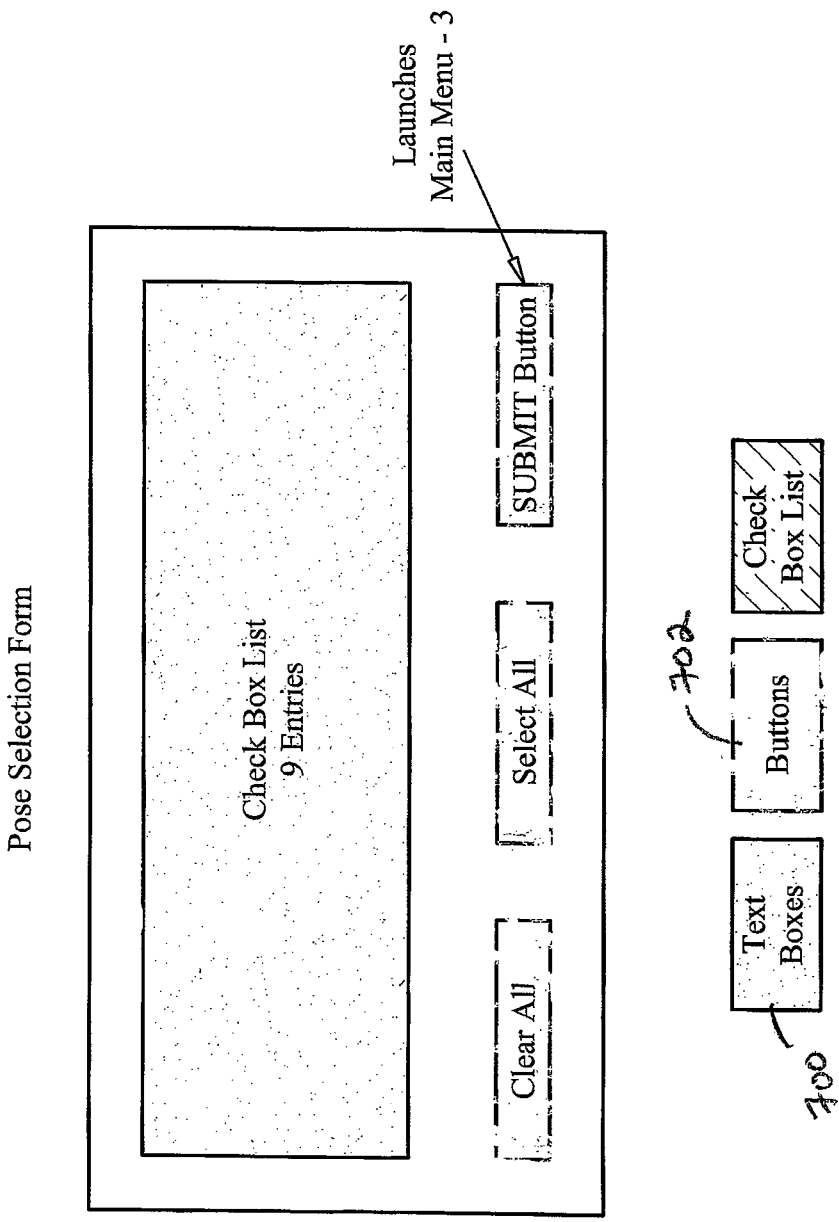
Figure 48:
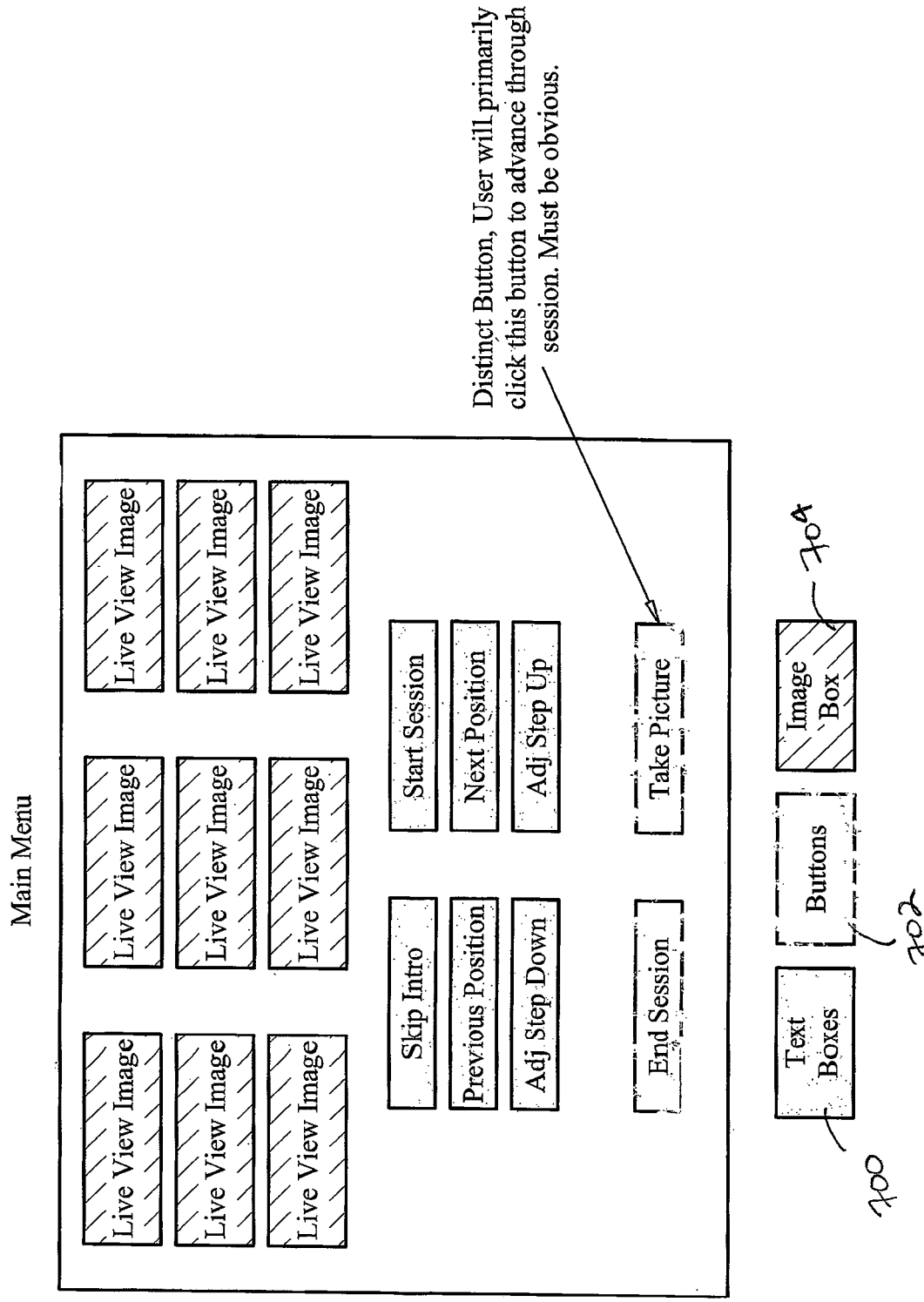
Figure 49:
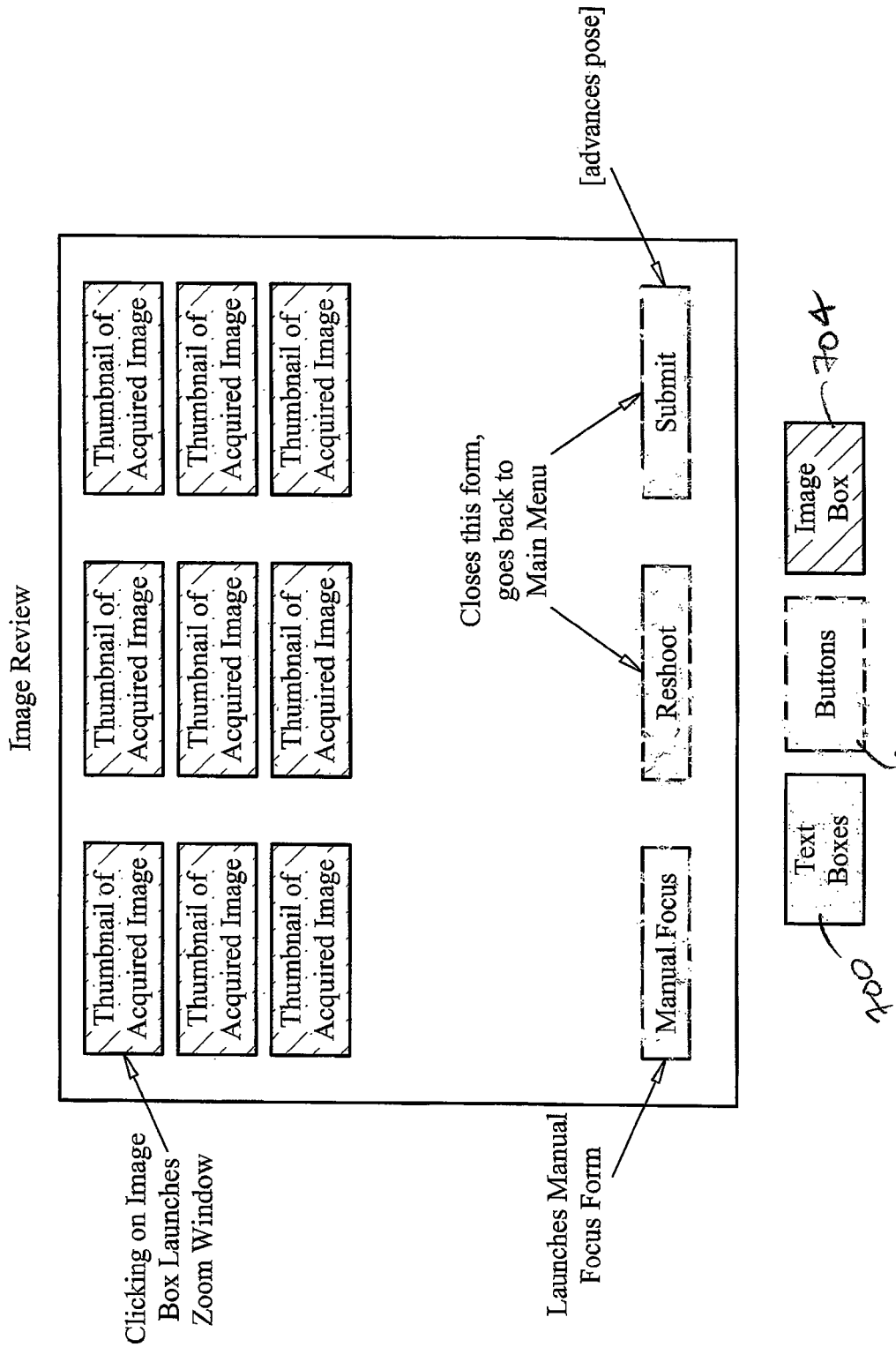
Figure 50:
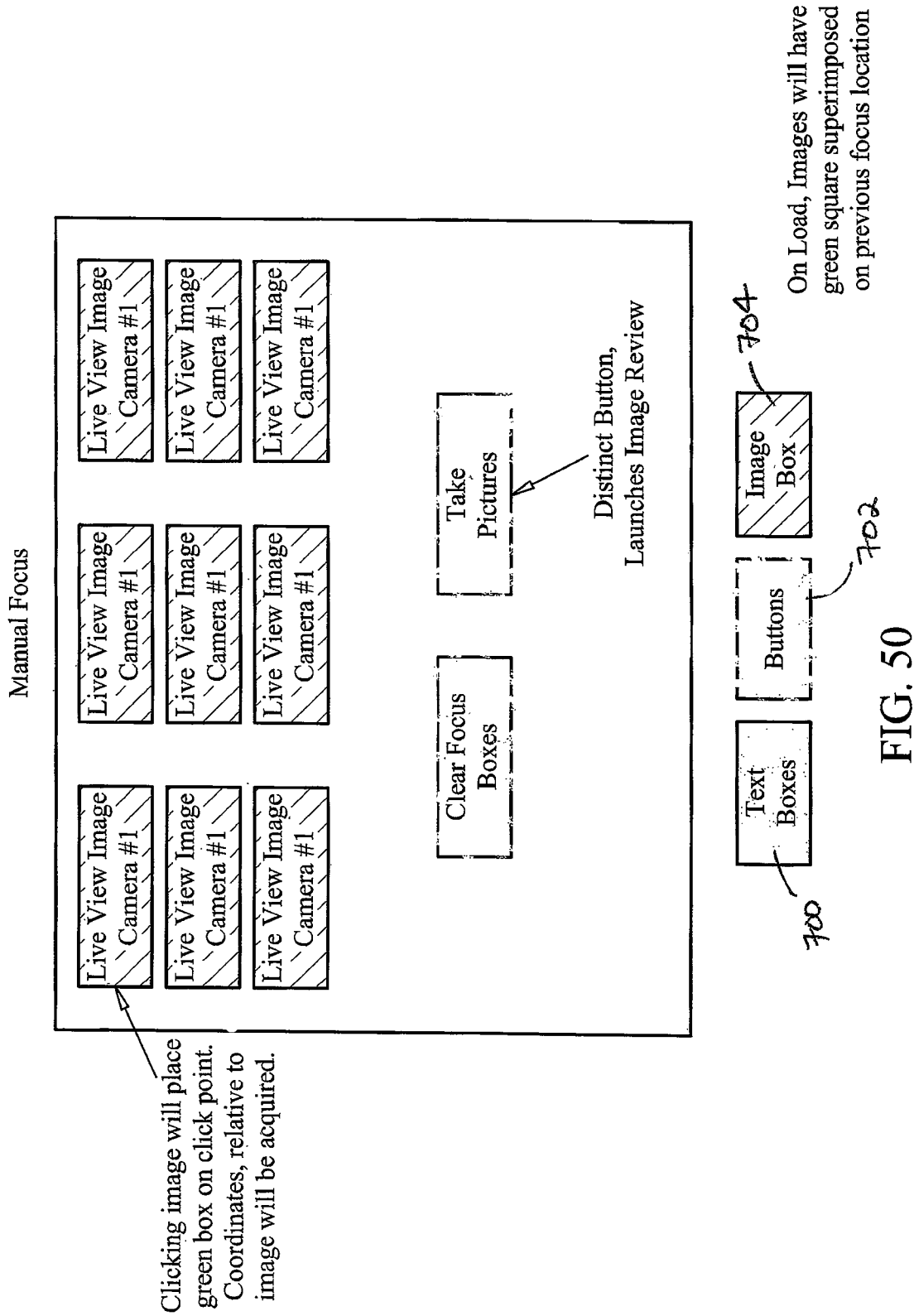
Figure 51:
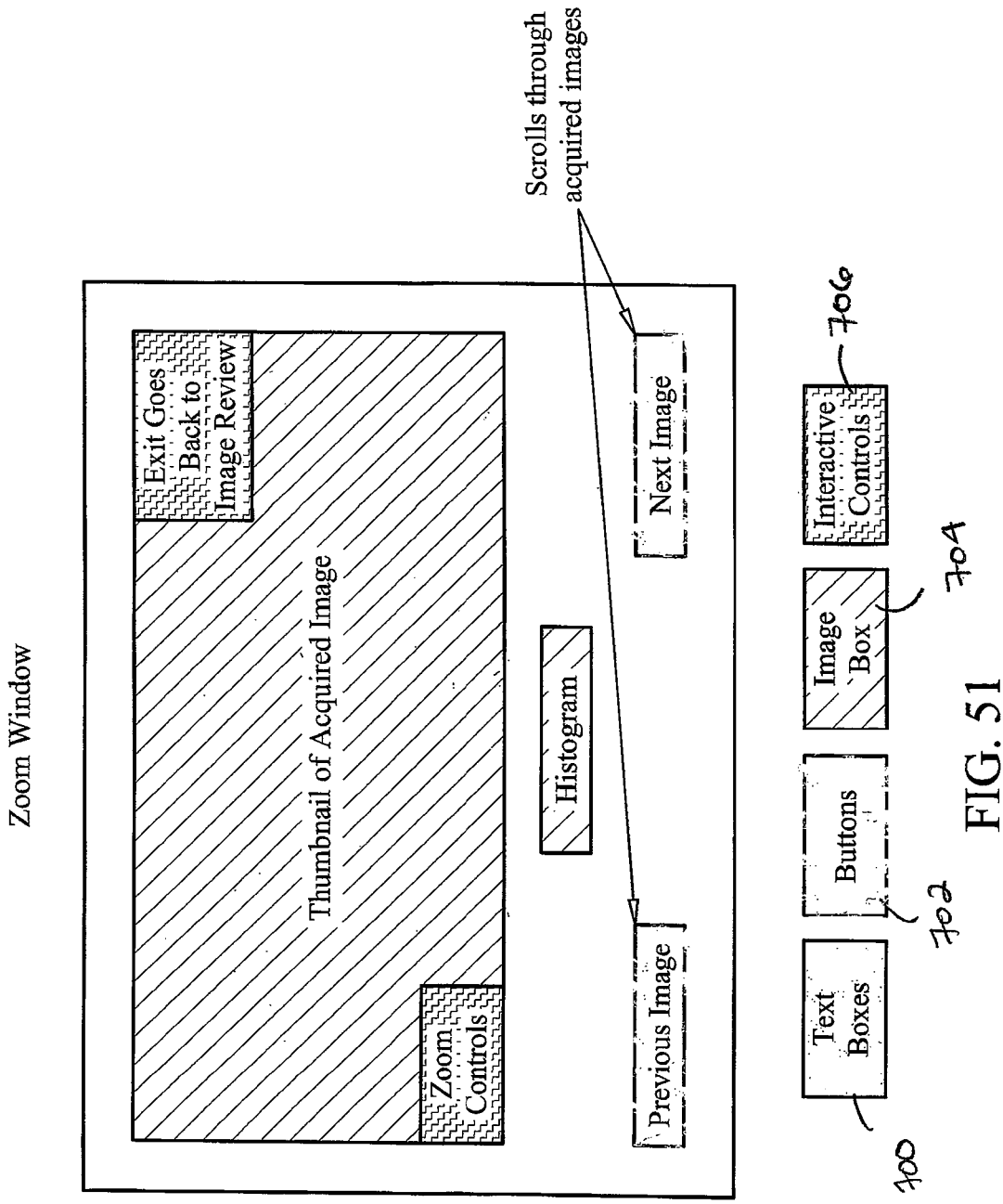
Figure 52:
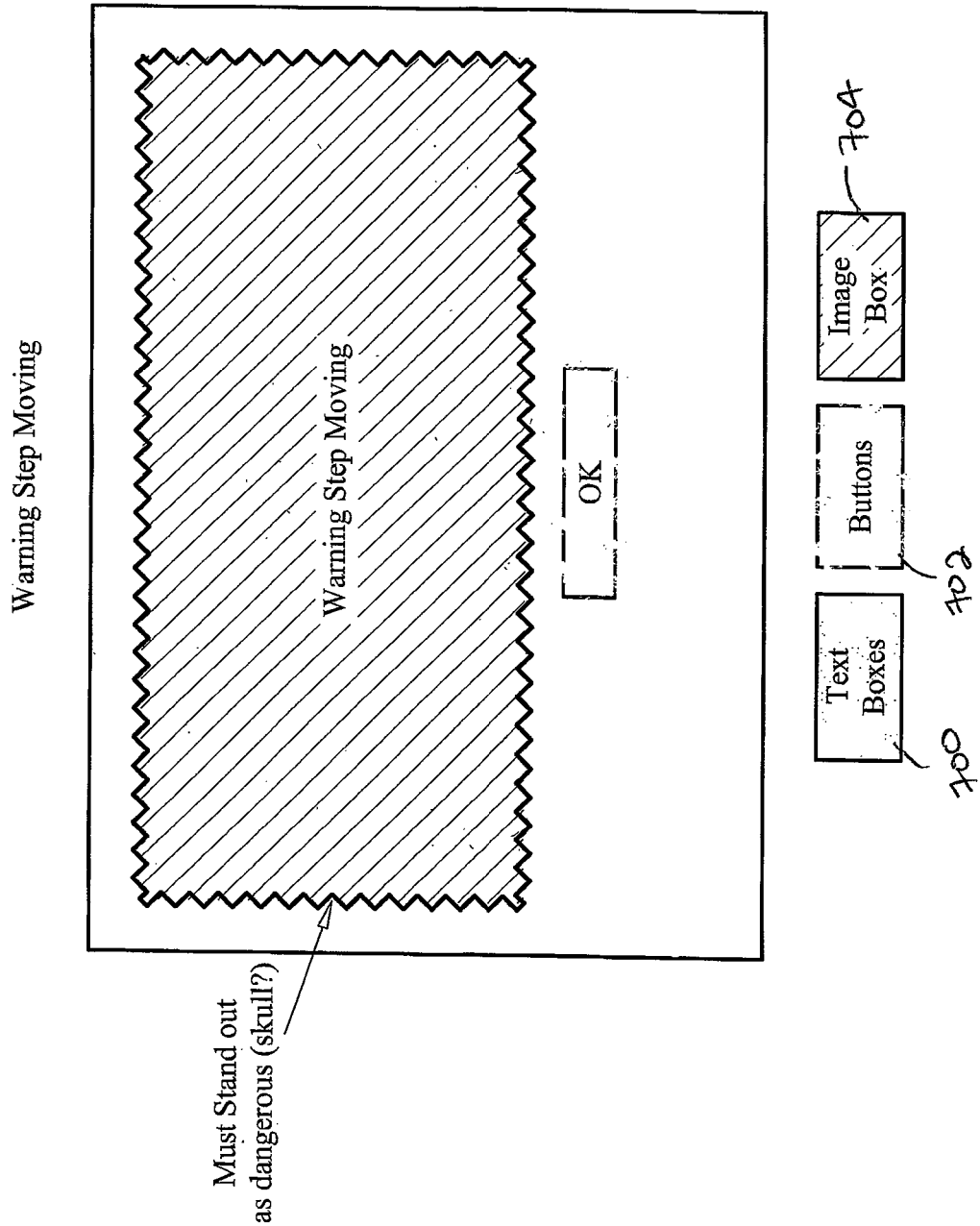
Figure 53:
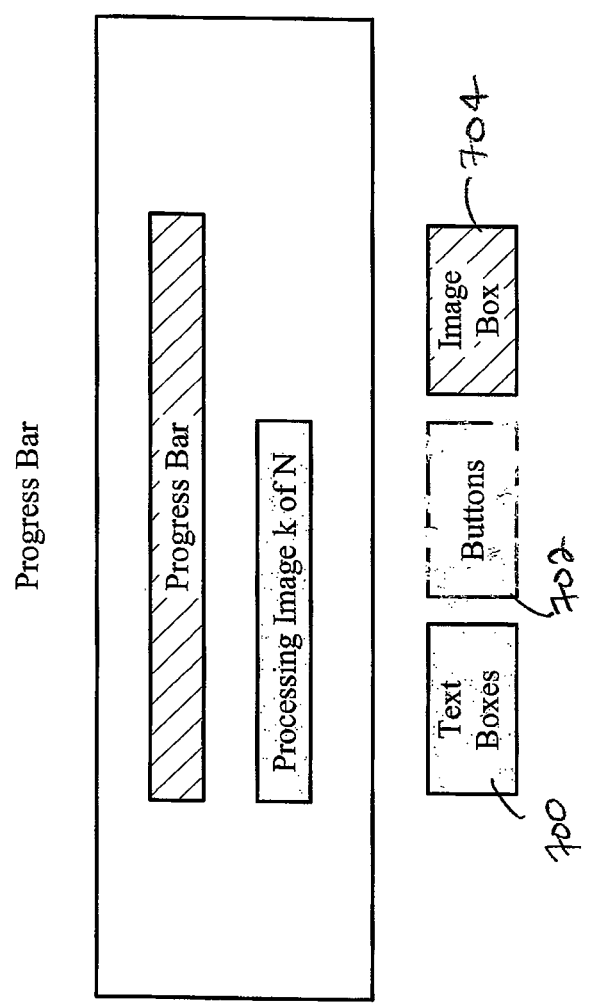

FIGS. 46 through 53 show exemplary frames/screen shots of the graphic user interface (GUI) for technicians/medical assistants used with the imaging station/booth 400 shown in FIGS. 25 and 26 with each frame/screen shot corresponding to main windows and subsequent pop up windows in the graphical user interface. FIG. 46 shows an exemplary Patient Information Entry Form having text boxes 700 represented by solid lines that show where information must be filled in and buttons 702 represented by dashed lines which may be pressed to launch a demonstration or to launch the imaging program that walks users/patients through the actual poses and takes actual pictures. FIG. 47 shows an exemplary Pose Selection Form which enables a technician/medical assistant to select one or more of the 9 poses shown in FIG. 17. FIG. 48 shows an exemplary Main Menu page/screen which enables a technician/medical assistant to manually conduct the imaging session by selecting the images to be taken, adjusting the retractable step when necessary for a posing position, and taking the pictures, etc. Boxes containing text 700 are shown with solid lines, buttons 702 that can be selected and activated are shown with dashed lines, and boxes 704 that show images are shown with cross-hatching. FIG. 49 shows an exemplary Image Review page/screen where boxes 704 that include thumbnails of acquired images are shown with hatched lines, boxes 700 with text are shown with solid lines and buttons 702 that can be selected and activated are shown with dashed lines. FIG. 50 shows an exemplary Manual Focus page/screen where boxes 704 that include live images of views seen with cameras are shown with hatched lines, boxes 700 with text are shown with solid lines, and buttons 702 that can be selected and activated are shown with dashed lines. FIG. 51 shows an exemplary Zoom Window page/screen where interactive controls 706 (for zooming in and out of images, for example) are shown with stepped hatch marks, boxes 704 that show thumbnails of acquired images are shown with hatched lines, boxes 700 with text are shown with solid lines and buttons 702 that can be selected and activated are shown with dashed lines. FIG. 52 shows an exemplary Warn Step Moving page/screen where the notice that the step is moving is emphasized in such a way that it stands out from all other parts of the page/screen. Finally, FIG. 53 shows an exemplary Progress Bar page/screen where the box 704 showing an image that shows progress of the imaging session is represented by hash marks, boxes 700 showing text are represented by solid lines, and buttons 702 that can be selected and activated are shown with dashed lines.

The system and apparatus of the present invention for total body imaging enables rapid, efficient, accurate, reliable and consistent capture of multiple body images of a user/patient to create a total body image of the user/patient. The processing time to capture the user/patient images can be 15 minutes or less thereby providing minimal time commitment for the patient and rapid capture of image data for the medical professional/provider. In addition, the process for capturing the user/patient images may be automated with minimal input from a technician/medical assistant via a technician/medical assistant graphic user interface. Video displays and/or audio components included within the station/booth provide a user/patient with instructions for undertaking accurate body positions for imaging. The cameras used to capture user/patient body images may be controlled by an auto focus algorithm that automatically adjusts the focus of one or more cameras for different user poses based on a desired body focus feature. In addition, the user/patient images (including a total user/patient body image created by stitching together a plurality of user/patient body images) as well as patient information and data (and recording of patient information and data) can be accessed by a medical professional/provider via a wired and/or wireless connection to the system of the present invention.

The detailed description of exemplary embodiments of the invention herein shows various exemplary embodiments and the best modes, known to the inventor at this time, of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included figures are non-limiting illustrations of the exemplary embodiments and modes, which similarly avail themselves to any equivalent modes or embodiments that are known or obvious to those reasonably skilled in the art.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning. It should be noted that "imaging booth" and "imaging station" are used interchangeably throughout and both terms are not meant to be limiting.

The invention claimed is:

1. A total body imaging device comprising:
   a housing having a front wall, two side walls, and a back wall;
   a frame located within the housing;
   a plurality of cameras mounted to the frame wherein the plurality of cameras comprise at least three cameras horizontally spaced along a horizontal row in relation to one another;
   body positioning members mounted to the frame wherein the body positioning members include a first set of two opposing handles extending from the back wall and located below a second set of two opposing handles extending from the back wall; and
   one or more video displays mounted to the frame.

2. The total body imaging device of claim 1 further comprising a horizontal support bar on which the plurality of cameras are mounted and an actuator capable of moving the horizontal support bar up and down.

3. The total body imaging device of claim 2 wherein the horizontal support bar is moveable to at least three predetermined vertical positions during a process for capturing photos of a user utilizing the total body imaging device.

4. The total body imaging device of claim 1 wherein the one or more video displays each comprise an audio capability.

5. The total body imaging device of claim 1 wherein said body positioning members each comprise a light emitting component with capacitive touch sensors thereby enabling the body positioning members to light up when properly engaged by a user.

6. The total body imaging device of claim 1 further comprising one or more light boxes located near the plurality of cameras wherein said one or more light boxes each comprise lighting elements.

7. The total body imaging device of claim 1 further comprising a processing unit in communication with one or more program applications related to use of the total body imaging device.

8. The total body imaging device of claim 7 wherein said one or more program applications includes a program application for taking, capturing, and storing images of a user taken with said plurality of cameras.

9. The total body imaging device of claim 8 wherein said one or more program applications includes a program application that enables a medical professional and/or medical facility to obtain wireless access to said images in order to view said images, compare a plurality of said images of a same user taken at different times, document notes relating to said images, create electronic medical records that include said images, and/or send said images and related note to another medical professional and/or medical facility.

10. The total body imaging device of claim 1 wherein each of the two opposing handles in each set of handles are moveable in a direction so that a width between the two opposing handles in each set of handles can be adjusted at the same time that a height of the two opposing handles in each set of handles is adjusted.

11. The total body imaging device of claim 1 wherein said body positioning members further includes a moveable foot plate extending from the back wall near a bottom of the back wall and a single handle extending from the back wall located above the second set of two opposing handles.

12. A total body imaging device comprising:
    a housing having a front wall, two side walls, and a back wall;
    a frame located within the housing;
    a plurality of cameras mounted to the frame wherein the plurality of cameras comprise at least three cameras horizontally spaced along a horizontal row in relation to one another;
    body positioning members mounted to the frame wherein the body positioning members include a first set of two opposing handles extending from the back wall and located below a second set of two opposing handles extending from the back wall wherein each of the handles comprise a light emitting component with capacitive touch sensors thereby enabling the handles to light up when properly engaged by a user; and
    one or more video displays mounted to the frame.

13. The total body imaging device of claim 12 further comprising a horizontal support bar on which the plurality of cameras are mounted and an actuator capable of moving the horizontal support bar up and down.

14. The total body imaging device of claim 13 wherein the horizontal support bar is moveable to at least three predetermined vertical positions during a process for capturing photos of a user utilizing the total body imaging device.

15. The total body imaging device of claim 12 wherein the one or more video displays each comprise an audio capability.

16. The total body imaging device of claim 12 further comprising one or more light boxes located near the plurality of cameras wherein said one or more light boxes each comprise lighting elements.

17. The total body imaging device of claims 12 further comprising a processing unit in communication with one or more program applications related to use of the total body imaging device.

18. The total body imaging device of claim 17 wherein said one of more program applications includes a program application for taking, capturing, and storing images of a user taken with said plurality of cameras.

19. The total body imaging device of claim 18 wherein said one or more program applications includes a program application that enables a medical professional and/or medical facility to obtain wireless access to said images in order to view said images, compare a plurality of said images of a same user taken at different times, document notes relating to said images, create electronic medical records that include said images, and/or send said images and related note to another medical professional and/or medical facility.

\* \* \* \* \*